United States Patent
Bowdish et al.

(10) Patent No.: US 6,919,189 B2
(45) Date of Patent: Jul. 19, 2005

(54) NESTED OLIGONUCLEOTIDES CONTAINING A HAIRPIN FOR NUCLEIC ACID AMPLIFICATION

(75) Inventors: Katherine S. Bowdish, Del Mar, CA (US); Shana Frederickson, Solana Beach, CA (US); John McWhirter, San Diego, CA (US); Maruyama Toshiaki, San Diego, CA (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 53 days.

(21) Appl. No.: 10/014,012

(22) Filed: Dec. 10, 2001

(65) Prior Publication Data

US 2005/0079489 A1 Apr. 14, 2005

Related U.S. Application Data

(60) Provisional application No. 60/323,400, filed on Sep. 19, 2001, and provisional application No. 60/254,669, filed on Dec. 11, 2000.

(51) Int. Cl.⁷ ............................ C12P 19/34; C12Q 1/68; C07H 21/04
(52) U.S. Cl. .......................... 435/91.2; 435/91.1; 435/6; 536/23.1; 536/24.3; 536/24.32; 536/24.33
(58) Field of Search .................. 435/6, 91.1, 91.2, 435/91.21; 536/23.1, 24.33, 24.3, 24.32

(56) References Cited

U.S. PATENT DOCUMENTS

| | | | |
|---|---|---|---|
| 4,582,788 A | 4/1986 | Erlich | 435/6 |
| 4,683,194 A | 7/1987 | Saiki et al. | 435/6 |
| 5,130,238 A | 7/1992 | Malek et al. | 435/91.1 |
| 5,595,891 A | 1/1997 | Rose et al. | 435/91.5 |
| 5,679,512 A * | 10/1997 | Laney et al. | 435/6 |
| 5,683,879 A | 11/1997 | Laney et al. | 435/6 |
| 5,744,308 A | 4/1998 | Guillou-Bonnici et al. | 435/6 |
| 5,962,272 A | 10/1999 | Chenchik et al. | 435/91.1 |
| 6,251,639 B1 | 6/2001 | Kurn | 435/91.2 |
| 6,277,607 B1 * | 8/2001 | Tyagi et al. | 435/91.2 |
| 6,582,938 B1 * | 6/2003 | Su et al. | 435/91.2 |
| 2004/0072164 A1 * | 4/2004 | Maruyama et al. | 435/6 |

FOREIGN PATENT DOCUMENTS

| | | |
|---|---|---|
| EP | 258017 | 3/1988 |
| EP | 50424 | 9/1988 |
| EP | 84796 | 2/1990 |
| EP | 237362 | 3/1992 |
| EP | 201184 | 12/1992 |
| EP | 368684 | 3/1994 |
| WO | WO 9014430 | 11/1990 |
| WO | WO 97/04131 | * 2/1997 |

OTHER PUBLICATIONS

Mullis et al. Cold spring Harbor Symp. Quant. Biol. 51:263–273; Mullisk.
Patel et al. Proc.Natl. Acad. Sci. USA 93:2969–2974 (1996).

* cited by examiner

*Primary Examiner*—Kenneth R. Horlick
*Assistant Examiner*—Cynthia Wilder
(74) *Attorney, Agent, or Firm*—Carter, DeLuca, Farrell & Schmidt

(57) ABSTRACT

Templates that are engineered to contain a predetermined sequence and a hairpin structure are provided by a nested oligonucleotide extension reaction. The engineered template allows Single Primer Amplification (SPA) to amplify a target sequence within the engineered template. In particularly useful embodiments, the target sequences from the engineered templates are cloned into expression vehicles to provide a library of polypeptides or proteins, such as, for example, an antibody library.

38 Claims, 8 Drawing Sheets

| clones | SEQ ID NO: | FR1 | CDR1 | FR2 |
|---|---|---|---|---|
| A7, B1, F8, G2 | SEQ ID NO: 209 | ESDGAVVQPGGSLRLSCAASGF | IFDDFAMH | WLRQVPGKGLQWVGL |
| C2, E6 | SEQ ID NO: 210 | QPGGSLRLSCAASGF | TLSSSAMS | WVRQAPGKGLEFVAV |
| A4 | SEQ ID NO: 211 | QPGGSLRLSCAASGF | TLSSSAMS | WVRQAPGKGLEFVAV |
| F6 | SEQ ID NO: 212 | AWYSRGSPCLSCAASGF | TLSSSAMS | WVRQAPGKGLEFVAV |
| E9, G7 | SEQ ID NO: 213 | ESDPGLVKPSETPSLTCTVSGG | SISSTMYFWG | WIRQPPGKGLEWIAS |
| F3, G4 | SEQ ID NO: 214 | PGLVKPSETLSLTCTVSGG | SISNIMYFWG | WIRQPPGKGLEWIAS |
| A12, B5, B8, B9 | SEQ ID NO: 215 | ESDPGLVQPSQTLSLTCTVSGG | SLRSDDYWS | WIRQSPGKGLEWIAY |
| E8 | SEQ ID NO: 216 | PVQPLEF | TFTDHWMH | WVRQAPGKGLVWLAR |
| F7 | SEQ ID NO: 217 | ESEGGLVQPGGSLRLSCAASGF | TFSSYAMT | WVRQAPGKGLEWVST |
| E11 | SEQ ID NO: 218 | LAGVEVVQPGGSLRLSCAASGF | TFDDYAMH | WLRQIPGKGLQWVSL |

Figure 5A

| clones | SEQ ID NO: | CDR2 | FR3 |
|---|---|---|---|
| A7, B1, F8, G2 | SEQ ID NO: 209 (cont'd) | MSWDGVSAYYADSVEG | RFTISRDNKKNALYLQMNSLGVEDTALYYCAK |
| C2, E6 | SEQ ID NO: 209 (cont'd) | SSGNGFSTYYGDSVKG | RFTISRDNSKNMVYLQMDSLRAEDTAKYHCAK |
| A4 | SEQ ID NO: 209 (cont'd) | SSGNGFSTYYGDSVKG | RFTISRDNSKNMVYLQMDSLRAEDTAKYHCAK |
| F6 | SEQ ID NO: 209 (cont'd) | SSGNGFSTYYGDSVKG | RFTISRDNSKNMVYLQMDSLRAEDTAKYHCAK |
| E9, G7 | SEQ ID NO: 209 (cont'd) | IYYSGTT-YYNPSLRS | RVTMSVDTSKNQLSLKLNSVTAADTAVYYCAR |
| F3, G4 | SEQ ID NO: 209 (cont'd) | IYYSGTT-YYNPSLRS | RVTMSVDTSKNQLSLKLNSVTAADTAVYYCAR |
| A12, B5, B8, B9 | SEQ ID NO: 209 (cont'd) | ISYTGGT-YYNPSLKS | RVTISVDTSRNQFSLRLRSVTAADSAVYFCAS |
| E8 | SEQ ID NO: 209 (cont'd) | INRDGSDTTYADSVTG | RFTISRDNGKNTVSLQMDSLSVDDTAVYYCAR |
| F7 | SEQ ID NO: 209 (cont'd) | MTGSGGVTYYADVLKG | RFTISRDNSKNTLYLQMNSLRAEDTAVYYCAK |
| E11 | SEQ ID NO: 209 (cont'd) | LSWDGVSAYYADSVEG | RFTISRDNKKNSLYLQMNSLRAEDVALYYCAK |

Figure 5B

| clones | SEQ ID NO: | CDR3 | FR4 |
|---|---|---|---|
| A7, B1, F8, G2 | SEQ ID NO: 209 (cont'd) | DMGGGLRFPHF | WGQGTPVTVSA |
| C2, E6 | SEQ ID NO: 210 (cont'd) | VRYGPRSHFFFDP | WGQGTLVTVSS |
| A4 | SEQ ID NO: 211 (cont'd) | VRYGPRSHFFFDP | WGPGNPGHRLL |
| F6 | SEQ ID NO: 212 (cont'd) | VRYGPRSHFFFDP | WGQGTLVTVSS |
| E9, G7 | SEQ ID NO: 213 (cont'd) | PTIYYFDGRTSYYPGEAAFDI | WGQGTTV |
| F3, G4 | SEQ ID NO: 214 (cont'd) | PTIYYFDGRTSYYPGEAAFDI | WGQGTTVTV |
| A12, B5, B8, B9 | SEQ ID NO: 215 (cont'd) | TTAVTTTFDY | WGRGTLVTVS |
| E8 | SEQ ID NO: 216 (cont'd) | GGHHTVLSPLSNWFDP | WGQGTLVTVS |
| F7 | SEQ ID NO: 217 (cont'd) | GYGLFDY | WGQGTLVTVS |
| E11 | SEQ ID NO: 218 (cont'd) | DMGGAQRLPDH | WGQGTLVTVSS |

Figure 5C

| clones | SEQ ID NO: | FR1 | CDR1 | FR2 |
|---|---|---|---|---|
| 4D, 10C, 4G | SEQ ID NO: 219 | GGGLVQPGASVKVSCKASGY | TFSDYFMH | CVRQAPGQGLEWMGL |
| 8A | SEQ ID NO: 220 | RCPAKLLDT | PFSVYFMH | WVRQAPGQGLEWMGL |
| 3G | SEQ ID NO: 221 | RCPAKLLDT | PSGDYFMH | WVRQAPGQGLEWMGL |
| 1A | SEQ ID NO: 222 | SGGLVQRGAKVLRLSCVASGF | TFSSSAMS | WVRQAPGKGLEWVSV |
| 7H | SEQ ID NO: 223 | LGS | PYSSSAMS | WVRQAPGKGLE?VSF |
| 6F | SEQ ID NO: 224 | VESGGVVQPGAKVLRLSCAASGF | SFEDYAMH | WVRQPPGKGLEWVAL |
| 4F | SEQ ID NO: 225 | AASGF | IFDDFAMH | WFQAVPGKGLQWVGL |
| 5A | SEQ ID NO: 226 | FWLGGPWRLSCAVSGY | TLSSSAMI | WVRQPPGKGLEFVSV |
| 1D | SEQ ID NO: 227 | GGGLVQPGASLRLSCVASGF | TLSSSAMS | CVRQAPGKGLEWVSV |
| 7E | SEQ ID NO: 228 | WGRRGPAWGVPVGSPVQPIGY | TFDDYAMH | WLRQIPGKGLQWVSL |
| 9E | SEQ ID NO: 229 | WTGGGVVQPGGSLRVSVAASGY | TFDDYAMH | WLRQIPGKGLQWVSL |
| 12B | SEQ ID NO: 230 | AESGGGVVQPGGSLRLSCAASGF | TFSRYTLS | WVRQAPGKGLEWVSY |

Figure 6A

| clones | SEQ ID NO: | CDR2 | FR3 |
|---|---|---|---|
| 4D, 10C, 4G | SEQ ID NO: 219 (cont'd) | VNPTNGYTAYAPKFQG | RVTMTRQRFTSTVYMELSSLRSEDTAVYFCAR |
| 8A | SEQ ID NO: 220 (cont'd) | VNPTNGYTAYAPKFQG | RVTMTRQRFTSTVYMELSSLRSEDTAVYFCAR |
| 3G | SEQ ID NO: 221 (cont'd) | VNPTNGYTAYAPKFQG | RVTMTRQRFTSTVYMELSSLRSEDTAVYFCAR |
| 1A | SEQ ID NO: 222 (cont'd) | ISGNGFSTYYADSVK | RFTISRDNSKNTLYLQMNSLRAEDTAEYYCTK |
| 7H | SEQ ID NO: 223 (cont'd) | IS?NGLSAYYADSVKG | RFTISRDNS?NTVYLQMNSLRSEDTAEYYCVK |
| 6F | SEQ ID NO: 224 (cont'd) | ISWDVISAYYADSVKG | RFTISRDNSKNSLYLQMDSLRPEDSGLYYCGR |
| 4F | SEQ ID NO: 225 (cont'd) | MSWDGVSAYYADSVEG | RFTISRDNKKNALYLQMNSLGVEDTALYFCAK |
| 5A | SEQ ID NO: 226 (cont'd) | ISGNGLSAYYADSVKG | RFTISRDNSKNTVYLQMNSLRAEDTAEYYCVK |
| 1D | SEQ ID NO: 227 (cont'd) | SSGNGFSAYYADSVKG | RFTISRDNSKNTLYLQMNSLVAEDTAEYYCTK |
| 7E | SEQ ID NO: 228 (cont'd) | LSWDGVSAYYADSVEG | RFTISRDNKKNSLYLQMNSLVAEDTALYFCAK |
| 9E | SEQ ID NO: 229 (cont'd) | LSWDGVSAYYADSVEG | RFTISRDN?KNSLYLQMNSLIAEDTALYFCAK |
| 12B | SEQ ID NO: 230 (cont'd) | ISTDGSTIYYTDSVKG | RFTISRDNAKNSLSLQMISLRDEDTAVYYCAR |

Figure 6B

| clones | SEQ ID NO: | CDR3 | FR4 |
|---|---|---|---|
| 4D, 10C, 4G | SEQ ID NO: 219 (cont'd) | VKSSDSIDAFDI | WGQGTMVTVSS |
| 8A | SEQ ID NO: 220 (cont'd) | VKSSDSIDAFDI | WGQGTMVTVSS |
| 3G | SEQ ID NO: 221 (cont'd) | VKSSDSIDAFDI | WGQGTMVTVSS |
| 1A | SEQ ID NO: 222 (cont'd) | VKYGSGHFWFDP | WGQGTLVTVSS |
| 7H | SEQ ID NO: 223 (cont'd) | V?YGSRSHF | |
| 6F | SEQ ID NO: 224 (cont'd) | DIGQQRTMDV | WGQGTTVTVSS |
| 4F | SEQ ID NO: 225 (cont'd) | DMGGGLRFPHF | WGQGTPVTVSA |
| 5A | SEQ ID NO: 226 (cont'd) | VKYGSRSHFFEDS | WGQGTLVSVSP |
| 1D | SEQ ID NO: 227 (cont'd) | VNYGSRSHFYFGS | WGHGTLVIVSS |
| 7E | SEQ ID NO: 228 (cont'd) | DMGGAQRLPDH | WGQGTLVTVSS |
| 9E | SEQ ID NO: 229 (cont'd) | DMGGAQRLPDH | WGQGTLVTVSS |
| 12B | SEQ ID NO: 230 (cont'd) | VFFGGNFRAHWYFDL | WGRGTLVAVSS |

Figure 6C

NESTED OLIGONUCLEOTIDES CONTAINING A HAIRPIN FOR NUCLEIC ACID AMPLIFICATION

RELATED APPLICATIONS

This application claims priority to U.S. Provisional Application No. 60/254,669 filed December 11, 2000 and to U.S. Provisional Application No. 60/323,400 filed Sep. 19, 2001. The disclosures of both these Provisional Applications are incorporated herein in their entirety by this reference.

TECHNICAL FIELD

This disclosure relates to engineered templates useful for amplification of a target nucleic acid sequence. More specifically, templates which are engineered to contain a predetermined sequence and a hairpin structure are provided by a nested oligonucleotide extension reaction. The engineered templates allow Single Primer Amplification (SPA) to amplify a target sequence within the engineered template. In particularly useful embodiments, the target sequences from the engineered templates are cloned into expression vehicles to provide a library of polypeptides or proteins, such as, for example, an antibody library.

BACKGROUND OF RELATED ART

Methods for nucleic acid amplification and detection of amplification products assist in the detection, identification, quantification, isolation and sequence analysis of nucleic acid sequences. Nucleic acid amplification is an important step in the construction of libraries from related genes such as, for example, antibodies. These libraries can be screened for antibodies having specific, desirable activities. Nucleic acid analysis is important for detection and identification of pathogens, detection of gene alteration leading to defined phenotypes, diagnosis of genetic diseases or the susceptibility to a disease, assessment of gene expression in development, disease and in response to defined stimuli, as well as the various genome projects. Other applications of nucleic acid amplification method include the detection of rare cells, detection of pathogens, and the detection of altered gene expression in malignancy, and the like. Nucleic acid amplification is also useful for qualitative analysis (such as, for example, the detection of the presence of defined nucleic acid sequences) and quantification of defined gene sequences (useful, for example, in assessment of the amount of pathogenic sequences as well as the determination of gene multiplication or deletion, and cell transformation from normal to malignant cell type, etc.). The detection of sequence alterations in a nucleic acid sequence is important for the detection of mutant genotypes, as relevant for genetic analysis, the detection of mutations leading to drug resistance, pharmacogenomics, etc.

There are many variations of nucleic acid amplification, for example, exponential amplification, linked linear amplification, ligation-based amplification, and transcription-based amplification. One example of exponential nucleic acid amplification method is polymerase chain reaction (PCR) which has been disclosed in numerous publications. See, for example, Mullis et al. Cold Spring Harbor Symp. Quant. Biol. 51:263–273 (1986); Mullis K. EP 201,184; Mullis et al. U.S. Pat. No. 4,582,788; Erlich et al. EP 50,424, EP 84,796, EP 258,017, EP 237,362; and Saiki R. et al. U.S. Pat. No. 4,683,194. In fact, the polymerase chain reaction (PCR) is the most commonly used target amplification method. PCR is based on multiple cycles of denaturation, hybridization of two different oligonucleotide primers, each to opposite strand of the target strands, and primer extension by a nucleotide polymerase to produce multiple double stranded copies of the target sequence.

Amplification methods that employ a single primer, have also been disclosed. See, for example, U.S. Pat. Nos. 5,508,178; 5,595,891; 5,683,879; 5,130,238; and 5,679,512. The primer can be a DNA/RNA chimeric primer, as disclosed in U.S. Pat. No. 5,744,308.

Some amplification methods use template switching oligonucleotides (TSOs) and blocking oligonucleotides. For example, a template switch amplification in which chimeric DNA primer are utilized is disclosed in U.S. Pat. Nos. 5,679,512; 5,962,272; 6,251,639; and by Patel et al. Proc. Natl. Acad. Sci. U.S.A. 93:2969–2974 (1996).

However the previously described target amplification methods have several drawbacks. For example, the transcription base amplification methods, such as Nucleic Acid Sequence Based Amplification (NASBA) and transcription mediated amplification (TMA), are limited by the need for incorporation of the polymerase promoter sequence into the amplification product by a primer, a process prone to result in non-specific amplification. Another example of a drawback of the current amplification methods is the requirement of two binding events which may have optimal binding at different temperatures. This combination of factors results in increased likelihood of mis-priming and resultant amplification of sequences other than the target sequence. Therefore, there is a need for improved nucleic acid amplification methods that overcome these drawbacks. The invention provided herein fulfills this need and provides additional benefits.

SUMMARY

A method of amplifying nucleic acid has been discovered which includes the steps of a) annealing a primer to a template nucleic acid sequence, the primer having a first portion which anneals to the template and a second portion of predetermined sequence; b) synthesizing a polynucleotide that anneals to and is complementary to the portion of the template between the location at which the first portion of the primer anneals to the template and the end of the template, the polynucleotide having a first end and a second end, wherein the first end incorporates the primer; c) separating the polynucleotide synthesized in step (b) from the template; d) annealing a nested oligonucleotide to the second end of the polynucleotide synthesized in step (b), the nested oligonucleotide having a first portion that anneals to the second end of the polynucleotide, and a second portion having a hairpin structure; e) extending the polynucleotide synthesized in step (b) to provide a portion that is complementary to the hairpin structure and a terminal portion that is complementary to the predetermined sequence; and f) amplifying the extended polynucleotide using a single primer having the predetermined sequence.

In an alternative embodiment, the method of amplifying nucleic acid includes the steps of a) annealing a primer and a boundary oligonucleotide to a template nucleic acid sequence, the primer having a first portion which anneals to the template and a second portion of predetermined sequence; b) synthesizing a polynucleotide that anneals to and is complementary to the portion of the template between the location at which the first portion of the primer anneals to the template and the portion of the template to which the boundary oligonucleotide anneals, the polynucleotide having a first end and a second end, wherein the first end incorporates the primer; c) separating the polynucleotide synthesized in step (b) from the template; d) annealing a nested oligonucleotide to the second end of the polynucleotide synthesized in step (b), the nested oligonucleotide having a first portion that anneals to the second end of the polynucleotide and a second portion having a hairpin structure; e) extending the polynucleotide synthesized in step (b) to provide a portion that is complementary to the hairpin structure and a terminal portion that is complementary to the predetermined sequence; and f) amplifying the extended polynucleotide using a single primer having the predetermined sequence.

In yet another embodiment, the method of amplifying nucleic acid includes the steps of a) annealing an oligo dT primer and a boundary oligonucleotide to an mRNA template; b) synthesizing a polynucleotide that anneals to and is complementary to the portion of the template between the location at which the first portion of the primer anneals to the template and the portion of the template to which the boundary oligonucleotide anneals, the polynucleotide having a first end and a second end, wherein the first end incorporates the primer; c) separating the polynucleotide synthesized in step (b) from the template; d) annealing a nested oligonucleotide to the second end of the polynucleotide synthesized in step (b), the nested oligonucleotide having a first portion that anneals to the second end of the polynucleotide, and a second portion having a hairpin structure; e) extending the polynucleotide synthesized in step (b) to provide an extended polynucleotide that includes a portion that is complementary to the hairpin structure and a poly A terminal portion; and f) amplifying the extended polynucleotide using a single primer.

In another aspect an engineered nucleic acid strand is disclosed which has a predetermined sequence at a first end thereof, a sequence complementary to the predetermined sequence at the other end thereof, and a hairpin structure therebetween.

In yet another aspect, a method of amplifying a nucleic acid strand has been discovered which includes the steps of providing an engineered nucleic acid strand having a predetermined sequence at a first end thereof, a sequence complementary to the predetermined sequence at the other end thereof and a hairpin structure therebetween, and contacting the engineered nucleic acid strand with a primer containing at least a portion of the predetermined sequence in the presence of a polymerase and nucleotides under conditions suitable for polymerization of the nucleotides.

Once the engineered nucleic acid is amplified a desired number of times, restriction sites can be used to digest the strand so that the target nucleic acid sequence can be ligated into a suitable expression vector. The vector may then be used to transform an appropriate host organism using standard methods to produce the polypeptide or protein encoded by the target sequence. In particularly useful embodiments, the techniques described herein are used to amplify a family of related sequences to build a complex library, such as, for example, an antibody library.

BRIEF DESCRIPTION OF DRAWINGS

FIGS. 5A–5C is a chart showing the sequences of clones produced in Example 4.

FIGS. 6A–6C is a chart showing the sequences of clones produced in Example 7.

DETAILED DESCRIPTION OF PREFERRED EMBODIMENTS

Figure 1:
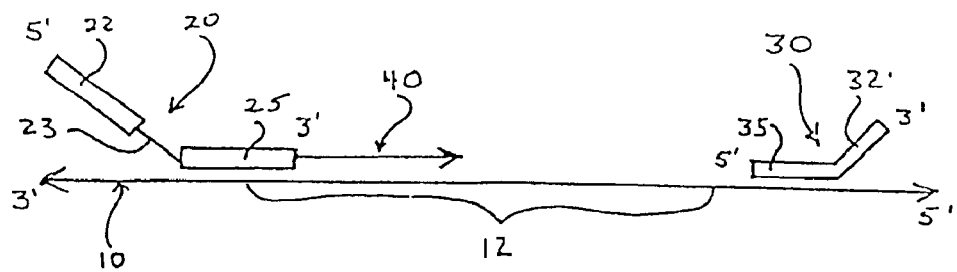
FIG. 1 is a schematic illustration of a primer and boundary oligo annealed to a template.

The present disclosure provides a method of amplifying a target nucleic acid sequence. In particularly useful embodiments, the target nucleic acid sequence is a gene encoding a polypeptide or protein. The disclosure also describes how the products of the amplification may be cloned and expressed in suitable expression systems. In particularly useful embodiments, the techniques described herein are used to amplify a family of related sequences to build a complex library, such as, for example, an antibody library.

The target nucleic acid sequence is exponentially amplified through a process that involves only a single primer. The ability to employ a single primer (i.e., without the need for both forward and reverse primers each having different sequences) is achieved by engineering a strand of nucleic acid that contains the target sequence to be amplified. The engineered strand of nucleic acid (sometimes referred to herein as the "engineered template") is prepared from two templates; namely, 1) a starting material that is a natural or synthetic nucleic acid (e.g., RNA, DNA or cDNA) containing the sequence to be amplified and 2) a nested oligonucleotide that provides a hairpin structure. The starting material can be used directly as the original template, or, alternatively, a strand complementary to the starting material can be prepared and used as the original template. The nested oligonucleotide is used as a template to extend the nucleotide sequence of the original template during creation of the engineered strand of nucleic acid. The engineered strand of nucleic acid is created from the original template by a series of manipulations that result in the presence of a predetermined sequence at one end thereof and a hairpin structure. It is these two features that allow amplification using only a single primer.

Any nucleic acid, in purified or nonpurified form, can be utilized as the starting material for the processes described herein provided it contains or is suspected of containing the target nucleic acid sequence to be amplified. Thus, the starting material employed in the process may be, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be utilized. The target nucleic acid sequence to be amplified may be a fraction of a larger molecule or can be present initially as a discrete molecule. The starting nucleic acid may contain more than one desired target nucleic acid sequence which may be the same or different. Therefore, the present process may be useful not only for producing large amounts of one target nucleic acid sequence, but also for amplifying simultaneously more than one different target nucleic acid sequence located on the same or different nucleic acid molecules.

The nucleic acids may be obtained from any source, for example: genomic or cDNA libraries, plasmids, cloned DNA or RNA, or from natural DNA or RNA from any source, including bacteria, yeast, viruses, and higher organisms such as plants or animals. The nucleic acid can be naturally occurring or synthetic, either totally or in part. Techniques for obtaining and producing the nucleic acids used in the present processes are well known to those skilled in the art. If the nucleic acid contains two strands, it is necessary to separate the strands of the nucleic acid before it can be used as the original template, either as a separate step or simultaneously with the synthesis of the primer extension products. Additionally, if the starting material is first strand DNA, second strand DNA may advantageously be created by processes within the purview of those skilled in the art and used as the original template from which the engineered template is created.

First strand cDNA and mRNA are particularly useful as the original template for the present methods. Suitable methods for generating DNA templates are known to and readily selected by those skilled in the art. In one embodiment, $1^{st}$ strand cDNA is synthesized in a reaction where reverse transcriptase catalyzes the synthesis of DNA complementary to any RNA starting material in the presence of an oligodeoxynucleotide primer and the four deoxynucleoside triphosphates, dATP, dGTP, dCTP, and TTP. The reaction is initiated by the non-covalent bonding of the oligo-deoxynucleotide primer to the 3' end of mRNA followed by stepwise addition of the appropriate deoxynucleotides as determined by base pairing relationships with the mRNA nucleotide sequence, to the 3' end of the growing chain. As those skilled in the art will appreciate, all mRNA in a sample can be used to generate first strand cDNA through the annealing of oligo dT to the poly A tail of the mRNA.

Once the original template is obtained, a primer 20 and a boundary oligonucleotide 30 arc annealed to the original template 10. (See FIG. 1.) A strand of nucleic acid complementary to the portion of the original template beginning at the 3' end of the primer up to about the 5' end of the boundary oligonucleotide is polymerized.

The primer 20 that is annealed to the original template includes a portion 25 that anneals to the original template and optionally a portion 22 of predetermined sequence that preferably does not anneal to the template, and optionally a restriction site 23 between portions 22 and 25. Thus, for example, where the original template is mRNA, a portion having a predetermined sequence that does not anneal to the template is not needed, but rather the primer can be any gene-specific internal sequence of the mRNA or oligo dT which will anneal to the unique poly A tail of the mRNA.

The primer anneals to the original template adjacent to the target sequence 12 to be amplified. It is contemplated that the primer can anneal to the original template upstream of the target sequence (or downstream in the case, e.g., of an mRNA original template) to be amplified, or that the primer may overlap the beginning of the target sequence 12 to be amplified as shown in FIG. 1. The predetermined sequence of portion 22 of the primer is selected so as to provide a sequence to which the single primer used during the amplification process can hybridize as described in detail below. Preferably, the predetermined sequence is not native in the original template and does not anneal to the original template, as shown in FIG. 1. Optionally, the predetermined sequence may include a restriction site useful for insertion of a portion of the engineered template into an expression vector as described more fully hereinbelow.

The boundary oligonucleotide 30 that is annealed to the original template serves to terminate polymerization of the nucleic acid. Any oligonucleotide capable of terminating nucleic acid polymerization may be utilized as the boundary oligonucleotide 30. In a preferred embodiment the boundary oligonucleotide includes a first portion 35 that anneals to the original template 10 and a second portion 32 that is not susceptible to an extension reaction. Techniques to prevent the boundary oligo from acting as a site for extension are within the purview of one skilled in the art. By way of example, portion 32 of the boundary oligo 30 may be designed so that it does not anneal to the original template 10 as shown in FIG. 1. In such embodiments, the boundary oligonucleotide 30 prevents further polymerization but does not serve as a primer for nucleic acid synthesis because the 3' end thereof does not hybridize with the original template 10. Alternatively, the 3' end of the boundary oligo 30 might be designed to include locked nucleic acid to achieve the same effect. Locked nucleic acid is disclosed for example in WO 99/14226, the contents of which are incorporated herein by reference. Those skilled in the art will envision other ways of ensuring that no extension of the 3' end of the boundary oligo occurs.

Primers and oligonucleotides described herein may be synthesized using established methods for oligonucleotide synthesis which are well known in the art. Oligonucleotides, including primers of the present invention include linear oligomers of natural or modified monomers or linkages, such as deoxyribonucleotides, ribonucleotides, and the like, which are capable of specifically binding to a target polynucleotide by way of a regular pattern of monomer-to-monomer interactions such as Watson-Crick base pairing. Usually monomers are linked by phosphodiester bonds or their analogs to form oligonucleotides ranging in size from a few monomeric units e.g., 3–4, to several tens of monomeric units. A primer is typically single-stranded, but may be double-stranded. Primers are typically deoxyribonucleic acids, but a wide variety of synthetic and naturally occurring primers known in the art may be useful for the methods of the present disclosure. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers may be labeled with, e.g., chromogenic, radioactive, or fluorescent moieties and used as detectable moieties.

Polymerization of nucleic acid can be achieved using methods known to those skilled in the art. Polymerization is generally achieved enzymatically, using a DNA polymerase or reverse transcriptase which sequentially adds free nucleotides according to the instructions of the template. The selection of a suitable enzyme to achieve polymerization for a given template and primer is within the purview of those skilled in the art. In certain embodiments, the criteria for selection of polymerases includes lack exonuclease activity or DNA polymerases which do not possess a strong exonuclease activity. DNA polymerases with low exonuclease activity for use in the present process may be isolated from natural sources or produced through recombinant DNA techniques. Illustrative examples of polymerases that may be used, are, without limitation, T7 Sequenase v. 2.0, the Klenow Fragment of DNA polymerase I lacking exonuclease activity, the Klenow Fragment of Taq Polymerase, exo.- Pfu DNA polymerase, Vent. (exo.-) DNA polymerase, and Deep Vent. (exo-) DNA polymerase.

Figure 2A:
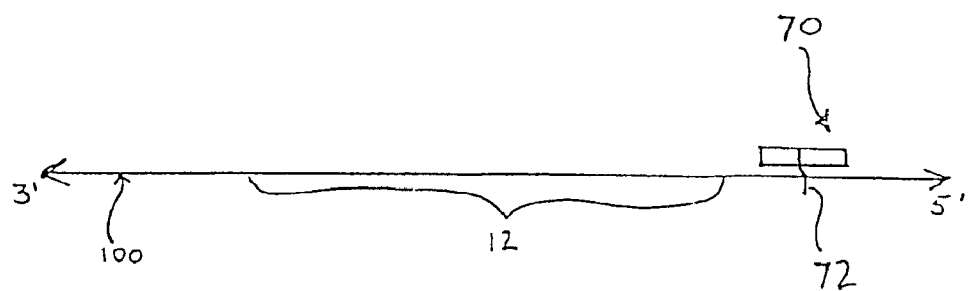
FIG. 2A is a schematic illustration of a restriction oligo annealed to a nucleic acid strand.
Figure 2B:
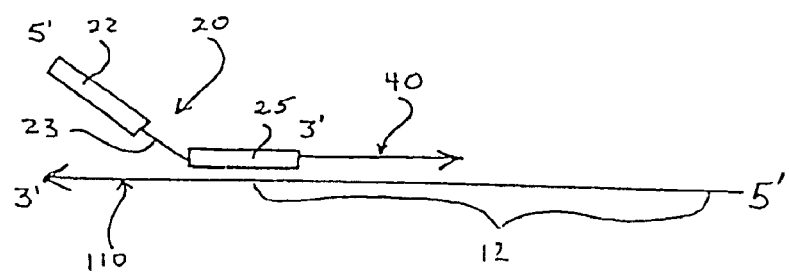
FIG. 2B is a schematic illustration of a primer annealed to a template that has a shortened 5' end.

In a particularly useful embodiment, the use of a boundary oligonucleotide is avoided by removing unneeded portions of the starting material by digestion. In this embodiment, which is shown schematically in FIG. 2A, a restriction oligonucleotide 70 is annealed to the starting material 100 at a preselected location. The restriction oligonucleotide provides a double stranded portion on the starting material containing a restriction site 72. Suitable restriction sites, include, but are not limited to Xho I, Spe I, Nhe1, Hind III, Nco I, Xma I, Bgl II, Bst I, and Pvu I. Upon exposure to a suitable restriction enzyme, the starting material is digested and thereby shortened to remove unnecessary sequence while preserving the desired target sequence 12 (or portion thereof) to be amplified on what will be used as the original template 110. Once the original template 10 is obtained, a primer 20 is annealed to the original template 110 (see FIG. 2B) adjacent to or overlapping with the target sequence 12 as described above in connection with previous embodiments. A strand of nucleic acid 40 complementary to the portion of the original template between the 3' end of the primer 20 and the 5' end of the original template 110 is polymerized. As those skilled in the art will appreciate, in this embodiment where a restriction oligonucleotide is employed to generate the original template, there is no need to use a boundary oligonucleotide, because primer extension can be allowed to proceed all the way to the 5' end of the shortened original template 110.

Once polymerization is complete (i.e., growing strand 40 reaches the boundary oligonucleotide 30 or the 5' end of the shortened original template 110), the newly synthesized complementary strand is separated from the original template by any suitable denaturing method including physical, chemical or enzymatic means. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63–67, and techniques for using RecA are reviewed in C. Radding, Ann. Rev. Genetics, 16:405–37 (1982).

The newly synthesized complementary strand thus includes sequences provided by the primer 20 (e.g., the predetermined sequence 22, the optional restriction site 23 and the annealing portion 25 of the primer) as well as the newly synthesized portion 45 that is complementary to the portion of the original template 10 between the location at which the primer 20 was annealed to the original template 10 and either the portion of the original template 10 to which the boundary oligonucleotide 30 was annealed or through to the shortened 5' end of the original template. See FIG. 3.

Optionally, multiple rounds of polymerization using the original template and a primer are performed to produce multiple copies of the newly synthesized complementary strand for use in subsequent steps. It is contemplated that 2 to 10 rounds or more (preferably, 15–25 rounds) of linear amplification can be performed when a DNA template is used. Making multiple copies of the newly synthesized complementary strand at this point in the process (instead of waiting until the entire engineered template is produced before amplifying) helps ensure that accurate copies of the target sequence are incorporated into the engineered templates ultimately produced. It is believed that multiple rounds of polymerization based on the original template provides a greater likelihood that a better representation of all members of the library will be achieved, therefore providing greater diversity compared to a single round of polymerization.

Figure 3:
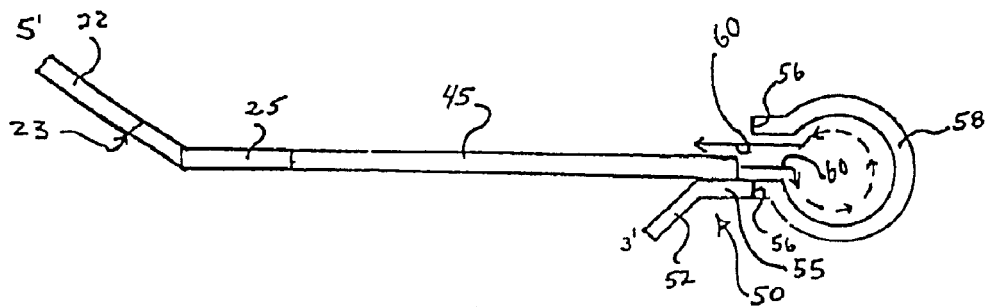
FIG. 3 is a schematic illustration of a nested oligo having a hairpin structure annealed to a newly synthesized nucleic acid strand.

The next step in preparing the engineered template involves annealing a nested oligonucleotide 50 to the 3' end of the newly synthesized complementary strand, for example as shown in FIG. 3. As seen in FIG. 3, the nested oligonucleotide 50 provides a template for further polymerization necessary to complete the engineered template. Nested oligonucleotide 50 includes a portion 52 that does not hybridize and/or includes modified bases to the newly synthesized complementary strand, thereby preventing the nested oligonucleotide from serving as a primer. Nested oligonucleotide 50 also includes a portion 55 that hybridizes to the 3' end of the newly synthesized complementary strand. Nested oligonucleotide 50 may optionally also define a restriction site 56. The final portion 58 of nested oligonucleotide 50 contains a hairpin structure. From the point at which portion 55 extends beyond the 3' end of the beginning the newly synthesized complementary strand, the nested oligonucleotide serves as a template for further polymerization to form the engineered template. It should be understood that the nested oligo may contain part of the target sequence (if part thereof was truncated in forming the original template) or may include genes that encode a polypeptide or protein (or portion thereof) such as, for example, one or more CDR's or Framework regions or constant regions of an antibody. It is also contemplated that a collection of nested oligonucleotides having different sequences can be employed, thereby providing a variety of templates which results in a library of diverse products. Thus, polymerization will extend the newly synthesized complementary strand by adding additional nucleic acid 60 that is complementary to the nested oligonucleotide as shown in FIG. 3. Techniques for achieving polymerization are within the purview of one skilled in the art. As previously noted, in selecting a suitable polymerase, an enzyme lacking exonuclease activity may be employed to prevent the 3' end of the nested oligo from acting as a primer. Because of hairpin structure 50 of the nested oligonucleotide, eventually the newly synthesized complementary strand will turn back onto portion 45 of the same strand which will then serve as the template for further polymerization. Polymerization will continue until the end of the primer is reached, at which point the newly synthesized strand will terminate with a portion whose sequence is complementary to the primer.

Figure 4A:
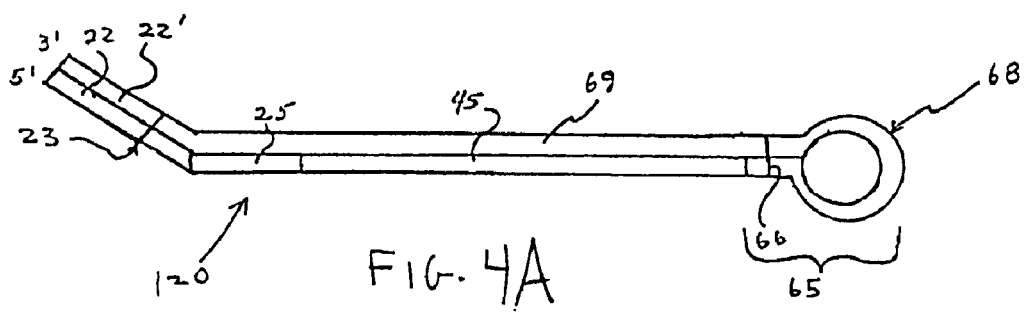
FIG. 4A is a schematic illustration of an engineered template in accordance with this disclosure.

Once polymerization is complete, the engineered template 120 is separated from the nested oligonucleotide 50 by techniques well known to those skilled in the art such as, for example, heat denaturation. The resulting engineered template 120 contains a portion derived from the original primer 20, portion 45 that is complementary to a portion of the original template, and portion 65 that is complementary to a portion of the nested oligonucleotide and includes a hairpin structure 68, and a portion 69 that is complementary to portion 45. (See FIGS. 4A and B.) The 3' end of engineered template 120 includes a portion containing a sequence that is complementary to primer 20. Thus, for example, as shown in FIG. 4A, the 3' end of engineered template 120 includes portion 22' containing a sequence that is complementary to the predetermined sequence of portion 22 of primer 20. This allows for amplification of the desired sequence contained within engineered template 120 using a single primer having the same sequence as the predetermined sequence of primer portion 22 (or a primer that is complementary thereto) using techniques known to those of ordinary skill in the art.

Figure 4B:
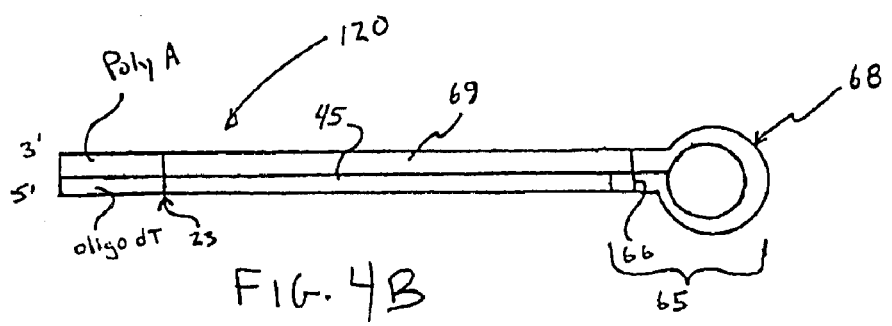
FIG. 4B is a schematic illustration of an engineered template in accordance with an alternative embodiment.

As another example (shown in FIG. 4B), where mRNA is used as the template and oligo dT is used as the primer, the 3' end of engineered template 120 includes poly A portion that is complementary to the oligo dT primer. In this case, any sequence along portion 45 can be selected for use as the primer to be annealed to portion 69 once the engineered template is denatured for single primer amplification. Optionally, the primer may include a non-annealing portion, such as, for example, a portion defining a restriction site.

During single primer amplification, the presence of a polymerase having exonuclease activity is preferred because such enzymes are known to provide a "proofreading" function and have relatively higher processivity compared to polymerases lacking exonuclease activity.

Due to hairpin structure 68 there is internal self annealing between the 5' end predetermined sequence and the 3' end sequence which is complementary to the predetermined sequence on the engineered template. Upon denaturation and addition of a primer having the predetermined sequence, the primer will hybridize to the template and amplification can proceed.

After amplification is performed, the products may be detected using any of the techniques known to those skilled in the art. Examples of methods used to detect nucleic acids include, without limitation, hybridization with allele specific oligonucleotides, restriction endonuclease cleavage, single-stranded conformational polymorphism (SSCP), analysis-gel electrophoresis, ethidium bromide staining, fluorescence resonance energy transfer, hairpin FRET essay, and TaqMan assay.

Once the engineered nucleic acid is amplified a desired number of times, restriction sites 23 and 66 or any internal restriction site can be used to digest the strand so that the target nucleic acid sequence can be ligated into a suitable expression vector. The vector may then be used to transform an appropriate host organism using standard methods to produce the polypeptide or protein encoded by the target sequence.

In particularly useful embodiments, the methods described herein are used to amplify target sequences encoding antibodies or portions thereof, such as, for example the variable regions (either light or heavy chain) using cDNA of an antibody. In this manner, a library of antibodies can be amplified and screened. Thus, for example, starting with a sample of antibody mRNA that is naturally diverse, first strand cDNA can be produced and digested to provide an original template. A primer can be designed to anneal upstream to a selected complementary determining region (CDR) so that the newly synthesized nucleic acid strand includes the CDR. By way of example, if the target sequence is heavy chain CDR3, the primer may be designed to anneal to the heavy chain framework one (FR1) region. Those skilled in the art will readily envision how to design appropriate primers to anneal to other upstream sites or to reproduce other selected targets within the antibody cDNA based on this disclosure.

The following Examples are provided to illustrate, but not limit, the present invention(s):

Example 1

Amplification of a Repertoire of Ig Kappa Light Chain Variable Genes

First Strand cDNA Synthesis

First strand cDNA to be used as the original template was generated from 2 μg of human peripheral blood lymphocyte (PBL) mRNA with an oligo-dT primer using the SuperScript II First Strand Synthesis Kit (Invitrogen) according to the manufacturer's instructions. The 1$^{st}$ strand cDNA product was purified over a QIAquick spin column (QIAGEN PCR Purification Kit) and eluted in 400 μL of nuclease-free water.

Second Strand Linear Amplification (SSLA) in the Presence of Blocking Oligonucleotide The second strand cDNA reaction contained 5 μL of 1$^{st}$ strand cDNA original template, 0.5 μM primer JMX26VK1a, 0.5 μM blocking oligo CKLNA1, 0.2 mM dNTPs, 5 units of AmpliTaq Gold DNA polymerase (Applied Biosystems), 1×GeneAmp Gold Buffer(15 mM Tris-HCl, pH 8.0, 50 mM KCl), and 1.5 mM MgCl$_2$. The final volume of the reaction was 98 μL. The sequence of primer JMX26VK1a, which hybridizes to the framework 1 region of VK1a genes, was 5' GTC ACT CAC GAA CTC ACG ACT CAC GGA GAG CTC RAC ATC CAG ATG ACC CAG 3' (SEQ ID NO: 1) where R is an equal mixture of A and G. The sequence of the blocking oligo CKLNA1, which hybridizes to the 5' end of the VK constant region, was 5' GAA CTG TGG CTG CAC CAT CTG 3' (SEQ ID NO: 2), where the underlined bases are locked nucleic acid (LNA) nucleotide analogues. After an initial heat denaturation step of 94° C. for 3 minutes, linear amplification of 2$^{nd}$ strand cDNA was carried out for 20 cycles of 94° C. for 15 seconds, 56° C. for 15 seconds, and 68° C. for 1 minute.

Nested Oligo Extension Reaction

After the last cycle of linear amplification, 2 μL of a nested/hairpin oligo designated "JK14TSHP" was added to give a final concentration of 20 μM. The sequence of JK14TSHP was 5' CCT TAG AGT CAC GCT AGC GAT TGA TTG ATT GAT TGATTG TTT GTG ACT CTA AGG TTG GCG CGC CTT CGT TTG ATY TCC ACC TTG GTC C(ps)T(ps)G(ps)P 3' (SEQ ID NO: 3) where Y is an equal mixture of C and T and (ps) are phosphorothioate backbone linkages and P is a 3' propyl group. For nested oligo extension reaction, two cycles of 94° C. for 1 minute, 56° C. for 15 seconds, and 72° C. for 1 minute were performed, followed by a 10 minute incubation at 72° C. to allow complete extension of the hairpin. The reaction products were purified over a QIAquick spin column (QIAgen PCR Purification Kit) and eluted in 50 μL of nuclease-free water.

Analysis of Engineered Template

The efficiency of the nested oligo extension reaction was determined by amplifying the products with either a primer set specific for the engineered product or a primer set that detects all VK1a/JK14 second strand cDNA products (including the engineered product). For specific detection of engineered product, a 10 μL aliquot was amplified for 20 or 25 cycles with primers designated "JMX26" and "TSDP". Primer JMX26 hybridizes to the 5' end of JMX26VK1a, the framework 1 primer used in the second strand cDNA reaction. Primer TSDP hybridizes to the hairpin-loop sequence added to the 3' ends of the second strand cDNAs in the nested oligo extension reaction. The sequence of primer JMX26 was 5' GTC ACT CAC GAA CTC ACG ACT CAC GG 3' (SEQ ID NO: 4). The sequence of primer TSDP was 5' CAC GCT AGC GAT TGA TTG ATT G 3' (SEQ ID NO: 5). For detection of all VK1a/JK14 second strand cDNA products a 10 μL aliquot was amplified for 20 or 25 cycles with primers JMX26 and JK14. The sequence of primer JK 14, which hybridizes to the framework 4 region of JK1 and JK4 genes, was 5' GAG GAG GAG GAG GAG GAG GGC GCG CCT GAT YTC CAC CTT GGT CCC 3' (SEQ ID NO: 6). Both reactions contained 1×GeneAmp Gold Buffer, 1.5 mM MgCl$_2$, 7.5% glycerol, 0.2 mM dNTPs, and 0.5 μM of each primer in a final volume of 50 μL.

The results with primers JMX26 and TSDP demonstrated the successful production of nested oligo and extended VK stem-loop DNA when using SSLA DNA that was blocked specifically with a boundary oligo. Suitable controls showed that when using the nested oligo in the presence of SSLA DNA that was not blocked, only a minimal amount of amplified product was produced. Additional controls without the nested oligo were negative. However, VK1a/JK14 second strand cDNA products were detected equally among all tested samples.

Single Primer Amplification of the Stem-Loop cDNA Template

Conditions that were previously shown to amplify a 352 bp stem-15 bp loop DNA product were as follows: 10 pg of the stem-loop DNA, 2 μM primer, 50 mM Tris-HCl, pH 9.0, 1.5 mM MgCl$_2$, 15 mM (NH$_4$)$_2$SO$_4$, 0.1% Triton X-100, 1.7 M betaine, 0.2 mM dNTPs, and 2.5 units of Z-Taq DNA Polymerase (Takara Shuzo) in a final volume of 50 μL. The thermal cycling conditions were an initial denaturation step of 96° C. for 2.5 minutes, 35 cycles of 96° C. for 30 seconds, 64° C. for 30 seconds, 74° C. for 1.5 minutes, and a final extension step of 74° C. for 10 minutes. Oligonucleotides containing the modified bases 5-methyl-2'-deoxycytidine and/or 2-amino-2'-deoxyadenosine have been shown to prime much more efficiently than unmodified oligonucleotides at primer binding sites located within hairpin structures (Lebedev et al. 1996. *Genetic Analysis: Biomolecular Engineering* 13, 15–21). These modifications work by increasing the melting temperature of the primer, allowing the annealing step of the amplification to be performed at a higher temperature. JMX26 primers containing ten 5-methyl-2'-deoxycytidines or seven 2-amino-2'-deoxyadenosines have been synthesized.

Cloning VK products

Amplified fragments are cloned by Sac I/Asc I into an appropriate expression vector that contains, in frame, the remaining portion of the kappa constant region. Suitable vectors include pRL5 and pRL4 vectors (described in U.S. Provisional Application 60/254,411, the disclosure of which is incorporated herein by reference), fdtetDOG, PHEN1, and pCANTAB5E. Individual kappa clones can be sequenced.

Expanding the Repertoire of VKappa Amplified Products

Further coverage of the VK repertoire is achieved by using the above protocols with a panel of primers for the generation of the second strand DNA. The primers contain JMX26 sequence, a Sac I restriction site, and a region that anneals to 1$^{st}$ strand cDNA in the framework 1 region of human antibody kappa light chain genes. The antibody annealing sequences were derived from the VBase database primers (www.mrc-cpe.cam.ac.uk/imt-doc/publicINTRO.html) which were designed based on the known sequences of human antibodies and are reported to cover the entire human antibody repertoire of kappa light chain genes. Below is a list of suitable primers:

JMX26Vk1a (SEQ ID NO:7)
GTCACTCACGAACTCACGACTCACGGAGAGCTCR-ACATCCAGATGACCCAG
JMX26Vk1b (SEQ ID NO: 8)
GTCACTCACGAACTCACGACTCACGGAGAGCTCG-MCATCCAGTTGACCCAG
JMX26Vk1C (SEQ ID NO: 9)
GTCACTCACGAACTCACGACTCACGGAGAGCTC-GCCATCCRGATGACCCAG
JMX26Vk1d (SEQ ID NO: 10)
GTCACTCACGAACTCACGACTCACGGAGAGCTC-GTCATCTGGATGACCCAG
JMX26Vk2a (SEQ ID NO: 11)
GTCACTCACGAACTCACGACTCACGGAGAGCTC-GATATTGTGATGACCCAG
JMX26Vk2b (SEQ ID NO: 12)
GTCACTCACGAACTCACGACTCACGGAGAGCTCG-ATRTTGTGATGACTCAG
JMX26Vk3a (SEQ ID NO: 13)
GTCACTCACGAACTCACGACTCACGGAGAGCTCG-AAATTGTGTTGACRCAG
JMX26Vk3b (SEQ ID NO: 14)
GTCACTCACGAACTCACGACTCACGGAGAGCTCG-AAATAGTGATGACGCAG
JMX26Vk3c (SEQ ID NO: 15)
GTCACTCACGAACTCACGACTCACGGAGAGCTC-GAAATTGTAATGACACAG
JMX26Vk4a (SEQ ID NO: 16)
GTCACTCACGAACTCACGACTCACGGAGAGCTC-GACATCGTGATGACCCAG
JMX26Vk5a (SEQ ID NO: 17)
GTCACTCACGAACTCACGACTCACGGAGAGCTCG-AAACGACACTCACGCAG
JMX26Vk6a (SEQ ID NO:18)
GTCACTCACGAACTCACGACTCACGGAGAGCTCG-AAATTGTGCTGACTCAG
JMX26 Vk6b (SEQ ID NO: 19)
GTCACTCACGAACTCACGACTCACGGAGAGCTCG-ATGTTGTGATGACACAG

In the foregoing sequences, R is an equal mixture of A and G, M is an equal mixture of A and C, Y is an equal mixture of C and T, W is an equal mixture of A and T, and S is an equal mixture of C and G.

Example 2

Amplification of a Repertoire of IgM or IgG Heavy Chain or Lambda Light Chain Variable Genes Similar protocols are applied to the amplification of both heavy chain and lambda light chain genes. JMX26, or another primer without antibody specific sequences, is used for each of those applications. If JMX26 is used, the second strand DNA is generated with the primers listed below which contain JMX26 sequence, a restriction site (Sac I for lambda, Xho I for heavy chains), and a region that anneals to 1$^{st}$ strand cDNA in the framework 1 region of human antibody lambda light chain or heavy chain genes. The antibody annealing sequences were derived from the VBase database primers (www.mrc-cpe.cam.ac.uk/imt- doc/public/INTRO.html) which were designed based on the known sequences of human antibodies and are reported to cover the entire human antibody repertoire of lambda light chain and heavy chain genes.

Lambda Light Chain Framework 1 Specific Primers:
JMX26VL1a (SEQ ID NO:20)
GTCACTCACGAACTCACGACTCACGGAGAGCTCC-AGTCTGTGCTGACTCAG
JMX26VL1b (SEQ ID NO: 21)
GTCACTCACGAACTCACGACTCACGGAGAGCTC-CAGTCTGTGYTGACGCAG
JMX264VL1C (SEQ ID NO: 22)
GTCACTCACGAACTCACGACTCACGGAGAGCTC-CAGTCTGTCGTGACGCAG
JMX26VL2 (SEQ ID NO: 23)
GTCACTCACGAACTCACGACTCACGGAGAGCTCC-AGTCTGCCCTGACTCAG
JMX26VL3a (SEQ ID NO:24)
GTCACTCACGAACTCACGACTCACGGAGAGCT-CTCCTATGWGCTGACTCAG
JMX26VL3b (SEQ ID NO: 25)
GTCACTCACGAACTCACGACTCACGGAGAGCTC-TCCTATGAGCTGACACAG
JMX26VL3c (SEQ ID NO: 26)
GTCACTCACGAACTCACGACTCACGGAGAGCTCTC-TTCTGAGCTGACTCAG JMX26VL3d (SEQ ID NO: 27)
GTCACTCACGAACTCACGACTCACGGAGAGCTC-
TCCTATGAGCTGATGCAG
JMX26VL4 (SEQ ID NO: 28)
GTCACTCACGAACTCACGACTCACGGAGAGCTCCA-
GCYTGTGCTGACTCAA
JMX26VL5 (SEQ ID NO: 29)
GTCACTCACGAACTCACGACTCACGGAGAGCTCC-
AGSCTGTGCTGACTCAG
JMX26VL6 (SEQ ID NO:30)
GTCACTCACGAACTCACGACTCACGGAGAGCTC-
AATTTTATGCTGACTCAG
JMX26VL7 (SEQ ID NO: 31)
GTCACTCACGAACTCACGACTCACGGAGAGCTCCA-
GRCTGTGGTGACTCAG
JMX26VL8 (SEQ ID NO:32)
GTCACTCACGAACTCACGACTCACGGAGAGCTCCA-
GACTGTGGTGACCCAG
JMX26VL4/9 (SEQ ID NO: 33)
GTCACTCACGAACTCACGACTCACGGAGAGCTC-
CWGCCTGTGCTGACTCAG
JMX26VL10 (SEQ ID NO: 34)
GTCACTCACGAACTCACGACTCACGGAGAGCTCC-
AGGCAGGGCTGACTCAG In the foregoing sequences (and throughout this disclosure), R is an equal mixture of A and G, M is an equal mixture of A and C, Y is an equal mixture of C and T, W is an equal mixture of A and T, and S is an equal mixture of C and G.

Heavy Chain Framework 1 Specific Primers:
JMX24VH1a (SEQ ID NO: 35)
GTCACTCACGAACTCACGACTCACGGActcgagCAGG-
TKCAGCTGGTGCAG
JMX24VH1b (SEQ ID NO: 36)
GTCACTCACGAACTCACGACTCACGGActcgagC-
AGGTCCAGCTTGTGCAG
JMX26VH1c (SEQ ID NO: 37)
GTCACTCACGAACTCACGACTCACGGActcgagSA-
GGTCCAGCTGGTACAG
JMX26VH1d (SEQ ID NO: 38)
GTCACTCACGAACTCACGACTCACGGActcgagC-
ARATGCAGCTGGTGCAG
JMX26VH2a (SEQ ID NO: 39)
GTCACTCACGAACTCACGACTCACGGActcgagC-
AGATCACCTTGAAGGAG
JMX26VH2b (SEQ ID NO: 40)
GTCACTCACGAACTCACGACTCACGGActcgagC-
AGGTCACCTTGARGGAG
JMX26VH3a (SEQ ID NO: 41)
GTCACTCACGAACTCACGACTCACGGActcgagG-
ARGTGCAGCTGGTGGAG
JMX26VH3b (SEQ ID NO: 42)
GTCACTCACGAACTCACGACTCACGGActcgagCA-
GGTGCAGCTGGTGGAG
JMX26VH3c (SEQ ID NO: 43)
GTCACTCACGAACTCACGACTCACGGActcgagG-
AGGTGCAGCTGTTGGAG
JMX26VH4a (SEQ ID NO: 44)
GTCACTCACGAACTCACGACTCACGGActcgagC-
AGSTGCAGCTGCAGGAG
JMX26VH4b (SEQ ID NO: 45)
GTCACTCACGAACTCACGACTCACGGActcgagCA-
GGTGCAGCTACAGCAG
JMX26VH5a (SEQ ID NO: 46)
GTCACTCACGAACTCACGACTCACGGActcgagGAR-
GTGCAGCTGGTGCAG
JMX26VH6a (SEQ ID NO: 47)
GTCACTCACGAACTCACGACTCACGGActcgagC-
AGGTACAGCTGCAGCAG
JMX26VH7a (SEQ ID NO: 48)
GTCACTCACGAACTCACGACTCACGGActcgagC-
AGGTSCAGCTGGTGCAA In the foregoing sequences (and throughout this disclosure), R is an equal mixture of A and G, K is an equal mixture of G and T, and S is an equal mixture of C and G.

Blocking oligos for the constant domain of IgM, IgG, and lambda chains are designed. Essentially, a region downstream of that required for cloning the genes is identified, and within that region, a sequence useful for annealing a blocking oligo is determined. For example with IgG heavy chains, a native Apa I restriction site present in the CH1 domain can be used for cloning. Generally, the boundary oligo is located downstream of that native restriction site. Compatible nested oligos are then designed which contained all the elements described previously.

Once amplified, the lambda light chain genes are cloned as is described above for the kappa light chain genes. Likewise, amplified IgG heavy chain fragments are cloned by Xho I/Apa I into an appropriate expression vector that contains, in frame, the remaining portion of the CHI constant region. Suitable vectors include pRL5, pRL4, fdtetDOG, PHEN1, and pCANTAB5E. Amplified IgM heavy chain fragments are cloned by Xho I/EcoR I into an appropriate expression vector that contains, in frame, the remaining portion of the CH1 constant region. Like the Apa I present natively in IgG genes, the EcoR I site is native to the IgM CH1 domain. Libraries co-expressing both light chains and heavy chains can be screened or selected for Fabs with the desired binding activity.

Example 3

Amplification of a Repertoire of Human IgM Heavy Chain Genes

First Strand cDNA Synthesis

Human peripheral blood lymphocyte (PBL) mRNA was used as the original template to generate the first strand cDNA with ThermoScript RT-PCR System (Invitrogen Life Technologies). In addition to oligo dT primer, a phosphoramidate oligonucleotide (synthesized by Annovis Inc. Aston, PA) was also included in the reverse transcription reaction. The phosphoramidate oligonucleotide serves as a boundary for reverse transcriptase. The first strand cDNA synthesis was terminated at the location where the phosphoramidate oligonucleotide anneals with the mRNA. The phosphoramidate oligonucleotide, PN-1, was designed to anneal with the framework 1 region of immunoglobulin (Ig) heavy chain VH3 genes and PN-VH5 was designed to anneal with the framework 1 region of all the Ig heavy chain genes. A control for first strand cDNA synthesis was also set up by not including the phosphoramidate blocking oligonucleotide. The first strand cDNA product was purified by QIAquick PCR Purification Kit (QIAGEN).

Phosphoramidate Framework 1 Blocking Oligonucleotides for Ig Heavy Chain Genes have the Following Sequences:

```
PN-1   5' GCCTCCCCCAGACTC 3'                    (SEQ ID NO:49)

PN-VH5 5' GCTCCAGACTGCACCAGCTGCAC(C/T)TCGG 3'   (SEQ ID NO:50)
```

Examination of the Blocking Efficiency

The blocking efficiency in first strand cDNA synthesis was examined by PCR reactions using blocking check primers and primer CM1, dNTPs, Advantage-2 DNA polymerase mix (Clontech), the reaction buffer, and the first strand cDNA synthesis product. PCR was performed on a PTC-200 thermal cycler (MJ Research) by heating to 94° C. for 30 seconds and followed by cycles of 94° C. for 15 second, 60° C. for 15 second, and 72° C. for one minute. The blocking check primers were designed to anneal with the leader sequences of Ig heavy chain genes. The sequence of CM1, which hybridizes with the CH1 region of IgM, was 5' GCTCACACTAGTAGGCAGCTCAGCAATCAC 3' (SEQ ID NO: 51). Blocking was analyzed by gel electrophoresis of the PCR products. With appropriate number of cycles, less PCR product was observed from the reverse transcription reactions containing the blocking oligonucleotides than the one does not contain the blocking oligonucleotides, an indication that termination of first strand cDNA synthesis was provided by the hybridization of the blocking oligonucleotides.

The sequences of the blocking check Primers for Ig heavy chain genes have the following sequences:

```
H1/7blck  5' C TGG ACC TGG AGG ATC C 3'      (SEQ ID NO:52)

H1blck2   5' C TGG ACC TGG AGG GTC T 3'      (SEQ ID NO:53)

H1blck3   5' C TGG ATT TGG AGG ATC C 3'      (SEQ ID NO:54)

H2blck    5, GACACACTTTGCTCCACG 3'           (SEQ ID NO:55)

H2blck2   5' GAC ACA CTT TGC TAC ACA 3'      (SEQ ID NO:56)

H3blck    5' TGGGGCTGAGCTGGGTTT 3'           (SEQ ID NO:57)

H3blck2   5' TG GGA CTG AGC TGG ATT T 3'     (SEQ ID NO:58)

H3blck3   5' TT GGG CTG AGC TGG ATT T 3'     (SEQ ID NO:59)

H3blck4   5' TG GGG CTC CGC TGG GTT T 3'     (SEQ ID NO:60)

H3blck5   5' TT GGG CTG AGC TGG CTT T 3'     (SEQ ID NO:61)

H3blck6   5' TT GGA CTG AGC TGG GTT T 3'     (SEQ ID NO:62)

H3blck7   5' TT TGG CTG AGC TGG GTT T 3'     (SEQ ID NO:63)

H4blck    5' AAACACCTGTGGTTCTTC 3'           (SEQ ID NO:64)

H4blck2   5' AAG CAC CTG TGG TTT TTC 3'      (SEQ ID NO:65)

H5blck    5' GGGTCAACCGCCATCCT 3'            (SEQ ID NO:66)

H6blck    5' TCTGTCTCCTTCCTCATC 3'           (SEQ ID NO:67)
```

Second Strand cDNA Synthesis and Nesting Oligonucleotide Extension Reaction:

The purified first strand cDNA synthesis product was used in a nested oligo extension reaction with a hairpin-containing nesting oligonucleotide, dNTPs, Advantage-2 DNA polymerase mix (Clontech), and the reaction buffer. The extension reaction was performed with a GeneAmp PCR System 9700 thermocyler (PE Applied Biosystems). It was heated to 94° C. for 30 seconds and followed by ten cycles of 94° C. for 15 seconds, appropriate annealing temperature for each nesting oligonucleotide for 15 seconds, ramping the temperature to 90° C. at 10% of the normal ramping rate, and 90° C. for 30 seconds. The resulted heavy chain gene should contain a hairpin structure.

Nesting Oligonucleotides for Ig VH1 Heavy Chain genes had the following sequences:

hpVH1-1
5' CTCGAGGGCCCGCGAAAGCGGGCCCTCGAG CAGGTGCAGCTGGTGCAG TCTGGGGCT GAGGT-GAAGAAGCCTG AAG 3' (SEQ ID NO: 68)

hpVH1-2
5' CTCGAGGGCCCGCGAAAGCGGGCCCTC-GAGCAGaTGCAGCTGGTGCAG TCTGGGGCTGAG-GTGAAGAAGaCTAAT 3' (SEQ ID NO: 69)

hpVH 1-3
5' CTCGAGGGCCCGCGAAAGCGGGCCCTCGAG CAG ATG CAG CTG GTG CAG TCT GGGCCT GAG GTG AAG AAG CCT ATT 3' (SEQ ID NO: 70)

hpVH1-4
5' CTCGAGGGCCCGCGAAAGCGGOCCCTC-GAGGAGGTGCAGCTGGTGCAG TCTGGGGCTGAG-GTGAAGAAGCCTGAAG 3' (SEQ ID NO: 71)

Nesting Oligonucleotides for Ig VH2 Heavy Chain Genes:

hpVH2-1

5' CTCGAGGGCCCGCGAAAGCGGGCCCTCGAG CAG ATC ACC TTG AAG GAG TCT GGT CCT ACG CTG GTG AAA CCC ACATAA 3' (SEQ ID NO: 72)

hpVH2-2
5' CTCGAGGGCCCGCGAAAGCGGGCCCTCGAG CAG GTC ACC TTG AAG GAG TCT GGT CCT GYG CTG GTG AAA CCC AC TAA 3' Y:C/T (SEQ ID NO: 73)
Nesting Oligonucleotides for Ig VH3 Heavy Chain Genes:
hpVH3A1
5' CTCGAGGGCCCGCGAAAGCGGGCCCTCGAG GAG GTG CAG CTG GTG GAG TCT GGG GGA GGC TTG GT(C/A) CAG CCT GGGAAA 3' C/A: M(SEQ ID NO: 74)
hpVH3A2
5' CTCGAGGGCCCGCGAAAGCGGGCCCTC-GAGGAGGTGCAGCTGGTGGAGTCTGGG GGAGGC (T/C)TGGT(A/C)AAGCCTGGGAAA 3' (SEQ ID NO: 75)
hpVH3A3
5' CTCGAGGGCCCGCGAAAGCGGGCCCTC-GAGGAGGTGCAGCTGGTGGAGT CTGGGGGAGGT-GTGGTACGGCCTGGGAAA 3' (SEQ ID NO: 76)
hpVH3A4
5' CTCGAGGGCCCGCGAAAGCGGGCCCTC-GAGGAGGTGCAGCTGGTGGAGA CTGGAGGAG-GCTTGATCCAGCCTGGGAAG 3' (SEQ ID NO: 77)
hpVH3A5
5' CTCGAGGGCCCGCGAAAGCGGGCCCTC-GAGGAGGTGCAGCTGGTGGAGT CTGGGG-GAGTCGTGGTACAGCCTGGGAAA 3' (SEQ ID NO: 78)
hpVH3A6
5' CTCGAGGGCCCGCGAAAGCGGGCCCTC-GAGGAGGTGCAGCTGGTGGAGT CT CGGG-GAGTCTTGGTACAGCCTGGGAAA 3' (SEQ ID NO: 79)
hpVH3A7
5' CTCGAGGGCCCGCGAAAGCGGGCCCTCGAG GAG GTG CAG CTG GTG GA G TCT GGG GGA GGC TTG GTA CAG CCT GGCAAA 3' (SEQ ID NO: 80)
hpVH3A8
5' CTCGAGGGCCCGCGAAAGCGGGCCCTCGAG GAG GTG CAG CTG GTG GA G TCT GGG GGA GGC TTG GTC CAG CCT GGAAAA 3' (SEQ ID NO: 81)
hpVH3A9
5' CTCGAGGGCCCGCGAAAGCGGGCCCTCGAG GAG GTG CAG CTG GTG GA G TCT GGG GGA GGC TTA GTT CAG CCT GGGAAA 3' (SEQ ID NO: 82)
hpVH3A10
5' CTCGAGGGCCCGCGAAAGCGGGCCCTCGAG GAG GTG CAG CTG GTG GA G TCT GGG GGA GGC TTG GTA CAG CCA GGGAAA 3' (SEQ ID NO: 83)
ots-hp-VH3b
5 CTCGAGGGCCCGCGAAAGCGGGCCCTC-GAGCAGGTGCAGCTGGTGGAGT CTGGGGGAG-GCGTGGTCCAGCCTGGGTTT 3' (SEQ ID NO: 84)
hp-VH3B2
5' CTCGAGGGCCCGCGAAAGCGGGCCCTC-GAGCAGGTGCAGCTGGTGGAGT CTGGGGGAG-GCTTGGTCAAGCCTGGAAAG 3' (SEQ ID NO: 85)
hpVH3C
5' CTCGAGGGCCCGCGAAAGCGGGCCCTCGAG GAG GTG CAG CTGTTG GA G TCT GGG GGA GGC TTG GTA CAG CCT GGGAAA 3' (SEQ ID NO: 86)
Nesting Oligonucleotides for Ig VH4 Heavy Chain Genes:
hpVH4-1
5' CTCGAGGGCCCGCGAAAGCGGGCCCTCGAG CAG STG CAG CTG CAG GA G TCG GGC CCA GGA CTG GTG AAG CCT T AAA 3' S: C/G (SEQ ID NO: 87)
hpVH4-2
5' CTCGAGGGCCCGCGAAAGCGGGCCCTCGAG CAG CTG CAG CTG CAG GAG TCG GGC TCA GGA CTG GTG AAG CCT T AAA 3' (SEQ ID NO: 88)
hpVH4-3
5' CTCGAGGGCCCGCGAAAGCGGGCCCTCGAG AG GTG CAG CTG CAGCAG TGG GGC GCA GGA CTG TTG AAG CCT T AAT 3' (SEQ ID NO: 89)
Nesting Oligonucleotides for Ig VH5 Heavy Chain Genes:
othpVH52
5' CTCGAGGGCCCGCGAAAGCGGGCCCTC-GAGGAGGTGCAGCTGGTGCAGT CT GGAGCAGAG-GTGAAAAAGCCCGGGGAAAA 3' (SEQ ID NO: 90)
Nesting Oligonucleotides for Ig VH6 Heavy Chain Genes:
hpVH6
5' CTCGAGGGCCCGCGAAAGCGGGCCCTCGAG CAG GTA CAG CTG CAG CAG TCA GGT CCA GGA CTG GTG AAG CCC AAA 3' (SEQ ID NO: 91)
Nesting Oligonucleotides for Ig VH7 Heavy Chain Genes:
hpVH7
5' CTCGAGGGCCCGCGAAAGCGGGCCCTCGAG CAG GTG CAG CTG GTG CAA TCT GGG TCT GAG TTG AAG AAG CCT ATA 3' (SEQ ID NO: 92)
Additional Ig Heavy Chain Nesting Oligonucleotides:
hpVH 3 kb1
5' CTCGAGGGCCCGCGAAAGCGGGCCCTC-GAGGAGGTGCGACTGGTGGAG TCTGGGG-GAGACTTGGTAGAACCGGGGAAG 3' (SEQ ID NO: 93)
hpVH 3 kb2
5' CTCGAGGGCCCGCGAAAGCGGGCCCTC-GAGGAGATGCAACTGGTGGAG TCTGGGGGAGCCT-TCGTCCAGCCGGGGAAG 3' (SEQ ID NO: 94)

Single Primer Amplification of IgM Hairpin-Containing Fd Fragments

Products from the nesting oligo extension reaction (i.e. the engineered template) were amplified using Advantage-2 DNA polymerase mix (Clontech), the reaction buffer, dNTPs, and a single primer named CM3 primer. The sequence for the CM3 primer, which anneals with the CHI region of IgM, was:
5' AGAATTTGACTAGTTGGCAAGAGGCACGT-TCTTTTCTTTGTTGCCGT 3' (SEQ ID NO: 231).

The amplification reaction was performed with a GeneAmp PCR System 9700 thermocyler (PE Applied Biosystems). It was initially heated to 94° C. for 30 seconds and followed by thirty to forty cycles of 94° C. for 15 seconds, appropriate annealing temperature for 15 seconds, ramping the temperature to 90° C. at 10% of the normal ramping speed, and at 90° C. for 30 seconds. The amplified product was examined by electrophoresis to be of the expected size, ~0.7 kb. The amplified fragments were cloned into an expression vector and their sequences were confirmed to be human IgM.

Example 4

Amplification of a Repertoire of Human IgG Heavy Chain Genes from a Donor Immunized with Hepatitis B Surface Antigen First Strand cDNA Synthesis The same protocol as example 3 is employed using mRNA of PBL from a human donor immunized with hepatitis B surface antigen and the phosphoramidate boundary oligonucleotides designed to anneal with the leader sequence of the Ig heavy chain genes. The phosphoramidate leader boundary oligonucleotides for Ig heavy chain genes have the following sequences:

PNVR31d 5'CACCTCACACTGGACACCTTT 3' (SEQ ID NO:95)

PNVH41d 5'CTGGGACAGGACCCATCTGGG 3' (SEQ ID NO:96)

PNVH11d 5'TGGGAGTGGGCACCTGTGG 3' (SEQ ID NO:97)

PNVH21d 5'CTGGGACAAGACCCATGAAG 3' (SEQ ID NO:98)

PNVH51d 5'TCGGAACAGACTCCTTGGAGA 3' (SEQ ID NO:99)

PNVH61d 5'CTGTGACAGGACACCCCATGG 3' (SEQ ID NO:100)

Examination of the Blocking Efficiency

The blocking efficiency in first strand cDNA synthesis is examined by PCR reactions using dNTPs, Advantage-2 DNA polymerase mix (Clontech), the reaction buffer, the first strand cDNA synthesis product, the blocking check primers in Example 3, and the pooled primer mixture of CG1Z, CG2speI, CG3speI, and CG4SpeI. The sequence of primer CG1Z, which hybridized with the CH1 region of IgG1, is 5' GCATGTACTAGTTTTGTCACAA-GATTTGGG 3'. (SEQ ID NO: 101) The sequence of primer CG2speI, which hybridized with the CH1 region of IgG2, is 5' AAGGAAACTAGTTTTGCGCTCAACT-GTCTTGTCCACCT 3'. (SEQ ID NO: 102) The sequence of primer CG3speI, which hybridized with the CHI region of IgG3, is 5' AAGGAAACTAGTGTCAC-CAAGTGGGGTTTTGAGCTC 3'. (SEQ ID NO: 103) The sequence of primer CG4speI, which hybridized with the CHI region of IgG4, is 5' AAGGAAACTAGTACCATAG-GACTCAACTCTCTTG 3'. (SEQ ID NO: 104) PCR is performed on a PTC-200 thermal cycler (MJ Research) by heating to 94° C. for 30 seconds before the following cycle is run, 94° C. for 15 second, 60° C. for 15 second, and 72° C. for one minute. The PCR products were analyzed by gel electrophoresis. With appropriate number of cycles less PCR products were observed from reverse transcription reactions containing the blocking oligonucleotide than the one does not contain blocking oligonucleotide, an indication that termination of first strand cDNA synthesis was provided by hybridization of the leader boundary oligonucleotides.

Second Strand cDNA Synthesis and Nesting Oligonucleotide Extension Reaction:

The same protocol as Example 3 is employed with nesting oligonucleotides having the following sequences are used.

Nesting Oligonucleotides for Ig Heavy Chain VH3 Genes:
HpH3 L1
5'CTCGAGGGCCCGCGAAAGCGGGCCCTC-GAGSAGGTGCAGCTGGTGGAG TCYGAAA 3' where S is an equal mixture of C and G, and Y is an equal mixture of T and C (SEQ ID NO: 105)
HpH3L2
5'CTCGAGGGCCCGCGAAAGCGGGCCCTC-GAGGAGGTGCAG CTG TTG GAG TCT GAAT 3' (SEQ ID NO: 106)
HpH3L3
5'CTCGAGGGCCCGCGAAAGCGGGCCCTCGAG GAG GTG CAG CTG GTG GAG ACT GATA 3' (SEQ ID NO: 107)
HpH3L4
5'CTCGAGGGCCCGCGAAAGCGGGCCCTCGAG GAG GTG CAG CTG GTG GAG TCT CAAA 3' (SEQ ID NO: 108)
Nesting Oligonucleotides for Ig Heavy Chain VH4 Genes:
HpH4L1
5'CTCGAGGGCCCGCGAAAGCGGGCCCTCGAG CAG STG CAG CTG CAG GAG TCG GAAA 3' where S is an equal mixture of C and G (SEQ ID NO: 109)
HpH4L2
5 CTCGAGGGCCCGCGAAAGCGGGCCCTCGAG CAG CTG CAG CTG CAG GAG TCC AAA 3' (SEQ ID NO: 110)
HpH4L3
5' CTCGAGGGCCCGCGAAAGCGGGCCCTCGAG CAG GTG CAG CTA CAG CAG TGG GAAA 3' (SEQ ID NO: 111)
Nesting Oligonucleotides for Ig Heavy Chain VH1 Genes:
HpH1L1
5' CTCGAGGGCCCGCGAAAGCGGGCCCTCGAG CAG GTB CAG CTK GTG CAG AAA 3' where B is an equal mixture of C, G and T and K is an equal mixture of G and T (SEQ ID NO: 112)
HpH1L2
5' CTCGAGGGCCCGCGAAAGCGGGCCCTCGAG SAG GTC CAG CTG GTA CAG AAA 3' where S is an equal mixture of C and G (SEQ ID NO: 113)
HpH1L3
5' CTCGAGGGCCCGCGAAAGCGGGCCCTCGAG CAG ATG CAG CTG GTG CAG AAA 3' (SEQ ID NO: 114)
HpH1L4
5' CTCGAGGGCCCGCGAAAGCGGGCCCTCGAG CAA ATG CAG CTG GTG CAG AAA 3' (SEQ ID NO: 115)
Nesting Oligonucleotides for Ig Heavy Chain VH2 Genes:
HpH2L1
5' CTCGAGGGCCCGCGAAAGCGGGCCCTCGAG CAG ATC ACC TTG AAG GAG TCT AAA 3' (SEQ ID NO: 116)
HpH2L2
5' CTCGAGGGCCCGCGAAAGCGGGCCCTCGAG CAG GTC ACC TTG AAG GAG TCT AAA 3' (SEQ ID NO: 117)
Nesting Oligonucleotides for Ig Heavy Chain VH5 Genes:
HpH5L1
5' CTCGAGGGCCCGCGAAAGCGGGCCCTCGAG GAG GTG CAG CTG GTG CAG AAA 3' (SEQ ID NO: 118)
HpH5L2
5' CTCGAGGGCCCGCGAAAGCGGGCCCTCGAG GAA GTG CAG CTG GTG CAG AAA 3' (SEQ ID NO: 119)
Nesting Oligonucleotides for Ig Heavy Chain VH6 Genes:
HpH6L1
5' CTCGAGGGCCCGCGAAAGCGGGCCCTCGAG CAG GTA CAG CTG CAG CAG TC AAA 3' (SEQ ID NO: 120)
Nesting Oligonucleotides for Ig Heavy Chain VH7 Genes:
HpH7L1
5' CTCGAGGGCCCGCGAAAGCGGGCCCTCGAG CAG GTG CAG CTG GTG CAA TAAA 3' (SEQ ID NO: 121)

Single Primer Amplification of Human IG Heavy Chain Fd Hairpin Containing Fragments The sample protocol as Example 3 was employed using CGIZ, CG2speI, CG3speI, or CG4SpeI as the primer.

Cloning of Amplified IgG Heavy Chain Fd Fragments into a Phage Display Vector

The amplified IgG heavy chain fd hairpin fragments are analyzed by gel electrophoresis. The ~0.7 kb fragment is separated from the primers by cutting out the gel slice and the DNA was collected by electroelution. The eluted DNA was precipitated by ethanol and resuspended in water. It is digested with restriction enzymes XhoI and SpeI and purified by the QIAquick PCR Purification Kit (QIAGEN). The purified XhoI-SpeI fragment is ligated into a suitable plasmid into which the light chain kappa genes amplified from the same donor had previously been cloned. The ligated reaction was transformed into E. coli XL-1 Blue strain {F'proA⁺B⁺lacl_q Δ (lacZ) M15 Tn10/recA1 endA1 gyrA96thi-1 hsdR17 supE44 relA1 lac} by electroporation.
Selection of Human IgG Antibodies that Bind with the Hepatitis B Surface Antigen The XL-1 Blue cells electroporated with the ligation reaction of the phagemid vector and the heavy chain Fd fragments were grown in SOC medium at 37° C. with shaking for one hour. SOC medium is 20 mM glucose in SB medium which contains 1% MOPS hemisodium salt, 3% Bacto Tryptone, and 2% Bacto Yeast Extract. Cells transformed with the plasmid were selected by adding carbenicillin to the culture and they were grown for two hours before infected with a helper phage, VCSM13. After two hours XL-1 Blue cells infected with the helper phage were selected by adding Kanamycin to the culture and the infected cells were amplified overnight by growing at 37° C. with shaking. The next morning the amplified phages were harvested by precipitating with polyethylene glycol (PEG) from the culture supernatant. The PEG precipitated phages were collected by centrifugation. They were resuspended in 1% bovine serum albumin (BSA) in TBS buffer and used in panning for selecting human IgG antibodies that bind with the hepatitis B surface antigen. The resuspended phages were bound with the hepatitis B surface antigen immobilized on the ELISA plate (Costar). The unbound phages were washed off with a washing buffer (0.5% Tween 20 in PBS) and the bound phages were eluted off the plate with a phage elution buffer (0.1M HCl/glycine, pH 2.2, 1 mg/ml BSA) and neutralized with a neutralization buffer (2M Tris Base). The eluted phages were infected with E. coli ER strain {F' proA₊B⁺ lacl^q Δ (lacZ) M15/fhuA2 (ton A)Δ(lac-proAB) supE thi-1 (hsdMS-mcrB) 5}, followed by infection with VCSM13 helper phage. The panning procedure for selecting antibodies bound to hepatitis B surface antigen were repeated three more times.

ELISA Screening of Antibody Clones that Bind with the Hepatitis B Surface Antigen Phages eluted at the fourth round of panning were infected with E. coli Top 10F' strain {F' lac₁^q, Tn10 (Tet^R mcrA Δ(mrr-hsdRMS-mcrBC) Φ8(lacZ Δm15 Δlacx74 deoR recA1 araD13 Δ(ara-leu)7697 galU galK [sL(Str^R) end A1 nupG} and plated on LB-agar plates containing carbenicilin and tetracycline. Individual clones were picked from the plates and grown overnight in SB medium containing carbenicilin and tetracycline. The IgG Fab fragment will be secreted into the culture supernatant. The next morning cells were removed from these cultures by centrifugation and the culture supernatant was screened in ELISA assay for binding to hepatitis B surface antigen immobilized on the ELISA plates. To reduce false positives the ELISA plates were pre-blocked with BSA before binding with the Fab fragments in culture supernatant. The non-binding Fab fragments were washed off by a washing solution (0.05% Tween 20 in PBS). Following the wash, plates were incubated with anti-human IgG (Fab')₂ conjugated with alkaline phosphatase (Pierce) which reacts with p-Nitrophenyl phosphate (Sigma), a chromogenic substrate that shows absorbance at OD405. Positive binding clones were identified by a plate reader (Bio RAD Model 1575) with light absorbance at OD405. Among the ninety-four clones screened there were twenty-eight positive clones.

Characterization of the Hepatitis B Surface Antigen Binding Clones

The IgG heavy chain genes of positive clones from ELISA screening were characterized by DNA sequencing. Plasmid DNA was extracted from the positive clones and sequenced using primers leadVHpAX, NdP, or SeqGZ (Retrogen, San Diego, Calif.). The sequencing primers have the following sequences:
VBVH3A 5' GAGCCGCACGAGCCCCTCGAGGARGT-GCAGCTGGTGGAG 3' (SEQ ID NO: 122)
VBVH 3B 5' GAGCCGCACGAGCCCCTCGAGGAGGT-GCAGCTGGTGGAG 3' (SEQ ID NO: 123)
VBVH 3C₅' GAGCCGCACGAGCCCCTCGAGGAGGT-GCAGCTGTTGGAG 3' (SEQ ID NO: 124)
VBVH 4A 5' GAGCCGCACGAGCCCCTCGAGCAG(CG)TGCAGCTGCAGGAG 3' (SEQ ID NO: 125)
VBVH4B 5' GAGCCGCACGAGCCCCTCGAGCAGGT-GCAGCTACAGCAG 3' (SEQ ID NO: 126)
LeadVHPAX 5' GCGGCGCAGCCGGCGATGGCG 3' (SEQ ID NO: 127)
NdP 5' AGCGTAGTCCGGAACGTCGTACGG (SEQ ID NO: 128)
SeqGZ 5' GAAGTAGTCCTTGACCAG 3' (SEQ ID NO: 129)

The sequences of the variable region of these IgG heavy chain genes from nineteen positive clones are shown in FIG. 5. The great diversity of these IgG heavy chain genes shows this method can efficiently amplify the repertoire of human IgG heavy chain genes from immunized donors.

Example 5

Amplification of a Repertoire of Human Light Chain Kappa Genes

First Strand cDNA Synthesis

The same protocol as example 3 is employed using the phosphoramidate boundary oligonucleotides designed to hybridize with the leader sequence of the kappa light chain genes. The phosphoramidate leader boundary oligonucleotides for kappa light chain genes have the following sequences:
PNK1Id: 5' T GTC ACA TCT GGC ACC TGG 3' (SEQ ID NO: 130)
PNK2Id: 5' TC CCC ACT GGA TCC AGG GAC 3' (SEQ ID NO: 131)
PNK3Id: 5° C. TCC GOT GGT ATC TOG GAG 3' (SEQ ID NO: 132)
PNK4Id: 5' TC CCC GTA GGC ACC AGA GA 3' (SEQ ID NO: 133)
PNK5Id: 5' TC TGC CCT GGT AT C AGA GAT 3' (SEQ ID NO: 134)
PNK6Id: 5' ACC CCT GGA GGC TGG AAC 3' (SEQ ID NO: 135)

Examination of the Blocking Efficiency

The blocking efficiency in first Strand cDNA Synthesis was examined by PCR reactions using blocking check primers and primer CK1DX2, dNTPs, Advantage-2 DNA polymerase mix (Clontech), the reaction buffer, and the first strand cDNA synthesis product. PCR was performed on a PTC-200 thermal cycler (MJ Research) by heating to 94° C. for 30 seconds and followed by cycles of 94° C. for 15 second, 60° C. for 15 second, and 72° C. for one minute. The blocking check primers were designed to anneal with the leader sequences of kappa light chain genes. The sequence of CK1DX2, which hybridizes with the constant region of Kappa light chain, was 5' AGACAGTGAGCGCCGTCTA-GAATTAACACTCTCCCCTGTTGAAGCTCTTTGTGAC GGGCGAACTCAG 3'. (SEQ ID NO: 136) Blocking was analyzed by gel electrophoresis of the PCR products. With appropriate number of cycles less PCR products was observed from reverse transcription reactions containing the blocking oligonucleotide than one that does not contain blocking oligonucleotide, an indication that termination of first strand cDNA synthesis was provided by hybridization of the leader boundary oligonucleotides.

Blocking Check Primers for Kappa Light Chain Genes have the Following Sequences:
K1blck: 5'CTCCGAGGTGCCAGATGT 3' (SEQ ID NO: 137)
K1/2blck2: 5' GCT CAG CTC CTG GGG CT 3' (SEQ ID NO: 138)
K2blck: 5' GTCCCTGGATCCAGTGAG 3' (SEQ ID NO: 139)
K3blck: 5' CTCCCAGATACCACCGGA 3' (SEQ ID NO: 140)
K3blck2: 5' GCG CAG CTT CTC TTC CT 3' (SEQ ID NO: 141)
K3blck3: 5' CAC AGC TTC TTC TTC CTC 3' (SEQ ID NO: 142)
K4blck: 5' ATCTCTGGTGCCTACGGG 3' (SEQ ID NO: 143)
K5blck: 5' ATCTCTGATACCAGGGCA 3' (SEQ ID NO: 144)
K6blck: 5' GTTCCAGCCTCCAGGGGT 3' (SEQ ID NO: 145)

Second Strand cDNA Synthesis and Nesting Oligonucleotide Extension Reaction:
The same protocol as Example 3 is employed using nesting oligonucleotides having the following sequences:
Nesting Oligonucleotides for Light Chain Kappa Vk1:
HpK1L1
5' GAGCTCGGCCCGCGAAAGCGGGCCGAGCTC GMC ATC CAG ATG ACC CAG TCT CCTAA 3' wherein M is an equal mixture of A and C (SEQ ID NO: 146)
HpK1L2
5' GAGCTCGGCCCGCGAAAGCGGGCCGAGCTC AAC ATC CAG ATG ACC CAG TCT CC TAA 3' (SEQ ID NO: 147)
HpK1L3
5' GAGCTCGGCCCGCGAAAGCGGGCCGAGCTC GMC ATC CAG TTG ACC CAG TCT CC TAA 3' wherein M is an equal mixture of A and C (SEQ ID NO: 148)
HpK1L4
5' GAGCTCGGCCCGCGAAAGCGGGCCGAGCTC GCC ATC CGG ATG ACC CAG TCT CCTAT 3' (SEQ ID NO: 149)
HpK1L5
5' GAGCTCGGCCCGCGAAAGCGGGCCGAGCTC GTC ATC TGG ATG ACC CAG TCT CCTAT 3' (SEQ ID NO: 150)
Nesting Oligonucleotides for Light Chain Kappa Vk2:
HpK2L1
5' GAGCTCGGCCCGCGAAAGCGGGCCGAGCTC GAT ATT GTG ATG ACC CAG ACT CTTA 3' (SEQ ID NO: 151)
HpK2L2
5' GAGCTCGGCCCGCGAAAGCGGGCCGAGCTC GAT GTT GTG ATG ACT CAG TCT CCTAA 3' (SEQ ID NO: 152)
HpK2L3
5' GAGCTCGGCCCGCGAAAGCGGGCCGAGCTC GAT ATT GTG ATG ACT CAG TCT CCTAA 3' (SEQ ID NO: 153)
Nesting Oligonucleotides for Light Chain Kappa Vk3:
HpK3L1
5' GAGCTCGGCCCGCGAAAGCGGGCCGAGCTC GAA ATT GTG TTG ACG CAG TCT CCTAA 3' (SEQ ID NO: 154)
HpK3L2
5' GAGCTCGGCCCGCGAAAGCGGGCCGAGCTC GAA ATA GTG ATG ACG CAG TCT CCTAA3' (SEQ ID NO: 155)
HpK3L3
5' GAGCTCGGCCCGCGAAAGCGGGCCGAGCTC GAA ATT GTA ATG ACA CAG TCT CCTAA3' (SEQ ID NO: 156)
Nesting Oligonucleotides for Light Chain Kappa Vk4:
HpK4L1
5' GAGCTCGGCCCGCGAAAGCGGGCCGAGCTC GAC ATC GTG ATG ACC CAG TCT CCTAT3' (SEQ ID NO: 157)
Nesting Oligonucleotides for Light Chain Kappa Vk5:
HpK5L1
5' GAGCTCGGCCCGCGAAAGCGGGCCGAGCTC GAA ACG ACA CTC ACG CAG TCT CCTAA3' (SEQ ID NO: 158)
Nesting Oligonucleotides for Light Chain Kappa Vk6:
HpK6L1
5' GAGCTCGGCCCGCGAAAGCGGGCCGAGCTC GAA ATT GTG CTG ACT CAG TCT CCTAT3' (SEQ ID NO: 159)

Single Primer Amplification of Kappa Hairpin Fragments
The same protocol as Example 3 is employed using CK1DX2 as the primer.

Example 6

Amplification of a Repertoire of Human Light Chain Lambda Genes

First Strand cDNA Synthesis
The same protocol as example 3 is employed using the following phosphoramidate boundary oligonucleotides designed to hybridize with the leader sequence of the lambda light chain genes. The phosphoramidate boundary oligonucleotides for lambda light chain genes have the sequences:
PNL1Id: 5' CTG GGC CCA GGA CCC TGT GC 3' (SEQ ID NO: 160)
PNL2Id: 5' CTG GGC CCA GGA CCC TGT 3'. (SEQ ID NO: 161)
PNL3Id: 5' GA GGC CAC AGA GCC TGT GCA GAG AGT GAG 3' (SEQ ID NO: 162)
PNL4Id1: 5' CAG AGC ACA GAG ACC TGT GGA3' (SEQ ID NO: 163)
PNL4Id2: 5' CTG GGA GAG AGA CCC TGT CCA3' (SEQ ID NO: 164)
PNL5Id1: 5' CTG GGA GAG GGA ACC TGT GCA3' (SEQ ID NO: 165)
PNL6Id1: 5' ATT GGC CCA AGA ACC TGT GCA3' (SEQ ID NO: 166)
PNL7Id1: 5' CTG AGA ATT GGA CCC TGG GCA3' (SEQ ID NO: 167)
PNL8Id1: 5' CTG AGA ATC CAC TCC TGA TCC3' (SEQ ID NO: 168)
PNL9Id1: 5' CTG GGA GAG GGA CCC TGT GAG3' (SEQ ID NO: 169)
PNL10Id1: 5' CTG GAC CAC TGA CAC TGC AGA3' (SEQ ID NO: 170)

Examination of the Blocking Efficiency
The same protocol as example 3 is employed using the following blocking check primers and primer CL2DX2, dNTPs, Advantage-2 DNA polymerase mix (Clontech), the reaction buffer, and the first strand cDNA synthesis product. The blocking check primers have the following sequences:
L1blck: 5' CAC TGY GCA GGG TCC TGG 3' (SEQ ID NO: 171)
L2blck: 5' CAG GGC ACA GGG TCC TGG 3' (SEQ ID NO: 172)
L3blck1: 5' TAC TGC ACA GGA TCC GTG 3' (SEQ ID NO: 173)

L3blck2: 5' CAC TTT ACA GGT TCT GTG 3' (SEQ ID NO: 174)
L3blck3: 5' TTC TGC ACA GTC TCT GAG 3' (SEQ ID NO: 175)
L3blck4: 5' CTC TGC ACA GGC TCT GAG 3' (SEQ ID NO: 176)
L3blck5: 5' CTT TGC TCA GGT TCT GTG 3' (SEQ ID NO: 177)
L3blck6: 5' CAC TGC ACA GGC TCT GTG 3' (SEQ ID NO: 178)
L3blck7: 5' CTC TAC ACA GGC TCT ATT 3' (SEQ ID NO: 179)
L3blck7: 5' CTC TGC ACA GTC TCT GTG 3' (SEQ ID NO: 180)
L4blck1: 5' TTC TCC ACA GGT CTC TGT 3' (SEQ ID NO: 181)
L4blck2: 5' CAC TGG ACA GGG TCT CTC 3' (SEQ ID NO: 182)
L5blck1: 5' CAC TGC ACA GGT TCC CTC 3' (SEQ ID NO: 183)
L6blck: 5' CAC TGC ACA GGT TCT TGG 3' (SEQ ID NO: 184)
L7blck: 5' TGC TGC CCA GGG TCC AAT 3' (SEQ ID NO: 185)
L8blck: 5' TAT GGA TCA GGA GTG GAT 3' (SEQ ID NO: 186)
L9blck: 5' CTC CTC ACA GGG TCC CTC 3' (SEQ ID NO: 187)
L10blck: 5' CAC TCT GCA GTG TCA GTG 3' (SEQ ID NO: 188)
The Sequence of CL2DX2, which hybridizes with the CL region of Lambda genes, has this sequence: 5' AGACAGT-GACGCCGTCTAGAATTATGAACATTCTGTAGG 3' (SEQ ID NO: 189).
Second Strand cDNA Synthesis and Nesting Oligonucleotide Extension Reaction:
The same protocol as Example 3 is employed using the nesting oligonucleotides having the following sequences:
Nesting Oligonucleotides for Lambda Light Chain VL1:
HpL1$_L$1
5' GAGCTCGGCCCGCGAAAGCGGGCCGAGCTC CAG TCT GTG CTG ACT CAG CCA CCAAA 3' (SEQ ID NO: 190)
HpL1L2
5' GAGCTCGGCCCGCGAAAGCGGGCCGAGCTC CAG TCT GTG YTG ACG CAG CCG CCAAA 3' (SEQ ID NO: 191)
Nesting Oligonucleotides for Lambda Light Chain VL2:
5' GAGCTCGGCCCGCGAAAGCGGGCCGAGCTC CAG TCT GCC CTG ACT CAG CCT SAAA3' (SEQ ID NO: 192)
Nesting Oligonucleotides for Lambda Light Chain VL3:
HpL3L1
5' GAGCTCGGCCCGCGAAAGCGGGCCGAGCTC TCC TAT GAG CTG ACT CAG CCA CYAAA3' (SEQ ID NO: 193)
HpL3L2
5' GAGCTCGGCCCGCGAAAGCGGGCCGAGCTC TCC TAT GAG CTG ACA CAG CYA CCAAT 3' (SEQ ID NO: 194)
HpL3L3
5' GAGCTCGGCCCGCGAAAGCGGGCCGAGCTC T CT TCT GAG CTG ACT CAG GAC CCAAA 3' (SEQ ID NO: 195)
HpL3L4
5' GAGCTCGGCCCGCGAAAGCGGGCCGAGCTC TCC TAT GTG CTG ACT CAG CCA CCAAA 3' (SEQ ID NO: 196)
HpL3L5
5' GAGCTCGGCCCGCGAAAGCGGGCCGAGCTC TCC TAT GAG CTG ATG CAG CCA CCAAA 3' (SEQ ID NO: 197)
HpL3L6
5' GAGCTCGGCCCGCGAAAGCGGGCCGAGCTC TCC TAT GAG CTG ACA CAG CCA TCAAA3' (SEQ ID NO: 198)
Nesting Oligonucleotides for Lambda Light Chain VL4:
HpL4L1
5' GAGCTCGGCCCGCGAAAGCGGGCCGAGCTC CTG CCT GTG CTG ACT CAG CCC CCAAA3' (SEQ ID NO: 199)
HpL4L2
5' GAGCTCGGCCCGCGAAAGCGGGCCGAGCTC CAG CCT GTG CTG ACT CAA TCA TCAAA3' (SEQ ID NO: 200)
HpL4L3
5' GAGCTCGGCCCGCGAAAGCGGGCCGAGCTC CAG CTT GTG CTG ACT CAA TCG CCAAA3' (SEQ ID NO: 201)
Nesting Oligonucleotides for Lambda Light Chain VL5:
HpL5L1 5 e. 5b
5' GAGCTCGGCCCGCGAAAGCGGGCCGAGCTC CAG CCT GTG CTG ACT CAG CCA YCAAA3' (SEQ ID NO: 202)
HpL5L2 5c
5' GAGCTCGGCCCGCGAAAGCGGGCCGAGCTC CAG GCT GTG CTG ACT CAG CCG GCAAA3' (SEQ ID NO: 203)
Nesting Oligonucleotides for Lambda Light Chain VL6:
HpL6L1 6a
5' GAGCTCGGCCCGCGAAAGCGGGCCGAGCTC AAT TTT ATG CTG ACT CAG CCC CAAAA3' (SEQ ID NO: 204)
Nesting Oligonucleotides for Lambda Light Chain VL7 and VL8:
HpL7/8L1
5' GAGCTCGGCCCGCGAAAGCGGGCCGAGCTC CAG ACT GTG GTG ACY CAG GAG CCAAA3' (SEQ ID NO: 205)
HpL7L2
5' GAGCTCGGCCCGCGAAAGCGGGCCGAGCTC G CAG GCT GTG GTG ACT CAG GAG CCAAA3' (SEQ ID NO: 206)
Nesting Oligonucleotides for Lambda Light Chain VL9:
HpL9L
5' GAGCTCGGCCCGCGAAAGCGGGCCGAGCTC CAG CCT GTG CTG ACT CAG CCA CCAAA3' (SEQ ID NO: 207)
Nesting Oligonucleotides for Lambda Light Chain VL10:
5' GAGCTCGGCCCGCGAAAGCGGGCCGAGCTC CAG GCA GGG CTG ACT CAG CCA CCAAA3' (SEQ ID NO: 208)
Single Primer Amplification of Lambda Hairpin Containing Fragments
The same protocol as Example 3 is employed using CL2DX2 as the primer.

Example 7

Amplification of a Repertoire of Human IgG Heavy Chain Genes from a Donor Immunized with Hepatitis B Surface Antigen First Strand cDNA Synthesis
The same protocol as example 3 was employed using mRNA of PBL from a human donor immunized with hepatitis B surface antigen as the original template using blocking oligonucleotides that anneal to FR1 of the variable heavy chain.

Examination of the Blocking Efficiency
The same protocol as example 4 was employed.
Second Strand cDNA Synthesis And Nesting Oligonucleotide Extension Reaction:
The same protocol as Example 3 was employed.
Single Primer Amplification of Human IgG Heavy Chain Fd Hairpin Containing Fragments
The sample protocol as Example 4 was employed.
Cloning of Amplified IgG Heavy Chain Fd Fragments into a Phage Display Vector
The sample protocol as Example 4 was employed.
Selection of Human IgG Antibodies that Bind with the Hepatitis B Surface Antigen
The sample protocol as Example 4 was employed.
ELISA Screening of Antibody Clones that Bind with the Hepatitis B Surface Antigen The sample protocol as Example 4 was employed. Among the ninety-four clones screened eighty clones are positive.
Characterization of the Hepatitis B Surface Antigen Binding Clones
The sample protocol as Example 4 was employed. Sequences of the variable regions of the heavy chain genes from fourteen positive clones are listed in FIG. 6. The sequence diversity of these clones and others produced shows this method can efficiently amplify the repertoire of human heavy chain genes from immunized donors.

It will be understood that various modifications may be made to the embodiments described herein. Therefore, the above description should not be construed as limiting, but merely as exemplifications of preferred embodiments. Those skilled in the art will envision other modifications within the scope and spirit of this disclosure.

We claim:

1. A method of amplifying nucleic acid comprising the steps of:
   a) annealing a primer to a template nucleic acid sequence, the primer having a first portion which anneals to the template and a second portion of predetermined sequence;
   b) synthesizing a polynucleotide that anneals to and is complementary to the portion of the template adjacent to the location at which the first portion of the primer anneals to the template, the polynucleotide having a first end and a second end, wherein the first end incorporates the primer,
   c) separating the polynucleotide synthesized in step (b) from the template;
   d) annealing a nested oligonucleotide to the second end of the polynucleotide synthesized in step (b), the nested oligonucleotide having a first portion that anneals to the second end of the polynucleotide, and a second portion having a hairpin structure;
   e) extending the polynucleotide synthesized in step (b) to provide an extended polynucleotide comprising a portion that is complementary to the hairpin structure and a terminal portion that is complementary to the predetermined sequence; and
   f) amplifying the extended polynucleotide using a single primer having the predetermined sequence.

2. A method as in claim 1 further comprising the step of providing a nucleic acid template by annealing a restriction oligonucleotide to a nucleic acid strand to form a double stranded portion and digesting the nucleic acid strand at the double stranded portion.

3. A method as in claim 1 wherein the template encodes an immunoglobulin molecule or fragment thereof.

4. A method as in claim 1 wherein the template is selected from the group consisting of full length or truncated mRNA, DNA and cDNA.

5. A method as in claim 1 wherein the nucleic acid being amplified includes a target sequence encoding a polypeptide.

6. A method as in claim 5 wherein the target sequence encodes an immunoglobulin molecule or fragment thereof.

7. A method as in claim 5 further comprising the step of digesting the extended polynucleotide to isolate the target sequence.

8. A method as in claim 7 further comprising the step of ligating the isolated target sequence into an expression vector.

9. A method as in claim 8 further comprising the steps of transforming a host cell with the expression vector and expressing the polypeptide encoded by the target sequence.

10. A method of amplifying nucleic acid comprising the steps of:
   a) annealing a primer and a boundary oligonucleotide to a template nucleic acid sequence, the primer having a first portion which anneals to the template and a second portion of predetermined sequence;
   b) synthesizing a polynucleotide that anneals to and is complementary to the portion of the template between the location at which the first portion of the primer anneals to the template and the portion of the template to which the boundary oligonucleotide anneals, the polynucleotide having a first end and a second end, wherein the first end incorporates the primer;
   c) separating the polynucleotide synthesized in step (b) from the template;

d) annealing a nested oligonucleotide to the second end of the polynucleotide synthesized in step (b), the nested oligonucleotide having a first portion that anneals to the second end of the polynucleotide and a second portion having a hairpin structure;

e) extending the polynucleotide synthesized in step (b) to provide an extended polynucleotide comprising a portion that is complementary to the hairpin structure and a terminal portion that is complementary to the predetermined sequence; and f) amplifying the extended polynucleotide using a single primer having the predetermined sequence.

11. A method as in claim 10 further comprising the step of providing a nucleic acid template by generating first strand cDNA from mRNA.

12. A method as in claim 10 wherein the template is selected from the group consisting of full length or truncated mRNA, DNA and cDNA.

13. A method as in claim 10 wherein the extended polynucleotide includes a target sequence encoding a polypeptide.

14. A method as in claim 10 wherein the extended polynucleotide encodes an immunoglobulin molecule or fragment thereof.

15. A method as in claim 14 wherein the target sequence encodes an immunoglobulin molecule or fragment thereof.

16. A method as in claim 14 further comprising the step of digesting the extended polynucleotide to isolate the target sequence.

17. A method as in claim 16 further comprising the step of ligating the isolated target sequence into an expression vector.

18. A method as in claim 17 further comprising the steps of transforming a host cell with the expression vector and expressing the polypeptide encoded by the target sequence.

19. A method of amplifying nucleic acid comprising the steps of:

a) annealing an oligo dT primer and a boundary oligonucleotide to an mRNA template;

b) synthesizing a polynucleotide that anneals to and is complementary to the portion of the template between the location at which the first portion of the primer anneals to the template and the portion of the template to which the boundary oligonucleotide anneals, the polynucleotide having a first end and a second end, wherein the first end incorporates the primer;

c) separating the polynucleotide synthesized in step (b) from the template;

d) annealing a nested oligonucleotide to the second end of the polynucleotide synthesized in step (b), the nested oligonucleotide having a first portion that anneals to the second end of the polynucleotide, and a second portion having a hairpin structure;

e) extending the polynucleotide synthesized in step (b) to provide an extended polynucleotide comprising a portion that is complementary to the hairpin structure and a poly A terminal portion; and f) amplifying the extended polynucleotide using a single primer.

20. A method as in claim 19 further comprising the step of providing a nucleic acid template by generating first strand cDNA from mRNA.

21. A method as in claim 19 wherein the template is selected from the group consisting of full length or truncated mRNA, DNA and cDNA.

22. A method as in claim 19 wherein the extended polynucleotide includes a target sequence encoding a polypeptide.

23. A method as in claim 19 wherein the extended polynucleotide encodes an immunoglobulin molecule or fragment thereof.

24. A method as in claim 22 wherein the target sequence encodes an immunoglobulin molecule or fragment thereof.

25. A method as in claim 22 further comprising the step of digesting the extended polynucleotide to isolate the target sequence.

26. A method as in claim 25 further comprising the step of ligating the isolated target sequence into an expression vector.

27. A method as in claim 26 further comprising the steps of transforming a host cell with the expression vector and expressing the polypeptide encoded by the target sequence.

28. A method of amplifying a nucleic acid strand comprising the steps of:

a) providing a nucleic acid strand having i) a predetermined sequence engineered onto a first end thereof, ii) a sequence complementary to the predetermined sequence, and iii) a hairpin structure therebetween; and b) contacting the engineered nucleic acid strand with a primer containing at least a portion of the predetermined sequence in the presence of a polymerase and nucleotides under conditions suitable for polymerization of the nucleotides, thereby producing a complementary nucleic acid strand.

29. A method as in claim 28 further comprising the steps of:

digesting the complementary nucleic acid strand to isolate a target nucleic acid sequence contained therein;

ligating the target nucleic acid sequence into an expression vector;

transforming a host organism with the expression vector; and expressing a polypeptide or protein encoded by the target sequence.

30. A method of amplifying a family of related nucleic acid sequences to build a complex library of polypeptides encoded by the sequences, the method comprising:

a) annealing a primer to a family of related nucleic acid sequence templates, the primer having a first portion which anneals to the templates and a second portion of predetermined sequence;

b) synthesizing polynucleotides that anneal to and are complementary to the portion of the templates adjacent to the location at which the first portion of the primer anneals to the templates, the polynucleotides having a first end and a second end, wherein the first end incorporates the primer;

c) separating the polynucleotides synthesized in step (b) from the templates;

d) annealing a nested oligonucleotide to the second end of the polynucleotides synthesized in step (b), the nested oligonucleotide having a first portion that anneals to the second end of the polynucleotides, and a second portion having a hairpin structure;

e) extending the polynucleotides synthesized in step (b) to provide an extended polynucleotide comprising a portion that is complementary to the hairpin structure and a terminal portion that is complementary to the predetermined sequence; and f) amplifying the extended polynucleotides using a single primer having the predetermined sequence.

31. A method as in claim 1, wherein steps a), b) and c) are repeated from 15 to 25 times prior to annealing the nested oligonucleotide.

32. A method as in claim 10, wherein steps a), b) and c) are repeated from 15 to 25 times prior to annealing the nested oligonucleotide.

33. A method as in claim 19, wherein steps a), b) and c) are repeated from 15 to 25 times prior to annealing the nested oligonucleotide.

34. A method as in claim 30, wherein steps a), b) and c) are repeated from 15 to 25 times prior to annealing the nested oligonucleotide.

35. A method as in claim 1 wherein the first end of the polynucleotide is the 5' end.

36. A method as in claim 1 wherein the first end of the polynucleotide is the 5' end.

37. A method as in claim 19 wherein the first end of the polynucleotide is the 5' end.

38. A method as in claim 1 wherein the first end of the nucleic acid strand is the 5' end.

* * * * *

SEQUENCE LISTING

```
<160> NUMBER OF SEQ ID NOS: 231

<210> SEQ ID NO 1
<211> LENGTH: 51
<212> TYPE: DNA
<213> ORGANISM: artificial sequence
<220> FEATURE:
<223> OTHER INFORMATION: primer

<400> SEQUENCE: 1
gtcactcacg aactcacgac tcacggagag ctcracatcc agatgaccca g         51

<210> SEQ ID NO 2
<211> LENGTH: 21
<212> TYPE: DNA
<213> ORGANISM: artificial sequence
<220> FEATURE:
<223> OTHER INFORMATION: blocking oligonucleotide

<400> SEQUENCE: 2
gaactgtggc tgcaccatct g                                          21

<210> SEQ ID NO 3
<211> LENGTH: 93
<212> TYPE: DNA
<213> ORGANISM: artificial sequence
<220> FEATURE:
<223> OTHER INFORMATION: nested/hairpin oligonucleotide
<220> FEATURE:
<221> NAME/KEY: misc_feature
<222> LOCATION: (89)..(89)
<223> OTHER INFORMATION: n is c with a phosphorothionate backbone
      linkage
<220> FEATURE:
<221> NAME/KEY: misc_feature
<222> LOCATION: (91)..(91)
<223> OTHER INFORMATION: n is t with a phosphorothionate backbone
      linkage
<220> FEATURE:
<221> NAME/KEY: misc_feature
<222> LOCATION: (93)..(93)
<223> OTHER INFORMATION: n is g with a phosphorothionate backbone
      linkage and a terminal propyl group

<400> SEQUENCE: 3
ccttagagtc acgctagcga ttgattgatt gattgattgt ttgtgactct aaggttggcg    60
cgccttcgtt tgatytccac cttggtccnt ngn                              93
```

```
<210> SEQ ID NO 4
<211> LENGTH: 26
<212> TYPE: DNA
<213> ORGANISM: artificial sequence
<220> FEATURE:
<223> OTHER INFORMATION: primer

<400> SEQUENCE: 4
gtcactcacg aactcacgac tcacgg                                    26

<210> SEQ ID NO 5
<211> LENGTH: 22
<212> TYPE: DNA
<213> ORGANISM: artificial sequence
<220> FEATURE:
<223> OTHER INFORMATION: primer

<400> SEQUENCE: 5
cacgctagcg attgattgat tg                                        22

<210> SEQ ID NO 6
<211> LENGTH: 45
<212> TYPE: DNA
<213> ORGANISM: artificial sequence
<220> FEATURE:
<223> OTHER INFORMATION: primer

<400> SEQUENCE: 6
gaggaggagg aggaggaggg cgcgcctgat ytccaccttg gtccc               45

<210> SEQ ID NO 7
<211> LENGTH: 51
<212> TYPE: DNA
<213> ORGANISM: artificial sequence
<220> FEATURE:
<223> OTHER INFORMATION: primer

<400> SEQUENCE: 7
gtcactcacg aactcacgac tcacggagag ctcracatcc agatgaccca g         51

<210> SEQ ID NO 8
<211> LENGTH: 51
<212> TYPE: DNA
<213> ORGANISM: artificial sequence
<220> FEATURE:
<223> OTHER INFORMATION: primer

<400> SEQUENCE: 8
gtcactcacg aactcacgac tcacggagag ctcgmcatcc agttgaccca g         51

<210> SEQ ID NO 9
<211> LENGTH: 51
<212> TYPE: DNA
<213> ORGANISM: artificial sequence
<220> FEATURE:
<223> OTHER INFORMATION: primer

<400> SEQUENCE: 9
gtcactcacg aactcacgac tcacggagag ctcgccatcc rgatgaccca g         51

<210> SEQ ID NO 10
<211> LENGTH: 51
<212> TYPE: DNA
<213> ORGANISM: artificial sequence
<220> FEATURE:
<223> OTHER INFORMATION: primer
```

```
<400> SEQUENCE: 10
gtcactcacg aactcacgac tcacggagag ctcgtcatct ggatgaccca g          51

<210> SEQ ID NO 11
<211> LENGTH: 51
<212> TYPE: DNA
<213> ORGANISM: artificial sequence
<220> FEATURE:
<223> OTHER INFORMATION: primer

<400> SEQUENCE: 11
gtcactcacg aactcacgac tcacggagag ctcgatattg tgatgaccca g          51

<210> SEQ ID NO 12
<211> LENGTH: 51
<212> TYPE: DNA
<213> ORGANISM: artificial sequence
<220> FEATURE:
<223> OTHER INFORMATION: primer

<400> SEQUENCE: 12
gtcactcacg aactcacgac tcacggagag ctcgatrttg tgatgactca g          51

<210> SEQ ID NO 13
<211> LENGTH: 51
<212> TYPE: DNA
<213> ORGANISM: artificial sequence
<220> FEATURE:
<223> OTHER INFORMATION: primer

<400> SEQUENCE: 13
gtcactcacg aactcacgac tcacggagag ctcgaaattg tgttgacrca g          51

<210> SEQ ID NO 14
<211> LENGTH: 51
<212> TYPE: DNA
<213> ORGANISM: artificial sequence
<220> FEATURE:
<223> OTHER INFORMATION: primer

<400> SEQUENCE: 14
gtcactcacg aactcacgac tcacggagag ctcgaaatag tgatgacgca g          51

<210> SEQ ID NO 15
<211> LENGTH: 51
<212> TYPE: DNA
<213> ORGANISM: artificial sequence
<220> FEATURE:
<223> OTHER INFORMATION: primer

<400> SEQUENCE: 15
gtcactcacg aactcacgac tcacggagag ctcgaaattg taatgacaca g          51

<210> SEQ ID NO 16
<211> LENGTH: 51
<212> TYPE: DNA
<213> ORGANISM: artificial sequence
<220> FEATURE:
<223> OTHER INFORMATION: primer

<400> SEQUENCE: 16
gtcactcacg aactcacgac tcacggagag ctcgacatcg tgatgaccca g          51

<210> SEQ ID NO 17
<211> LENGTH: 51
```

```
<212> TYPE: DNA
<213> ORGANISM: artificial sequence
<220> FEATURE:
<223> OTHER INFORMATION: primer

<400> SEQUENCE: 17
gtcactcacg aactcacgac tcacggagag ctcgaaacga cactcacgca g        51

<210> SEQ ID NO 18
<211> LENGTH: 51
<212> TYPE: DNA
<213> ORGANISM: artificial sequence
<220> FEATURE:
<223> OTHER INFORMATION: primer

<400> SEQUENCE: 18
gtcactcacg aactcacgac tcacggagag ctcgaaattg tgctgactca g        51

<210> SEQ ID NO 19
<211> LENGTH: 51
<212> TYPE: DNA
<213> ORGANISM: artificial sequence
<220> FEATURE:
<223> OTHER INFORMATION: primer

<400> SEQUENCE: 19
gtcactcacg aactcacgac tcacggagag ctcgatgttg tgatgacaca g        51

<210> SEQ ID NO 20
<211> LENGTH: 51
<212> TYPE: DNA
<213> ORGANISM: artificial sequence
<220> FEATURE:
<223> OTHER INFORMATION: primer

<400> SEQUENCE: 20
gtcactcacg aactcacgac tcacggagag ctccagtctg tgctgactca g        51

<210> SEQ ID NO 21
<211> LENGTH: 51
<212> TYPE: DNA
<213> ORGANISM: artificial sequence
<220> FEATURE:
<223> OTHER INFORMATION: primer

<400> SEQUENCE: 21
gtcactcacg aactcacgac tcacggagag ctccagtctg tgytgacgca g        51

<210> SEQ ID NO 22
<211> LENGTH: 51
<212> TYPE: DNA
<213> ORGANISM: artificial sequence
<220> FEATURE:
<223> OTHER INFORMATION: primer

<400> SEQUENCE: 22
gtcactcacg aactcacgac tcacggagag ctccagtctg tcgtgacgca g        51

<210> SEQ ID NO 23
<211> LENGTH: 51
<212> TYPE: DNA
<213> ORGANISM: artificial sequence
<220> FEATURE:
<223> OTHER INFORMATION: primer

<400> SEQUENCE: 23
```

```
gtcactcacg aactcacgac tcacggagag ctccagtctg ccctgactca g       51
```

<210> SEQ ID NO 24
<211> LENGTH: 51
<212> TYPE: DNA
<213> ORGANISM: artificial sequence
<220> FEATURE:
<223> OTHER INFORMATION: primer

<400> SEQUENCE: 24

```
gtcactcacg aactcacgac tcacggagag ctctcctatg wgctgactca g       51
```

<210> SEQ ID NO 25
<211> LENGTH: 51
<212> TYPE: DNA
<213> ORGANISM: artificial sequence
<220> FEATURE:
<223> OTHER INFORMATION: primer

<400> SEQUENCE: 25

```
gtcactcacg aactcacgac tcacggagag ctctcctatg agctgacaca g       51
```

<210> SEQ ID NO 26
<211> LENGTH: 51
<212> TYPE: DNA
<213> ORGANISM: artificial sequence
<220> FEATURE:
<223> OTHER INFORMATION: primer

<400> SEQUENCE: 26

```
gtcactcacg aactcacgac tcacggagag ctctcttctg agctgactca g       51
```

<210> SEQ ID NO 27
<211> LENGTH: 51
<212> TYPE: DNA
<213> ORGANISM: artificial sequence
<220> FEATURE:
<223> OTHER INFORMATION: primer

<400> SEQUENCE: 27

```
gtcactcacg aactcacgac tcacggagag ctctcctatg agctgatgca g       51
```

<210> SEQ ID NO 28
<211> LENGTH: 51
<212> TYPE: DNA
<213> ORGANISM: artificial sequence
<220> FEATURE:
<223> OTHER INFORMATION: primer

<400> SEQUENCE: 28

```
gtcactcacg aactcacgac tcacggagag ctccagcytg tgctgactca a       51
```

<210> SEQ ID NO 29
<211> LENGTH: 51
<212> TYPE: DNA
<213> ORGANISM: artificial sequence
<220> FEATURE:
<223> OTHER INFORMATION: primer

<400> SEQUENCE: 29

```
gtcactcacg aactcacgac tcacggagag ctccagsctg tgctgactca g       51
```

<210> SEQ ID NO 30
<211> LENGTH: 51
<212> TYPE: DNA
<213> ORGANISM: artificial sequence

```
<220> FEATURE:
<223> OTHER INFORMATION: primer

<400> SEQUENCE: 30
gtcactcacg aactcacgac tcacggagag ctcaatttta tgctgactca g      51

<210> SEQ ID NO 31
<211> LENGTH: 51
<212> TYPE: DNA
<213> ORGANISM: artificial sequence
<220> FEATURE:
<223> OTHER INFORMATION: primer

<400> SEQUENCE: 31
gtcactcacg aactcacgac tcacggagag ctccagrctg tggtgactca g      51

<210> SEQ ID NO 32
<211> LENGTH: 51
<212> TYPE: DNA
<213> ORGANISM: artificial sequence
<220> FEATURE:
<223> OTHER INFORMATION: primer

<400> SEQUENCE: 32
gtcactcacg aactcacgac tcacggagag ctccagactg tggtgaccca g      51

<210> SEQ ID NO 33
<211> LENGTH: 51
<212> TYPE: DNA
<213> ORGANISM: artificial sequence
<220> FEATURE:
<223> OTHER INFORMATION: primer

<400> SEQUENCE: 33
gtcactcacg aactcacgac tcacggagag ctccwgcctg tgctgactca g      51

<210> SEQ ID NO 34
<211> LENGTH: 51
<212> TYPE: DNA
<213> ORGANISM: artificial sequence
<220> FEATURE:
<223> OTHER INFORMATION: primer

<400> SEQUENCE: 34
gtcactcacg aactcacgac tcacggagag ctccaggcag gctgactca g       51

<210> SEQ ID NO 35
<211> LENGTH: 51
<212> TYPE: DNA
<213> ORGANISM: artificial sequence
<220> FEATURE:
<223> OTHER INFORMATION: primer

<400> SEQUENCE: 35
gtcactcacg aactcacgac tcacggactc gagcaggtkc agctggtgca g      51

<210> SEQ ID NO 36
<211> LENGTH: 51
<212> TYPE: DNA
<213> ORGANISM: artificial sequence
<220> FEATURE:
<223> OTHER INFORMATION: primer

<400> SEQUENCE: 36
gtcactcacg aactcacgac tcacggactc gagcaggtcc agcttgtgca g      51
```

<210> SEQ ID NO 37
<211> LENGTH: 51
<212> TYPE: DNA
<213> ORGANISM: artificial sequence
<220> FEATURE:
<223> OTHER INFORMATION: primer

<400> SEQUENCE: 37
gtcactcacg aactcacgac tcacggactc gagsaggtcc agctggtaca g        51

<210> SEQ ID NO 38
<211> LENGTH: 51
<212> TYPE: DNA
<213> ORGANISM: artificial sequence
<220> FEATURE:
<223> OTHER INFORMATION: primer

<400> SEQUENCE: 38
gtcactcacg aactcacgac tcacggactc gagcaratgc agctggtgca g        51

<210> SEQ ID NO 39
<211> LENGTH: 51
<212> TYPE: DNA
<213> ORGANISM: artificial sequence
<220> FEATURE:
<223> OTHER INFORMATION: primer

<400> SEQUENCE: 39
gtcactcacg aactcacgac tcacggactc gagcagatca ccttgaagga g        51

<210> SEQ ID NO 40
<211> LENGTH: 51
<212> TYPE: DNA
<213> ORGANISM: artificial sequence
<220> FEATURE:
<223> OTHER INFORMATION: primer

<400> SEQUENCE: 40
gtcactcacg aactcacgac tcacggactc gagcaggtca ccttgargga g        51

<210> SEQ ID NO 41
<211> LENGTH: 51
<212> TYPE: DNA
<213> ORGANISM: artificial sequence
<220> FEATURE:
<223> OTHER INFORMATION: primer

<400> SEQUENCE: 41
gtcactcacg aactcacgac tcacggactc gaggargtgc agctggtgga g        51

<210> SEQ ID NO 42
<211> LENGTH: 51
<212> TYPE: DNA
<213> ORGANISM: artificial sequence
<220> FEATURE:
<223> OTHER INFORMATION: primer

<400> SEQUENCE: 42
gtcactcacg aactcacgac tcacggactc gagcaggtgc agctggtgga g        51

<210> SEQ ID NO 43
<211> LENGTH: 51
<212> TYPE: DNA
<213> ORGANISM: artificial sequence
<220> FEATURE:
<223> OTHER INFORMATION: primer

```
<400> SEQUENCE: 43
gtcactcacg aactcacgac tcacggactc gaggaggtgc agctgttgga g           51

<210> SEQ ID NO 44
<211> LENGTH: 51
<212> TYPE: DNA
<213> ORGANISM: artificial sequence
<220> FEATURE:
<223> OTHER INFORMATION: primer

<400> SEQUENCE: 44
gtcactcacg aactcacgac tcacggactc gagcagstgc agctgcagga g           51

<210> SEQ ID NO 45
<211> LENGTH: 51
<212> TYPE: DNA
<213> ORGANISM: artificial sequence
<220> FEATURE:
<223> OTHER INFORMATION: primer

<400> SEQUENCE: 45
gtcactcacg aactcacgac tcacggactc gagcaggtgc agctacagca g           51

<210> SEQ ID NO 46
<211> LENGTH: 51
<212> TYPE: DNA
<213> ORGANISM: artificial sequence
<220> FEATURE:
<223> OTHER INFORMATION: primer

<400> SEQUENCE: 46
gtcactcacg aactcacgac tcacggactc gaggargtgc agctggtgca g           51

<210> SEQ ID NO 47
<211> LENGTH: 51
<212> TYPE: DNA
<213> ORGANISM: artificial sequence
<220> FEATURE:
<223> OTHER INFORMATION: primer

<400> SEQUENCE: 47
gtcactcacg aactcacgac tcacggactc gagcaggtac agctgcagca g           51

<210> SEQ ID NO 48
<211> LENGTH: 51
<212> TYPE: DNA
<213> ORGANISM: artificial sequence
<220> FEATURE:
<223> OTHER INFORMATION: primer

<400> SEQUENCE: 48
gtcactcacg aactcacgac tcacggactc gagcaggtsc agctggtgca a           51

<210> SEQ ID NO 49
<211> LENGTH: 15
<212> TYPE: DNA
<213> ORGANISM: artificial sequence
<220> FEATURE:
<223> OTHER INFORMATION: blocking oligonucleotide

<400> SEQUENCE: 49 gcctcccca gactc                                                    15

<210> SEQ ID NO 50
```

```
<211> LENGTH: 28
<212> TYPE: DNA
<213> ORGANISM: artificial sequence
<220> FEATURE:
<223> OTHER INFORMATION: blocking oligonucleotide
<220> FEATURE:
<221> NAME/KEY: misc_feature
<222> LOCATION: (24)..(24)
<223> OTHER INFORMATION: n is c or t

<400> SEQUENCE: 50
gctccagact gcaccagctg cacntcgg                                    28

<210> SEQ ID NO 51
<211> LENGTH: 30
<212> TYPE: DNA
<213> ORGANISM: artificial sequence
<220> FEATURE:
<223> OTHER INFORMATION: primer

<400> SEQUENCE: 51
gctcacacta gtaggcagct cagcaatcac                                  30

<210> SEQ ID NO 52
<211> LENGTH: 17
<212> TYPE: DNA
<213> ORGANISM: artificial sequence
<220> FEATURE:
<223> OTHER INFORMATION: primer

<400> SEQUENCE: 52
ctggacctgg aggatcc                                                17

<210> SEQ ID NO 53
<211> LENGTH: 17
<212> TYPE: DNA
<213> ORGANISM: artificial sequence
<220> FEATURE:
<223> OTHER INFORMATION: primer

<400> SEQUENCE: 53
ctggacctgg agggtct                                                17

<210> SEQ ID NO 54
<211> LENGTH: 17
<212> TYPE: DNA
<213> ORGANISM: artificial sequence
<220> FEATURE:
<223> OTHER INFORMATION: primer

<400> SEQUENCE: 54
ctggatttgg aggatcc                                                17

<210> SEQ ID NO 55
<211> LENGTH: 18
<212> TYPE: DNA
<213> ORGANISM: artificial sequence
<220> FEATURE:
<223> OTHER INFORMATION: primer

<400> SEQUENCE: 55
gacacacttt gctccacg                                               18

<210> SEQ ID NO 56
<211> LENGTH: 18
<212> TYPE: DNA
<213> ORGANISM: artificial sequence
```

-continued

```
<220> FEATURE:
<223> OTHER INFORMATION: primer

<400> SEQUENCE: 56
gacacacttt gctacaca                                              18

<210> SEQ ID NO 57
<211> LENGTH: 18
<212> TYPE: DNA
<213> ORGANISM: artificial sequence
<220> FEATURE:
<223> OTHER INFORMATION: primer

<400> SEQUENCE: 57
tggggctgag ctgggttt                                              18

<210> SEQ ID NO 58
<211> LENGTH: 18
<212> TYPE: DNA
<213> ORGANISM: artificial sequence
<220> FEATURE:
<223> OTHER INFORMATION: primer

<400> SEQUENCE: 58
tgggactgag ctggattt                                              18

<210> SEQ ID NO 59
<211> LENGTH: 18
<212> TYPE: DNA
<213> ORGANISM: artificial sequence
<220> FEATURE:
<223> OTHER INFORMATION: primer

<400> SEQUENCE: 59
ttgggctgag ctggattt                                              18

<210> SEQ ID NO 60
<211> LENGTH: 18
<212> TYPE: DNA
<213> ORGANISM: artificial sequence
<220> FEATURE:
<223> OTHER INFORMATION: primer

<400> SEQUENCE: 60
tggggctccg ctgggttt                                              18

<210> SEQ ID NO 61
<211> LENGTH: 18
<212> TYPE: DNA
<213> ORGANISM: artificial sequence
<220> FEATURE:
<223> OTHER INFORMATION: primer

<400> SEQUENCE: 61
ttgggctgag ctggcttt                                              18

<210> SEQ ID NO 62
<211> LENGTH: 18
<212> TYPE: DNA
<213> ORGANISM: artificial sequence
<220> FEATURE:
<223> OTHER INFORMATION: primer

<400> SEQUENCE: 62
ttggactgag ctgggttt                                              18
```

```
<210> SEQ ID NO 63
<211> LENGTH: 18
<212> TYPE: DNA
<213> ORGANISM: artificial sequence
<220> FEATURE:
<223> OTHER INFORMATION: primer

<400> SEQUENCE: 63
tttggctgag ctgggttt                                                 18

<210> SEQ ID NO 64
<211> LENGTH: 18
<212> TYPE: DNA
<213> ORGANISM: artificial sequence
<220> FEATURE:
<223> OTHER INFORMATION: primer

<400> SEQUENCE: 64
aaacacctgt ggttcttc                                                 18

<210> SEQ ID NO 65
<211> LENGTH: 18
<212> TYPE: DNA
<213> ORGANISM: artificial sequence
<220> FEATURE:
<223> OTHER INFORMATION: primer

<400> SEQUENCE: 65
aagcacctgt ggttttc                                                  18

<210> SEQ ID NO 66
<211> LENGTH: 17
<212> TYPE: DNA
<213> ORGANISM: artificial sequence
<220> FEATURE:
<223> OTHER INFORMATION: primer

<400> SEQUENCE: 66
gggtcaaccg ccatcct                                                  17

<210> SEQ ID NO 67
<211> LENGTH: 18
<212> TYPE: DNA
<213> ORGANISM: artificial sequence
<220> FEATURE:
<223> OTHER INFORMATION: primer

<400> SEQUENCE: 67
tctgtctcct tcctcatc                                                 18

<210> SEQ ID NO 68
<211> LENGTH: 76
<212> TYPE: DNA
<213> ORGANISM: artificial sequence
<220> FEATURE:
<223> OTHER INFORMATION: nesting oligonucleotide

<400> SEQUENCE: 68
ctcgagggcc cgcgaaagcg ggccctcgag caggtgcagc tggtgcagtc tggggctgag   60
gtgaagaagc ctgaag                                                   76

<210> SEQ ID NO 69
<211> LENGTH: 75
<212> TYPE: DNA
<213> ORGANISM: artificial sequence
```

```
<220> FEATURE:
<223> OTHER INFORMATION: nesting oligonucleotide

<400> SEQUENCE: 69
ctcgagggcc cgcgaaagcg ggccctcgag cagatgcagc tggtgcagtc tggggctgag      60
gtgaagaaga ctaat                                                       75

<210> SEQ ID NO 70
<211> LENGTH: 75
<212> TYPE: DNA
<213> ORGANISM: artificial sequence
<220> FEATURE:
<223> OTHER INFORMATION: nesting oligonucleotide

<400> SEQUENCE: 70
ctcgagggcc cgcgaaagcg ggccctcgag cagatgcagc tggtgcagtc tgggcctgag      60
gtgaagaagc ctatt                                                       75

<210> SEQ ID NO 71
<211> LENGTH: 76
<212> TYPE: DNA
<213> ORGANISM: artificial sequence
<220> FEATURE:
<223> OTHER INFORMATION: nesting oligonucleotide

<400> SEQUENCE: 71
ctcgagggcc cgcgaaagcg ggccctcgag gaggtgcagc tggtgcagtc tggggctgag      60
gtgaagaagc ctgaag                                                      76

<210> SEQ ID NO 72
<211> LENGTH: 78
<212> TYPE: DNA
<213> ORGANISM: artificial sequence
<220> FEATURE:
<223> OTHER INFORMATION: nesting oligonucleotide

<400> SEQUENCE: 72
ctcgagggcc cgcgaaagcg ggccctcgag cagatcacct tgaaggagtc tggtcctacg      60
ctggtgaaac ccacataa                                                    78

<210> SEQ ID NO 73
<211> LENGTH: 77
<212> TYPE: DNA
<213> ORGANISM: artificial sequence
<220> FEATURE:
<223> OTHER INFORMATION: nesting oligonucleotide

<400> SEQUENCE: 73
ctcgagggcc cgcgaaagcg ggccctcgag caggtcacct tgaaggagtc tggtcctgyg      60
ctggtgaaac ccactaa                                                     77

<210> SEQ ID NO 74
<211> LENGTH: 78
<212> TYPE: DNA
<213> ORGANISM: artificial sequence
<220> FEATURE:
<223> OTHER INFORMATION: nesting oligonucleotide
<220> FEATURE:
<221> NAME/KEY: misc_feature
<222> LOCATION: (66)..(66)
<223> OTHER INFORMATION: n is c or a

<400> SEQUENCE: 74
```

```
ctcgagggcc cgcgaaagcg ggccctcgag gaggtgcagc tggtggagtc tgggggaggc    60
ttggtncagc ctgggaaa                                                   78
```

<210> SEQ ID NO 75
<211> LENGTH: 78
<212> TYPE: DNA
<213> ORGANISM: artificial sequence
<220> FEATURE:
<223> OTHER INFORMATION: nesting oligonucleotide
<220> FEATURE:
<221> NAME/KEY: misc_feature
<222> LOCATION: (61)..(61)
<223> OTHER INFORMATION: n is t or c
<220> FEATURE:
<221> NAME/KEY: misc_feature
<222> LOCATION: (66)..(66)
<223> OTHER INFORMATION: n is a or c

<400> SEQUENCE: 75

```
ctcgagggcc cgcgaaagcg ggccctcgag gaggtgcagc tggtggagtc tgggggaggc    60
ntggtnaagc ctgggaaa                                                   78
```

<210> SEQ ID NO 76
<211> LENGTH: 78
<212> TYPE: DNA
<213> ORGANISM: artificial sequence
<220> FEATURE:
<223> OTHER INFORMATION: nesting oligonucleotide

<400> SEQUENCE: 76

```
ctcgagggcc cgcgaaagcg ggccctcgag gaggtgcagc tggtggagtc tgggggaggt    60
gtggtacggc ctgggaaa                                                   78
```

<210> SEQ ID NO 77
<211> LENGTH: 78
<212> TYPE: DNA
<213> ORGANISM: artificial sequence
<220> FEATURE:
<223> OTHER INFORMATION: nesting oligonucleotide

<400> SEQUENCE: 77

```
ctcgagggcc cgcgaaagcg ggccctcgag gaggtgcagc tggtggagac tggaggaggc    60
ttgatccagc ctgggaag                                                   78
```

<210> SEQ ID NO 78
<211> LENGTH: 78
<212> TYPE: DNA
<213> ORGANISM: artificial sequence
<220> FEATURE:
<223> OTHER INFORMATION: nesting oligonucleotide

<400> SEQUENCE: 78

```
ctcgagggcc cgcgaaagcg ggccctcgag gaggtgcagc tggtggagtc tgggggagtc    60
gtggtacagc ctgggaaa                                                   78
```

<210> SEQ ID NO 79
<211> LENGTH: 78
<212> TYPE: DNA
<213> ORGANISM: artificial sequence
<220> FEATURE:
<223> OTHER INFORMATION: nesting oligonucleotide

<400> SEQUENCE: 79

```
ctcgagggcc cgcgaaagcg ggccctcgag gaggtgcagc tggtggagtc tcggggagtc    60
```
ttggtacagc ctgggaaa                                                   78

<210> SEQ ID NO 80
<211> LENGTH: 78
<212> TYPE: DNA
<213> ORGANISM: artificial sequence
<220> FEATURE:
<223> OTHER INFORMATION: nesting oligonucleotide

<400> SEQUENCE: 80
ctcgagggcc cgcgaaagcg ggccctcgag gaggtgcagc tggtggagtc tgggggaggc    60
ttggtacagc ctggcaaa                                                   78

<210> SEQ ID NO 81
<211> LENGTH: 78
<212> TYPE: DNA
<213> ORGANISM: artificial sequence
<220> FEATURE:
<223> OTHER INFORMATION: nesting oligonucleotide

<400> SEQUENCE: 81
ctcgagggcc cgcgaaagcg ggccctcgag gaggtgcagc tggtggagtc tgggggaggc    60
ttggtccagc ctggaaaa                                                   78

<210> SEQ ID NO 82
<211> LENGTH: 78
<212> TYPE: DNA
<213> ORGANISM: artificial sequence
<220> FEATURE:
<223> OTHER INFORMATION: nesting oligonucleotide

<400> SEQUENCE: 82
ctcgagggcc cgcgaaagcg ggccctcgag gaggtgcagc tggtggagtc tgggggaggc    60
ttagttcagc ctgggaaa                                                   78

<210> SEQ ID NO 83
<211> LENGTH: 78
<212> TYPE: DNA
<213> ORGANISM: artificial sequence
<220> FEATURE:
<223> OTHER INFORMATION: nesting oligonucleotide

<400> SEQUENCE: 83
ctcgagggcc cgcgaaagcg ggccctcgag gaggtgcagc tggtggagtc tgggggaggc    60
ttggtacagc cagggaaa                                                   78

<210> SEQ ID NO 84
<211> LENGTH: 78
<212> TYPE: DNA
<213> ORGANISM: artificial sequence
<220> FEATURE:
<223> OTHER INFORMATION: nesting oligonucleotide

<400> SEQUENCE: 84
ctcgagggcc cgcgaaagcg ggccctcgag caggtgcagc tggtggagtc tgggggaggc    60
gtggtccagc ctgggttt                                                   78

<210> SEQ ID NO 85
<211> LENGTH: 78
<212> TYPE: DNA
<213> ORGANISM: artificial sequence
<220> FEATURE:

<223> OTHER INFORMATION: nesting oligonucleotide

<400> SEQUENCE: 85

```
ctcgagggcc cgcgaaagcg ggccctcgag caggtgcagc tggtggagtc tgggggaggc     60
ttggtcaagc ctggaaag                                                   78
```

<210> SEQ ID NO 86
<211> LENGTH: 78
<212> TYPE: DNA
<213> ORGANISM: artificial sequence
<220> FEATURE:
<223> OTHER INFORMATION: nesting oligonucleotide

<400> SEQUENCE: 86

```
ctcgagggcc cgcgaaagcg ggccctcgag gaggtgcagc tgttggagtc tgggggaggc     60
ttggtacagc ctgggaaa                                                   78
```

<210> SEQ ID NO 87
<211> LENGTH: 76
<212> TYPE: DNA
<213> ORGANISM: artificial sequence
<220> FEATURE:
<223> OTHER INFORMATION: nesting oligonucleotide

<400> SEQUENCE: 87

```
ctcgagggcc cgcgaaagcg ggccctcgag cagstgcagc tgcaggagtc gggcccagga     60
ctggtgaagc cttaaa                                                     76
```

<210> SEQ ID NO 88
<211> LENGTH: 76
<212> TYPE: DNA
<213> ORGANISM: artificial sequence
<220> FEATURE:
<223> OTHER INFORMATION: nesting oligonucleotide

<400> SEQUENCE: 88

```
ctcgagggcc cgcgaaagcg ggccctcgag cagctgcagc tgcaggagtc gggctcagga     60
ctggtgaagc cttaaa                                                     76
```

<210> SEQ ID NO 89
<211> LENGTH: 75
<212> TYPE: DNA
<213> ORGANISM: artificial sequence
<220> FEATURE:
<223> OTHER INFORMATION: nesting oligonucleotide

<400> SEQUENCE: 89

```
ctcgagggcc cgcgaaagcg ggccctcgag aggtgcagct gcagcagtgg ggcgcaggac     60
tgttgaagcc ttaat                                                      75
```

<210> SEQ ID NO 90
<211> LENGTH: 80
<212> TYPE: DNA
<213> ORGANISM: artificial sequence
<220> FEATURE:
<223> OTHER INFORMATION: nesting oligonucleotide

<400> SEQUENCE: 90

```
ctcgagggcc cgcgaaagcg ggccctcgag gaggtgcagc tggtgcagtc tggagcagag     60
gtgaaaaagc ccggggaaaa                                                 80
```

<210> SEQ ID NO 91
<211> LENGTH: 75
<212> TYPE: DNA
<213> ORGANISM: artificial sequence
<220> FEATURE:
<223> OTHER INFORMATION: nesting oligonucleotide

<400> SEQUENCE: 91
ctcgagggcc cgcgaaagcg ggccctcgag caggtacagc tgcagcagtc aggtccagga    60
ctggtgaagc ccaaa                                                    75

<210> SEQ ID NO 92
<211> LENGTH: 75
<212> TYPE: DNA
<213> ORGANISM: artificial sequence
<220> FEATURE:
<223> OTHER INFORMATION: nesting oligonucleotide

<400> SEQUENCE: 92
ctcgagggcc cgcgaaagcg ggccctcgag caggtgcagc tggtgcaatc tgggtctgag    60
ttgaagaagc ctata                                                    75

<210> SEQ ID NO 93
<211> LENGTH: 78
<212> TYPE: DNA
<213> ORGANISM: artificial sequence
<220> FEATURE:
<223> OTHER INFORMATION: nesting oligonucleotide

<400> SEQUENCE: 93
ctcgagggcc cgcgaaagcg ggccctcgag gaggtgcgac tggtggagtc tgggggagac    60
ttggtagaac cggggaag                                                 78

<210> SEQ ID NO 94
<211> LENGTH: 78
<212> TYPE: DNA
<213> ORGANISM: artificial sequence
<220> FEATURE:
<223> OTHER INFORMATION: nesting oligonucleotide

<400> SEQUENCE: 94
ctcgagggcc cgcgaaagcg ggccctcgag gagatgcaac tggtggagtc tgggggagcc    60
ttcgtccagc cggggaag                                                 78

<210> SEQ ID NO 95
<211> LENGTH: 21
<212> TYPE: DNA
<213> ORGANISM: artificial sequence
<220> FEATURE:
<223> OTHER INFORMATION: boundary oligonucleotide

<400> SEQUENCE: 95
cacctcacac tggacaccttt t                                            21

<210> SEQ ID NO 96
<211> LENGTH: 21
<212> TYPE: DNA
<213> ORGANISM: artificial sequence
<220> FEATURE:
<223> OTHER INFORMATION: boundary oligonucleotide

<400> SEQUENCE: 96
ctgggacagg acccatctgg g                                             21

<210> SEQ ID NO 97
<211> LENGTH: 19
<212> TYPE: DNA
<213> ORGANISM: artificial sequence
<220> FEATURE:
<223> OTHER INFORMATION: boundary oligonucleotide

<400> SEQUENCE: 97
tgggagtggg cacctgtgg                                             19

<210> SEQ ID NO 98
<211> LENGTH: 20
<212> TYPE: DNA
<213> ORGANISM: artificial sequence
<220> FEATURE:
<223> OTHER INFORMATION: boundary oligonucleotide

<400> SEQUENCE: 98
ctgggacaag acccatgaag                                            20

<210> SEQ ID NO 99
<211> LENGTH: 21
<212> TYPE: DNA
<213> ORGANISM: artificial sequence
<220> FEATURE:
<223> OTHER INFORMATION: boundary oligonucleotide

<400> SEQUENCE: 99
tcggaacaga ctccttggag a                                          21

<210> SEQ ID NO 100
<211> LENGTH: 21
<212> TYPE: DNA
<213> ORGANISM: artificial sequence
<220> FEATURE:
<223> OTHER INFORMATION: boundary oligonucleotide

<400> SEQUENCE: 100
ctgtgacagg acaccccatg g                                          21

<210> SEQ ID NO 101
<211> LENGTH: 30
<212> TYPE: DNA
<213> ORGANISM: artificial sequence
<220> FEATURE:
<223> OTHER INFORMATION: primer

<400> SEQUENCE: 101
gcatgtacta gttttgtcac aagatttggg                                 30

<210> SEQ ID NO 102
<211> LENGTH: 39
<212> TYPE: DNA
<213> ORGANISM: artificial sequence
<220> FEATURE:
<223> OTHER INFORMATION: primer

<400> SEQUENCE: 102
aaggaaacta gttttgcgct caactgtctt gtccaccttt                      39

<210> SEQ ID NO 103
<211> LENGTH: 36
<212> TYPE: DNA
<213> ORGANISM: artificial sequence
<220> FEATURE:
<223> OTHER INFORMATION: primer -continued

<400> SEQUENCE: 103
aaggaaacta gtgtcaccaa gtggggtttt gagctc    36

<210> SEQ ID NO 104
<211> LENGTH: 37
<212> TYPE: DNA
<213> ORGANISM: artificial sequence
<220> FEATURE:
<223> OTHER INFORMATION: primer

<400> SEQUENCE: 104
aaggaaacta gtaccatatt tggactcaac tctcttg    37

<210> SEQ ID NO 105
<211> LENGTH: 55
<212> TYPE: DNA
<213> ORGANISM: artificial sequence
<220> FEATURE:
<223> OTHER INFORMATION: nesting oligonucleotide

<400> SEQUENCE: 105
ctcgagggcc cgcgaaagcg ggccctcgag saggtgcagc tggtggagtc ygaaa    55

<210> SEQ ID NO 106
<211> LENGTH: 55
<212> TYPE: DNA
<213> ORGANISM: artificial sequence
<220> FEATURE:
<223> OTHER INFORMATION: nesting oligonucleotide

<400> SEQUENCE: 106
ctcgagggcc cgcgaaagcg ggccctcgag gaggtgcagc tgttggagtc tgaat    55

<210> SEQ ID NO 107
<211> LENGTH: 55
<212> TYPE: DNA
<213> ORGANISM: artificial sequence
<220> FEATURE:
<223> OTHER INFORMATION: nesting oligonucleotide

<400> SEQUENCE: 107
ctcgagggcc cgcgaaagcg ggccctcgag gaggtgcagc tggtggagac tgata    55

<210> SEQ ID NO 108
<211> LENGTH: 55
<212> TYPE: DNA
<213> ORGANISM: artificial sequence
<220> FEATURE:
<223> OTHER INFORMATION: nesting oligonucleotide

<400> SEQUENCE: 108
ctcgagggcc cgcgaaagcg ggccctcgag gaggtgcagc tggtggagtc tcaaa    55

<210> SEQ ID NO 109
<211> LENGTH: 55
<212> TYPE: DNA
<213> ORGANISM: artificial sequence
<220> FEATURE:
<223> OTHER INFORMATION: nesting oligonucleotide

<400> SEQUENCE: 109
ctcgagggcc cgcgaaagcg ggccctcgag cagstgcagc tgcaggagtc ggaaa    55

<210> SEQ ID NO 110

```
<211> LENGTH: 54
<212> TYPE: DNA
<213> ORGANISM: artificial sequence
<220> FEATURE:
<223> OTHER INFORMATION: nesting oligonucleotide

<400> SEQUENCE: 110
ctcgagggcc cgcgaaagcg ggccctcgag cagctgcagc tgcaggagtc caaa         54

<210> SEQ ID NO 111
<211> LENGTH: 55
<212> TYPE: DNA
<213> ORGANISM: artificial sequence
<220> FEATURE:
<223> OTHER INFORMATION: nesting oligonucleotide

<400> SEQUENCE: 111
ctcgagggcc cgcgaaagcg ggccctcgag caggtgcagc tacagcagtg ggaaa        55

<210> SEQ ID NO 112
<211> LENGTH: 51
<212> TYPE: DNA
<213> ORGANISM: artificial sequence
<220> FEATURE:
<223> OTHER INFORMATION: nesting oligonucleotide

<400> SEQUENCE: 112
ctcgagggcc cgcgaaagcg ggccctcgag caggtbcagc tkgtgcagaa a            51

<210> SEQ ID NO 113
<211> LENGTH: 51
<212> TYPE: DNA
<213> ORGANISM: artificial sequence
<220> FEATURE:
<223> OTHER INFORMATION: nesting oligonucleotide

<400> SEQUENCE: 113
ctcgagggcc cgcgaaagcg ggccctcgag saggtccagc tggtacagaa a            51

<210> SEQ ID NO 114
<211> LENGTH: 51
<212> TYPE: DNA
<213> ORGANISM: artificial sequence
<220> FEATURE:
<223> OTHER INFORMATION: nesting oligonucleotide

<400> SEQUENCE: 114
ctcgagggcc cgcgaaagcg ggccctcgag cagatgcagc tggtgcagaa a            51

<210> SEQ ID NO 115
<211> LENGTH: 51
<212> TYPE: DNA
<213> ORGANISM: artificial sequence
<220> FEATURE:
<223> OTHER INFORMATION: nesting oligonucleotide

<400> SEQUENCE: 115
ctcgagggcc cgcgaaagcg ggccctcgag caaatgcagc tggtgcagaa a            51

<210> SEQ ID NO 116
<211> LENGTH: 54
<212> TYPE: DNA
<213> ORGANISM: artificial sequence
<220> FEATURE:
<223> OTHER INFORMATION: nesting oligonucleotide

<400> SEQUENCE: 116
```
ctcgagggcc cgcgaaagcg ggccctcgag cagatcacct tgaaggagtc taaa    54

<210> SEQ ID NO 117
<211> LENGTH: 54
<212> TYPE: DNA
<213> ORGANISM: artificial sequence
<220> FEATURE:
<223> OTHER INFORMATION: nesting oligonucleotide

<400> SEQUENCE: 117
ctcgagggcc cgcgaaagcg ggccctcgag caggtcacct tgaaggagtc taaa    54

<210> SEQ ID NO 118
<211> LENGTH: 51
<212> TYPE: DNA
<213> ORGANISM: artificial sequence
<220> FEATURE:
<223> OTHER INFORMATION: nesting oligonucleotide

<400> SEQUENCE: 118
ctcgagggcc cgcgaaagcg ggccctcgag gaggtgcagc tggtgcagaa a    51

<210> SEQ ID NO 119
<211> LENGTH: 51
<212> TYPE: DNA
<213> ORGANISM: artificial sequence
<220> FEATURE:
<223> OTHER INFORMATION: nesting oligonucleotide

<400> SEQUENCE: 119
ctcgagggcc cgcgaaagcg ggccctcgag gaagtgcagc tggtgcagaa a    51

<210> SEQ ID NO 120
<211> LENGTH: 53
<212> TYPE: DNA
<213> ORGANISM: artificial sequence
<220> FEATURE:
<223> OTHER INFORMATION: nesting oligonucleotide

<400> SEQUENCE: 120
ctcgagggcc cgcgaaagcg ggccctcgag caggtacagc tgcagcagtc aaa    53

<210> SEQ ID NO 121
<211> LENGTH: 52
<212> TYPE: DNA
<213> ORGANISM: artificial sequence
<220> FEATURE:
<223> OTHER INFORMATION: nesting oligonucleotide

<400> SEQUENCE: 121
ctcgagggcc cgcgaaagcg ggccctcgag caggtgcagc tggtgcaata aa    52

<210> SEQ ID NO 122
<211> LENGTH: 39
<212> TYPE: DNA
<213> ORGANISM: artificial sequence
<220> FEATURE:
<223> OTHER INFORMATION: primer

<400> SEQUENCE: 122
gagccgcacg agcccctcga ggargtgcag ctggtggag    39

<210> SEQ ID NO 123
<211> LENGTH: 39
<212> TYPE: DNA

```
<213> ORGANISM: artificial sequence
<220> FEATURE:
<223> OTHER INFORMATION: primer

<400> SEQUENCE: 123
gagccgcacg agcccctcga ggaggtgcag ctggtggag                    39

<210> SEQ ID NO 124
<211> LENGTH: 39
<212> TYPE: DNA
<213> ORGANISM: artificial sequence
<220> FEATURE:
<223> OTHER INFORMATION: primer

<400> SEQUENCE: 124
gagccgcacg agcccctcga ggaggtgcag ctgttggag                    39

<210> SEQ ID NO 125
<211> LENGTH: 39
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is c or g

<400> SEQUENCE: 125
gagccgcacg agcccctcga gcagntgcag ctgcaggag                    39

<210> SEQ ID NO 126
<211> LENGTH: 39
<212> TYPE: DNA
<213> ORGANISM: artificial sequence
<220> FEATURE:
<223> OTHER INFORMATION: primer

<400> SEQUENCE: 126
gagccgcacg agcccctcga gcaggtgcag ctacagcag                    39

<210> SEQ ID NO 127
<211> LENGTH: 21
<212> TYPE: DNA
<213> ORGANISM: artificial sequence
<220> FEATURE:
<223> OTHER INFORMATION: primer

<400> SEQUENCE: 127
gcggcgcagc cggcgatggc g                                       21

<210> SEQ ID NO 128
<211> LENGTH: 24
<212> TYPE: DNA
<213> ORGANISM: artificial sequence
<220> FEATURE:
<223> OTHER INFORMATION: primer

<400> SEQUENCE: 128
agcgtagtcc ggaacgtcgt acgg                                    24

<210> SEQ ID NO 129
<211> LENGTH: 18
<212> TYPE: DNA
<213> ORGANISM: artificial sequence
<220> FEATURE:
<223> OTHER INFORMATION: primer
```

```
<400> SEQUENCE: 129
gaagtagtcc ttgaccag                                                    18

<210> SEQ ID NO 130
<211> LENGTH: 19
<212> TYPE: DNA
<213> ORGANISM: artificial sequence
<220> FEATURE:
<223> OTHER INFORMATION: boundary oligonucleotide

<400> SEQUENCE: 130
tgtcacatct ggcacctgg                                                   19

<210> SEQ ID NO 131
<211> LENGTH: 20
<212> TYPE: DNA
<213> ORGANISM: artificial sequence
<220> FEATURE:
<223> OTHER INFORMATION: boundary oligonucleotide

<400> SEQUENCE: 131
tccccactgg atccagggac                                                  20

<210> SEQ ID NO 132
<211> LENGTH: 19
<212> TYPE: DNA
<213> ORGANISM: artificial sequence
<220> FEATURE:
<223> OTHER INFORMATION: boundary oligonucleotide

<400> SEQUENCE: 132
ctccggtggt atctgggag                                                   19

<210> SEQ ID NO 133
<211> LENGTH: 19
<212> TYPE: DNA
<213> ORGANISM: artificial sequence
<220> FEATURE:
<223> OTHER INFORMATION: boundary oligonucleotide

<400> SEQUENCE: 133
tccccgtagg caccagaga                                                   19

<210> SEQ ID NO 134
<211> LENGTH: 20
<212> TYPE: DNA
<213> ORGANISM: artificial sequence
<220> FEATURE:
<223> OTHER INFORMATION: boundary oligonucleotide

<400> SEQUENCE: 134
tctgccctgg tatcagagat                                                  20

<210> SEQ ID NO 135
<211> LENGTH: 19
<212> TYPE: DNA
<213> ORGANISM: artificial sequence
<220> FEATURE:
<223> OTHER INFORMATION: boundary oligonucleotide

<400> SEQUENCE: 135
cacccctgga ggctggaac                                                   19

<210> SEQ ID NO 136
```

```
<211> LENGTH: 67
<212> TYPE: DNA
<213> ORGANISM: artificial sequence
<220> FEATURE:
<223> OTHER INFORMATION: primer

<400> SEQUENCE: 136
agacagtgag cgccgtctag aattaacact ctccctgtt gaagctcttt gtgacgggcg    60
aactcag                                                              67

<210> SEQ ID NO 137
<211> LENGTH: 18
<212> TYPE: DNA
<213> ORGANISM: artificial sequence
<220> FEATURE:
<223> OTHER INFORMATION: primer

<400> SEQUENCE: 137
ctccgaggtg ccagatgt                                                  18

<210> SEQ ID NO 138
<211> LENGTH: 17
<212> TYPE: DNA
<213> ORGANISM: artificial sequence
<220> FEATURE:
<223> OTHER INFORMATION: primer

<400> SEQUENCE: 138
gctcagctcc tggggct                                                   17

<210> SEQ ID NO 139
<211> LENGTH: 18
<212> TYPE: DNA
<213> ORGANISM: artificial sequence
<220> FEATURE:
<223> OTHER INFORMATION: primer

<400> SEQUENCE: 139
gtccctggat ccagtgag                                                  18

<210> SEQ ID NO 140
<211> LENGTH: 18
<212> TYPE: DNA
<213> ORGANISM: artificial sequence
<220> FEATURE:
<223> OTHER INFORMATION: primer

<400> SEQUENCE: 140
ctcccagata ccaccgga                                                  18

<210> SEQ ID NO 141
<211> LENGTH: 17
<212> TYPE: DNA
<213> ORGANISM: artificial sequence
<220> FEATURE:
<223> OTHER INFORMATION: primer

<400> SEQUENCE: 141
gcgcagcttc tcttcct                                                   17

<210> SEQ ID NO 142
<211> LENGTH: 18
<212> TYPE: DNA
<213> ORGANISM: artificial sequence
<220> FEATURE:
<223> OTHER INFORMATION: primer
```

```
<400> SEQUENCE: 142
cacagcttct tcttcctc                                           18

<210> SEQ ID NO 143
<211> LENGTH: 18
<212> TYPE: DNA
<213> ORGANISM: artificial sequence
<220> FEATURE:
<223> OTHER INFORMATION: primer

<400> SEQUENCE: 143
atctctggtg cctacggg                                           18

<210> SEQ ID NO 144
<211> LENGTH: 18
<212> TYPE: DNA
<213> ORGANISM: artificial sequence
<220> FEATURE:
<223> OTHER INFORMATION: primer

<400> SEQUENCE: 144
atctctgata ccagggca                                           18

<210> SEQ ID NO 145
<211> LENGTH: 18
<212> TYPE: DNA
<213> ORGANISM: artificial sequence
<220> FEATURE:
<223> OTHER INFORMATION: primer

<400> SEQUENCE: 145
gttccagcct ccagggt                                            18

<210> SEQ ID NO 146
<211> LENGTH: 56
<212> TYPE: DNA
<213> ORGANISM: artificial sequence
<220> FEATURE:
<223> OTHER INFORMATION: nesting oligonucleotide

<400> SEQUENCE: 146
gagctcggcc cgcgaaagcg ggccgagctc gmcatccaga tgacccagtc tcctaa      56

<210> SEQ ID NO 147
<211> LENGTH: 56
<212> TYPE: DNA
<213> ORGANISM: artificial sequence
<220> FEATURE:
<223> OTHER INFORMATION: nesting oligonucleotide

<400> SEQUENCE: 147
gagctcggcc cgcgaaagcg ggccgagctc aacatccaga tgacccagtc tcctaa      56

<210> SEQ ID NO 148
<211> LENGTH: 56
<212> TYPE: DNA
<213> ORGANISM: artificial sequence
<220> FEATURE:
<223> OTHER INFORMATION: nesting oligonucleotide

<400> SEQUENCE: 148
gagctcggcc cgcgaaagcg ggccgagctc gmcatccagt tgacccagtc tcctaa      56

<210> SEQ ID NO 149
```

```
<211> LENGTH: 56
<212> TYPE: DNA
<213> ORGANISM: artificial sequence
<220> FEATURE:
<223> OTHER INFORMATION: nesting oligonucleotide

<400> SEQUENCE: 149
gagctcggcc cgcgaaagcg ggccgagctc gccatccgga tgacccagtc tcctat        56

<210> SEQ ID NO 150
<211> LENGTH: 56
<212> TYPE: DNA
<213> ORGANISM: artificial sequence
<220> FEATURE:
<223> OTHER INFORMATION: nesting oligonucleotide

<400> SEQUENCE: 150
gagctcggcc cgcgaaagcg ggccgagctc gtcatctgga tgacccagtc tcctat        56

<210> SEQ ID NO 151
<211> LENGTH: 55
<212> TYPE: DNA
<213> ORGANISM: artificial sequence
<220> FEATURE:
<223> OTHER INFORMATION: nesting oligonucleotide

<400> SEQUENCE: 151
gagctcggcc cgcgaaagcg ggccgagctc gatattgtga tgacccagac tctta         55

<210> SEQ ID NO 152
<211> LENGTH: 56
<212> TYPE: DNA
<213> ORGANISM: artificial sequence
<220> FEATURE:
<223> OTHER INFORMATION: nesting oligonucleotide

<400> SEQUENCE: 152
gagctcggcc cgcgaaagcg ggccgagctc gatgttgtga tgactcagtc tcctaa        56

<210> SEQ ID NO 153
<211> LENGTH: 56
<212> TYPE: DNA
<213> ORGANISM: artificial sequence
<220> FEATURE:
<223> OTHER INFORMATION: nesting oligonucleotide

<400> SEQUENCE: 153
gagctcggcc cgcgaaagcg ggccgagctc gatattgtga tgactcagtc tcctaa        56

<210> SEQ ID NO 154
<211> LENGTH: 56
<212> TYPE: DNA
<213> ORGANISM: artificial sequence
<220> FEATURE:
<223> OTHER INFORMATION: nesting oligonucleotide

<400> SEQUENCE: 154
gagctcggcc cgcgaaagcg ggccgagctc gaaattgtgt tgacgcagtc tcctaa        56

<210> SEQ ID NO 155
<211> LENGTH: 56
<212> TYPE: DNA
<213> ORGANISM: artificial sequence
<220> FEATURE:
<223> OTHER INFORMATION: nesting oligonucleotide

<400> SEQUENCE: 155
```

```
gagctcggcc cgcgaaagcg ggccgagctc gaaatagtga tgacgcagtc tcctaa      56
```

<210> SEQ ID NO 156
<211> LENGTH: 56
<212> TYPE: DNA
<213> ORGANISM: artificial sequence
<220> FEATURE:
<223> OTHER INFORMATION: nesting oligonucleotide

<400> SEQUENCE: 156

```
gagctcggcc cgcgaaagcg ggccgagctc gaaattgtaa tgacacagtc tcctaa      56
```

<210> SEQ ID NO 157
<211> LENGTH: 56
<212> TYPE: DNA
<213> ORGANISM: artificial sequence
<220> FEATURE:
<223> OTHER INFORMATION: nesting oligonucleotide

<400> SEQUENCE: 157

```
gagctcggcc cgcgaaagcg ggccgagctc gacatcgtga tgacccagtc tcctat      56
```

<210> SEQ ID NO 158
<211> LENGTH: 56
<212> TYPE: DNA
<213> ORGANISM: artificial sequence
<220> FEATURE:
<223> OTHER INFORMATION: nesting oligonucleotide

<400> SEQUENCE: 158

```
gagctcggcc cgcgaaagcg ggccgagctc gaaacgacac tcacgcagtc tcctaa      56
```

<210> SEQ ID NO 159
<211> LENGTH: 56
<212> TYPE: DNA
<213> ORGANISM: artificial sequence
<220> FEATURE:
<223> OTHER INFORMATION: nesting oligonucleotide

<400> SEQUENCE: 159

```
gagctcggcc cgcgaaagcg ggccgagctc gaaattgtgc tgactcagtc tcctat      56
```

<210> SEQ ID NO 160
<211> LENGTH: 20
<212> TYPE: DNA
<213> ORGANISM: artificial sequence
<220> FEATURE:
<223> OTHER INFORMATION: boundary oligonucleotide

<400> SEQUENCE: 160

```
ctgggcccag gaccctgtgc                                              20
```

<210> SEQ ID NO 161
<211> LENGTH: 18
<212> TYPE: DNA
<213> ORGANISM: artificial sequence
<220> FEATURE:
<223> OTHER INFORMATION: boundary oligonucleotide

<400> SEQUENCE: 161

```
ctgggcccag gaccctgt                                                18
```

<210> SEQ ID NO 162
<211> LENGTH: 29
<212> TYPE: DNA

```
<213> ORGANISM: artificial sequence
<220> FEATURE:
<223> OTHER INFORMATION: boundary oligonucleotide

<400> SEQUENCE: 162
gaggccacag agcctgtgca gagagtgag                                    29

<210> SEQ ID NO 163
<211> LENGTH: 21
<212> TYPE: DNA
<213> ORGANISM: artificial sequence
<220> FEATURE:
<223> OTHER INFORMATION: boundary oligonucleotide

<400> SEQUENCE: 163
cagagcacag agacctgtgg a                                            21

<210> SEQ ID NO 164
<211> LENGTH: 21
<212> TYPE: DNA
<213> ORGANISM: artificial sequence
<220> FEATURE:
<223> OTHER INFORMATION: boundary oligonucleotide

<400> SEQUENCE: 164
ctgggagaga gaccctgtcc a                                            21

<210> SEQ ID NO 165
<211> LENGTH: 21
<212> TYPE: DNA
<213> ORGANISM: artificial sequence
<220> FEATURE:
<223> OTHER INFORMATION: boundary oligonucleotide

<400> SEQUENCE: 165
ctgggagagg gaacctgtgc a                                            21

<210> SEQ ID NO 166
<211> LENGTH: 21
<212> TYPE: DNA
<213> ORGANISM: artificial sequence
<220> FEATURE:
<223> OTHER INFORMATION: boundary oligonucleotide

<400> SEQUENCE: 166
attggcccaa gaacctgtgc a                                            21

<210> SEQ ID NO 167
<211> LENGTH: 21
<212> TYPE: DNA
<213> ORGANISM: artificial sequence
<220> FEATURE:
<223> OTHER INFORMATION: boundary oligonucleotide

<400> SEQUENCE: 167
ctgagaattg gaccctgggc a                                            21

<210> SEQ ID NO 168
<211> LENGTH: 21
<212> TYPE: DNA
<213> ORGANISM: artificial sequence
<220> FEATURE:
<223> OTHER INFORMATION: boundary oligonucleotide

<400> SEQUENCE: 168
ctgagaatcc actcctgatc c                                            21
```

<210> SEQ ID NO 169
<211> LENGTH: 21
<212> TYPE: DNA
<213> ORGANISM: artificial sequence
<220> FEATURE:
<223> OTHER INFORMATION: boundary oligonucleotide

<400> SEQUENCE: 169
ctgggagagg gaccctgtga g                                              21

<210> SEQ ID NO 170
<211> LENGTH: 21
<212> TYPE: DNA
<213> ORGANISM: artificial sequence
<220> FEATURE:
<223> OTHER INFORMATION: boundary oligonucleotide

<400> SEQUENCE: 170
ctggaccact gacactgcag a                                              21

<210> SEQ ID NO 171
<211> LENGTH: 18
<212> TYPE: DNA
<213> ORGANISM: artificial sequence
<220> FEATURE:
<223> OTHER INFORMATION: primer

<400> SEQUENCE: 171
cactgygcag ggtcctgg                                                  18

<210> SEQ ID NO 172
<211> LENGTH: 18
<212> TYPE: DNA
<213> ORGANISM: artificial sequence
<220> FEATURE:
<223> OTHER INFORMATION: primer

<400> SEQUENCE: 172
cagggcacag ggtcctgg                                                  18

<210> SEQ ID NO 173
<211> LENGTH: 18
<212> TYPE: DNA
<213> ORGANISM: artificial sequence
<220> FEATURE:
<223> OTHER INFORMATION: primer

<400> SEQUENCE: 173
tactgcacag gatccgtg                                                  18

<210> SEQ ID NO 174
<211> LENGTH: 18
<212> TYPE: DNA
<213> ORGANISM: artificial sequence
<220> FEATURE:
<223> OTHER INFORMATION: primer

<400> SEQUENCE: 174
cactttacag gttctgtg                                                  18

<210> SEQ ID NO 175
<211> LENGTH: 18
<212> TYPE: DNA
<213> ORGANISM: artificial sequence
<220> FEATURE:

```
<223> OTHER INFORMATION: primer

<400> SEQUENCE: 175
ttctgcacag tctctgag                                                 18

<210> SEQ ID NO 176
<211> LENGTH: 18
<212> TYPE: DNA
<213> ORGANISM: artificial sequence
<220> FEATURE:
<223> OTHER INFORMATION: primer

<400> SEQUENCE: 176
ctctgcacag gctctgag                                                 18

<210> SEQ ID NO 177
<211> LENGTH: 18
<212> TYPE: DNA
<213> ORGANISM: artificial sequence
<220> FEATURE:
<223> OTHER INFORMATION: primer

<400> SEQUENCE: 177
ctttgctcag gttctgtg                                                 18

<210> SEQ ID NO 178
<211> LENGTH: 18
<212> TYPE: DNA
<213> ORGANISM: artificial sequence
<220> FEATURE:
<223> OTHER INFORMATION: primer

<400> SEQUENCE: 178
cactgcacag gctctgtg                                                 18

<210> SEQ ID NO 179
<211> LENGTH: 18
<212> TYPE: DNA
<213> ORGANISM: artificial sequence
<220> FEATURE:
<223> OTHER INFORMATION: primer

<400> SEQUENCE: 179
ctctacacag gctctatt                                                 18

<210> SEQ ID NO 180
<211> LENGTH: 18
<212> TYPE: DNA
<213> ORGANISM: artificial sequence
<220> FEATURE:
<223> OTHER INFORMATION: primer

<400> SEQUENCE: 180
ctctgcacag tctctgtg                                                 18

<210> SEQ ID NO 181
<211> LENGTH: 18
<212> TYPE: DNA
<213> ORGANISM: artificial sequence
<220> FEATURE:
<223> OTHER INFORMATION: primer

<400> SEQUENCE: 181
ttctccacag gtctctgt                                                 18
```

```
<210> SEQ ID NO 182
<211> LENGTH: 18
<212> TYPE: DNA
<213> ORGANISM: artificial sequence
<220> FEATURE:
<223> OTHER INFORMATION: primer

<400> SEQUENCE: 182
cactggacag ggtctctc                                                 18

<210> SEQ ID NO 183
<211> LENGTH: 18
<212> TYPE: DNA
<213> ORGANISM: artificial sequence
<220> FEATURE:
<223> OTHER INFORMATION: primer

<400> SEQUENCE: 183
cactgcacag gttccctc                                                 18

<210> SEQ ID NO 184
<211> LENGTH: 18
<212> TYPE: DNA
<213> ORGANISM: artificial sequence
<220> FEATURE:
<223> OTHER INFORMATION: primer

<400> SEQUENCE: 184
cactgcacag gttcttgg                                                 18

<210> SEQ ID NO 185
<211> LENGTH: 18
<212> TYPE: DNA
<213> ORGANISM: artificial sequence
<220> FEATURE:
<223> OTHER INFORMATION: primer

<400> SEQUENCE: 185
tgctgcccag ggtccaat                                                 18

<210> SEQ ID NO 186
<211> LENGTH: 18
<212> TYPE: DNA
<213> ORGANISM: artificial sequence
<220> FEATURE:
<223> OTHER INFORMATION: primer

<400> SEQUENCE: 186
tatggatcag gagtggat                                                 18

<210> SEQ ID NO 187
<211> LENGTH: 18
<212> TYPE: DNA
<213> ORGANISM: artificial sequence
<220> FEATURE:
<223> OTHER INFORMATION: primer

<400> SEQUENCE: 187
ctcctcacag ggtccctc                                                 18

<210> SEQ ID NO 188
<211> LENGTH: 18
<212> TYPE: DNA
<213> ORGANISM: artificial sequence
<220> FEATURE:
<223> OTHER INFORMATION: primer
```

```
<400> SEQUENCE: 188
cactctgcag tgtcagtg                                              18

<210> SEQ ID NO 189
<211> LENGTH: 39
<212> TYPE: DNA
<213> ORGANISM: artificial sequence
<220> FEATURE:
<223> OTHER INFORMATION: primer

<400> SEQUENCE: 189
agacagtgac gccgtctaga attatgaaca ttctgtagg                       39

<210> SEQ ID NO 190
<211> LENGTH: 56
<212> TYPE: DNA
<213> ORGANISM: artificial sequence
<220> FEATURE:
<223> OTHER INFORMATION: nesting oligonucleotide

<400> SEQUENCE: 190
gagctcggcc cgcgaaagcg ggccgagctc cagtctgtgc tgactcagcc accaaa    56

<210> SEQ ID NO 191
<211> LENGTH: 56
<212> TYPE: DNA
<213> ORGANISM: artificial sequence
<220> FEATURE:
<223> OTHER INFORMATION: nesting oligonucleotide

<400> SEQUENCE: 191
gagctcggcc cgcgaaagcg ggccgagctc cagtctgtgy tgacgcagcc gccaaa    56

<210> SEQ ID NO 192
<211> LENGTH: 55
<212> TYPE: DNA
<213> ORGANISM: artificial sequence
<220> FEATURE:
<223> OTHER INFORMATION: nesting oligonucleotide

<400> SEQUENCE: 192
gagctcggcc cgcgaaagcg ggccgagctc cagtctgccc tgactcagcc tsaaa     55

<210> SEQ ID NO 193
<211> LENGTH: 56
<212> TYPE: DNA
<213> ORGANISM: artificial sequence
<220> FEATURE:
<223> OTHER INFORMATION: nesting oligonucleotide

<400> SEQUENCE: 193
gagctcggcc cgcgaaagcg ggccgagctc tcctatgagc tgactcagcc acyaaa    56

<210> SEQ ID NO 194
<211> LENGTH: 56
<212> TYPE: DNA
<213> ORGANISM: artificial sequence
<220> FEATURE:
<223> OTHER INFORMATION: nesting oligonucleotide

<400> SEQUENCE: 194
gagctcggcc cgcgaaagcg ggccgagctc tcctatgagc tgacacagcy accaat    56

<210> SEQ ID NO 195
<211> LENGTH: 56
```

<210> SEQ ID NO 196
<211> LENGTH: 56
<212> TYPE: DNA
<213> ORGANISM: artificial sequence
<220> FEATURE:
<223> OTHER INFORMATION: nesting oligonucleotide

<400> SEQUENCE: 195
gagctcggcc cgcgaaagcg ggccgagctc tcttctgagc tgactcagga cccaaa    56

<210> SEQ ID NO 196
<211> LENGTH: 56
<212> TYPE: DNA
<213> ORGANISM: artificial sequence
<220> FEATURE:
<223> OTHER INFORMATION: nesting oligonucleotide

<400> SEQUENCE: 196
gagctcggcc cgcgaaagcg ggccgagctc tcctatgtgc tgactcagcc accaaa    56

<210> SEQ ID NO 197
<211> LENGTH: 56
<212> TYPE: DNA
<213> ORGANISM: artificial sequence
<220> FEATURE:
<223> OTHER INFORMATION: nesting oligonucleotide

<400> SEQUENCE: 197
gagctcggcc cgcgaaagcg ggccgagctc tcctatgagc tgatgcagcc accaaa    56

<210> SEQ ID NO 198
<211> LENGTH: 56
<212> TYPE: DNA
<213> ORGANISM: artificial sequence
<220> FEATURE:
<223> OTHER INFORMATION: nesting oligonucleotide

<400> SEQUENCE: 198
gagctcggcc cgcgaaagcg ggccgagctc tcctatgagc tgacacagcc atcaaa    56

<210> SEQ ID NO 199
<211> LENGTH: 56
<212> TYPE: DNA
<213> ORGANISM: artificial sequence
<220> FEATURE:
<223> OTHER INFORMATION: nesting oligonucleotide

<400> SEQUENCE: 199
gagctcggcc cgcgaaagcg ggccgagctc ctgcctgtgc tgactcagcc cccaaa    56

<210> SEQ ID NO 200
<211> LENGTH: 56
<212> TYPE: DNA
<213> ORGANISM: artificial sequence
<220> FEATURE:
<223> OTHER INFORMATION: nesting oligonucleotide

<400> SEQUENCE: 200
gagctcggcc cgcgaaagcg ggccgagctc cagcctgtgc tgactcaatc atcaaa    56

<210> SEQ ID NO 201
<211> LENGTH: 56
<212> TYPE: DNA
<213> ORGANISM: artificial sequence
<220> FEATURE:
<223> OTHER INFORMATION: nesting oligonucleotide

<400> SEQUENCE: 201

```
gagctcggcc cgcgaaagcg ggccgagctc cagcttgtgc tgactcaatc gccaaa     56

<210> SEQ ID NO 202
<211> LENGTH: 56
<212> TYPE: DNA
<213> ORGANISM: artificial sequence
<220> FEATURE:
<223> OTHER INFORMATION: nesting oligonucleotide

<400> SEQUENCE: 202
gagctcggcc cgcgaaagcg ggccgagctc cagcctgtgc tgactcagcc aycaaa     56

<210> SEQ ID NO 203
<211> LENGTH: 56
<212> TYPE: DNA
<213> ORGANISM: artificial sequence
<220> FEATURE:
<223> OTHER INFORMATION: nesting oligonucleotide

<400> SEQUENCE: 203
gagctcggcc cgcgaaagcg ggccgagctc caggctgtgc tgactcagcc ggcaaa     56

<210> SEQ ID NO 204
<211> LENGTH: 56
<212> TYPE: DNA
<213> ORGANISM: artificial sequence
<220> FEATURE:
<223> OTHER INFORMATION: nesting oligonucleotide

<400> SEQUENCE: 204
gagctcggcc cgcgaaagcg ggccgagctc aattttatgc tgactcagcc ccaaaa     56

<210> SEQ ID NO 205
<211> LENGTH: 56
<212> TYPE: DNA
<213> ORGANISM: artificial sequence
<220> FEATURE:
<223> OTHER INFORMATION: nesting oligonucleotide

<400> SEQUENCE: 205
gagctcggcc cgcgaaagcg ggccgagctc cagactgtgg tgacycagga gccaaa     56

<210> SEQ ID NO 206
<211> LENGTH: 57
<212> TYPE: DNA
<213> ORGANISM: artificial sequence
<220> FEATURE:
<223> OTHER INFORMATION: nesting oligonucleotide

<400> SEQUENCE: 206
gagctcggcc cgcgaaagcg ggccgagctc gcaggctgtg gtgactcagg agccaaa    57

<210> SEQ ID NO 207
<211> LENGTH: 56
<212> TYPE: DNA
<213> ORGANISM: artificial sequence
<220> FEATURE:
<223> OTHER INFORMATION: nesting oligonucleotide

<400> SEQUENCE: 207
gagctcggcc cgcgaaagcg ggccgagctc cagcctgtgc tgactcagcc accaaa     56

<210> SEQ ID NO 208
<211> LENGTH: 56
<212> TYPE: DNA
<213> ORGANISM: artificial sequence
```

```
<220> FEATURE:
<223> OTHER INFORMATION: nesting oligonucleotide

<400> SEQUENCE: 208
gagctcggcc cgcgaaagcg ggccgagctc caggcagggc tgactcagcc accaaa      56

<210> SEQ ID NO 209
<211> LENGTH: 115
<212> TYPE: PRT
<213> ORGANISM: artificial sequence
<220> FEATURE:
<223> OTHER INFORMATION: cloned antibody

<400> SEQUENCE: 209
```

| Glu | Ser | Asp | Gly | Ala | Val | Val | Gln | Pro | Gly | Gly | Ser | Leu | Arg | Leu | Ser |
|---|---|---|---|---|---|---|---|---|---|---|---|---|---|---|---|
| 1 | | | | 5 | | | | | 10 | | | | | 15 | |

| Cys | Ala | Ala | Ser | Gly | Phe | Ile | Phe | Asp | Asp | Phe | Ala | Met | His | Trp | Leu |
|---|---|---|---|---|---|---|---|---|---|---|---|---|---|---|---|
| | | | 20 | | | | 25 | | | | 30 | | | | |

| Arg | Gln | Val | Pro | Gly | Lys | Gly | Leu | Gln | Trp | Val | Gly | Leu | Met | Ser | Trp |
|---|---|---|---|---|---|---|---|---|---|---|---|---|---|---|---|
| | | 35 | | | | 40 | | | | | 45 | | | | |

| Asp | Gly | Val | Ser | Ala | Tyr | Tyr | Ala | Asp | Ser | Val | Glu | Gly | Arg | Phe | Thr |
|---|---|---|---|---|---|---|---|---|---|---|---|---|---|---|---|
| | 50 | | | | | 55 | | | | | 60 | | | | |

| Ile | Ser | Arg | Asp | Asn | Lys | Lys | Asn | Ala | Leu | Tyr | Leu | Gln | Met | Asn | Ser |
|---|---|---|---|---|---|---|---|---|---|---|---|---|---|---|---|
| 65 | | | | | 70 | | | | | 75 | | | | | 80 |

| Leu | Gly | Val | Glu | Asp | Thr | Ala | Leu | Tyr | Tyr | Cys | Ala | Lys | Asp | Met | Gly |
|---|---|---|---|---|---|---|---|---|---|---|---|---|---|---|---|
| | | | | 85 | | | | | 90 | | | | | 95 | |

| Gly | Gly | Leu | Arg | Phe | Pro | His | Phe | Trp | Gly | Gln | Gly | Thr | Pro | Val | Thr |
|---|---|---|---|---|---|---|---|---|---|---|---|---|---|---|---|
| | | | 100 | | | | | 105 | | | | | 110 | | |

| Val | Ser | Ala |
|---|---|---|
| | | 115 |

```
<210> SEQ ID NO 210
<211> LENGTH: 110
<212> TYPE: PRT
<213> ORGANISM: artificial sequence
<220> FEATURE:
<223> OTHER INFORMATION: cloned antibody

<400> SEQUENCE: 210
```

| Gln | Pro | Gly | Gly | Ser | Leu | Arg | Leu | Ser | Cys | Ala | Ala | Ser | Gly | Phe | Thr |
|---|---|---|---|---|---|---|---|---|---|---|---|---|---|---|---|
| 1 | | | | 5 | | | | | 10 | | | | | 15 | |

| Leu | Ser | Ser | Ser | Ala | Met | Ser | Trp | Val | Arg | Gln | Ala | Pro | Gly | Lys | Gly |
|---|---|---|---|---|---|---|---|---|---|---|---|---|---|---|---|
| | | | 20 | | | | 25 | | | | | 30 | | | |

| Leu | Glu | Phe | Val | Ala | Val | Ser | Ser | Gly | Asn | Gly | Phe | Ser | Thr | Tyr | Tyr |
|---|---|---|---|---|---|---|---|---|---|---|---|---|---|---|---|
| | | 35 | | | | | 40 | | | | | 45 | | | |

| Gly | Asp | Ser | Val | Lys | Gly | Arg | Phe | Thr | Ile | Ser | Arg | Asp | Asn | Ser | Lys |
|---|---|---|---|---|---|---|---|---|---|---|---|---|---|---|---|
| | 50 | | | | | 55 | | | | | 60 | | | | |

| Asn | Met | Val | Tyr | Leu | Gln | Met | Asp | Ser | Leu | Arg | Ala | Glu | Asp | Thr | Ala |
|---|---|---|---|---|---|---|---|---|---|---|---|---|---|---|---|
| 65 | | | | | 70 | | | | | 75 | | | | | 80 |

| Lys | Tyr | His | Cys | Ala | Lys | Val | Arg | Tyr | Gly | Pro | Arg | Ser | His | Phe | Phe |
|---|---|---|---|---|---|---|---|---|---|---|---|---|---|---|---|
| | | | | 85 | | | | | 90 | | | | | 95 | |

| Phe | Asp | Pro | Trp | Gly | Gln | Gly | Thr | Leu | Val | Thr | Val | Ser | Ser |
|---|---|---|---|---|---|---|---|---|---|---|---|---|---|
| | | | 100 | | | | | 105 | | | | | 110 |

```
<210> SEQ ID NO 211
<211> LENGTH: 110
<212> TYPE: PRT
<213> ORGANISM: artificial sequence
<220> FEATURE:
<223> OTHER INFORMATION: cloned antibody
```

<400> SEQUENCE: 211

Gln Pro Gly Gly Ser Leu Arg Leu Ser Cys Ala Ala Ser Gly Phe Thr
1               5                   10                  15

Leu Ser Ser Ser Ala Met Ser Trp Val Arg Gln Ala Pro Gly Lys Gly
            20                  25                  30

Leu Glu Phe Val Ala Val Ser Gly Asn Gly Phe Ser Thr Tyr Tyr
        35                  40                  45

Gly Asp Ser Val Lys Gly Arg Phe Thr Ile Ser Arg Asp Asn Ser Lys
    50                  55                  60

Asn Met Val Tyr Leu Gln Met Asp Ser Leu Arg Ala Glu Asp Thr Ala
65                  70                  75                  80

Lys Tyr His Cys Ala Lys Val Arg Tyr Gly Pro Arg Ser His Phe Phe
                85                  90                  95

Phe Asp Pro Trp Gly Pro Gly Asn Pro Gly His Arg Leu Leu
            100                 105                 110

<210> SEQ ID NO 212
<211> LENGTH: 112
<212> TYPE: PRT
<213> ORGANISM: artificial sequence
<220> FEATURE:
<223> OTHER INFORMATION: cloned antibody

<400> SEQUENCE: 212

Ala Trp Tyr Ser Arg Gly Ser Pro Cys Leu Ser Cys Ala Ala Ser Gly
1               5                   10                  15

Phe Thr Leu Ser Ser Ser Ala Met Ser Trp Val Arg Gln Ala Pro Gly
            20                  25                  30

Lys Gly Leu Glu Phe Val Ala Val Ser Ser Gly Asn Gly Phe Ser Thr
            35                  40                  45

Tyr Tyr Gly Asp Ser Val Lys Gly Arg Phe Thr Ile Ser Arg Asp Asn
    50                  55                  60

Ser Lys Asn Met Val Tyr Leu Gln Met Asp Ser Leu Arg Ala Glu Asp
65                  70                  75                  80

Thr Ala Lys Tyr His Cys Ala Lys Val Arg Tyr Gly Pro Arg Ser His
                85                  90                  95

Phe Phe Phe Asp Pro Trp Gly Gln Gly Thr Leu Val Thr Val Ser Ser
            100                 105                 110

<210> SEQ ID NO 213
<211> LENGTH: 122
<212> TYPE: PRT
<213> ORGANISM: artificial sequence
<220> FEATURE:
<223> OTHER INFORMATION: cloned antibody

<400> SEQUENCE: 213

Glu Ser Asp Pro Gly Leu Val Lys Pro Ser Glu Thr Pro Ser Leu Thr
1               5                   10                  15

Cys Thr Val Ser Gly Gly Ser Ile Ser Ser Thr Met Tyr Phe Trp Gly
            20                  25                  30

Trp Ile Arg Gln Pro Pro Gly Lys Gly Leu Glu Trp Ile Ala Ser Ile
            35                  40                  45

Tyr Tyr Ser Gly Thr Thr Tyr Tyr Asn Pro Ser Leu Arg Ser Arg Val
    50                  55                  60

Thr Met Ser Val Asp Thr Ser Lys Asn Gln Leu Ser Leu Lys Leu Asn
65                  70                  75                  80

```
Ser Val Thr Ala Ala Asp Thr Ala Val Tyr Tyr Cys Ala Arg Pro Thr
                85                  90                  95

Ile Tyr Tyr Phe Asp Gly Arg Thr Ser Tyr Tyr Pro Gly Glu Ala Ala
            100                 105                 110

Phe Asp Ile Trp Gly Gln Gly Thr Thr Val
        115                 120

<210> SEQ ID NO 214
<211> LENGTH: 121
<212> TYPE: PRT
<213> ORGANISM: artificial sequence
<220> FEATURE:
<223> OTHER INFORMATION: cloned antibody

<400> SEQUENCE: 214

Pro Gly Leu Val Lys Pro Ser Glu Thr Leu Ser Leu Thr Cys Thr Val
1               5                   10                  15

Ser Gly Gly Ser Ile Ser Asn Ile Met Tyr Phe Trp Gly Trp Ile Arg
            20                  25                  30

Gln Pro Pro Gly Lys Gly Leu Glu Trp Ile Ala Ser Ile Tyr Tyr Ser
        35                  40                  45

Gly Thr Thr Tyr Tyr Asn Pro Ser Leu Arg Ser Arg Val Thr Met Ser
    50                  55                  60

Val Asp Thr Ser Lys Asn Gln Leu Ser Leu Lys Leu Asn Ser Val Thr
65                  70                  75                  80

Ala Ala Asp Thr Ala Val Tyr Tyr Cys Ala Arg Pro Thr Ile Tyr Tyr
                85                  90                  95

Phe Asp Gly Arg Thr Ser Tyr Tyr Pro Gly Glu Ala Ala Phe Asp Ile
            100                 105                 110

Trp Gly Gln Gly Thr Thr Val Thr Val
        115                 120

<210> SEQ ID NO 215
<211> LENGTH: 114
<212> TYPE: PRT
<213> ORGANISM: artificial sequence
<220> FEATURE:
<223> OTHER INFORMATION: cloned antibody

<400> SEQUENCE: 215

Glu Ser Asp Pro Gly Leu Val Gln Pro Ser Gln Thr Leu Ser Leu Thr
1               5                   10                  15

Cys Thr Val Ser Gly Gly Ser Leu Arg Ser Asp Asp Tyr Tyr Trp Ser
            20                  25                  30

Trp Ile Arg Gln Ser Pro Gly Lys Gly Leu Glu Trp Ile Ala Tyr Ile
        35                  40                  45

Ser Tyr Thr Gly Gly Thr Tyr Tyr Asn Pro Ser Leu Lys Ser Arg Val
    50                  55                  60

Thr Ile Ser Val Asp Thr Ser Arg Asn Gln Phe Ser Leu Arg Leu Arg
65                  70                  75                  80

Ser Val Thr Ala Ala Asp Ser Ala Val Tyr Phe Cys Ala Ser Thr Thr
                85                  90                  95

Ala Val Thr Thr Thr Phe Asp Tyr Trp Gly Arg Gly Thr Leu Val Thr
            100                 105                 110

Val Ser

<210> SEQ ID NO 216
```

<211> LENGTH: 104
<212> TYPE: PRT
<213> ORGANISM: artificial sequence
<220> FEATURE:
<223> OTHER INFORMATION: cloned antibody

<400> SEQUENCE: 216

```
Pro Val Gln Pro Leu Glu Phe Thr Phe Thr Asp His Trp Met His Trp
1               5                   10                  15

Val Arg Gln Ala Pro Gly Lys Gly Leu Val Trp Leu Ala Arg Ile Asn
            20                  25                  30

Arg Asp Gly Ser Asp Thr Thr Tyr Ala Asp Ser Val Thr Gly Arg Phe
        35                  40                  45

Thr Ile Ser Arg Asp Asn Gly Lys Asn Thr Val Ser Leu Gln Met Asp
    50                  55                  60

Ser Leu Ser Val Asp Asp Thr Ala Val Tyr Tyr Cys Ala Arg Gly Gly
65                  70                  75                  80

His His Thr Val Leu Ser Pro Leu Ser Asn Trp Phe Asp Pro Trp Gly
                85                  90                  95

Gln Gly Thr Leu Val Thr Val Ser
            100
```

<210> SEQ ID NO 217
<211> LENGTH: 110
<212> TYPE: PRT
<213> ORGANISM: artificial sequence
<220> FEATURE:
<223> OTHER INFORMATION: cloned antibody

<400> SEQUENCE: 217

```
Glu Ser Glu Gly Gly Leu Val Gln Pro Gly Gly Ser Leu Arg Leu Ser
1               5                   10                  15

Cys Ala Ala Ser Gly Phe Thr Phe Ser Ser Tyr Ala Met Thr Trp Val
            20                  25                  30

Arg Gln Ala Pro Gly Lys Gly Leu Glu Trp Val Ser Thr Met Thr Gly
        35                  40                  45

Ser Gly Gly Val Thr Tyr Tyr Ala Asp Val Leu Lys Gly Arg Phe Thr
    50                  55                  60

Ile Ser Arg Asp Asn Ser Lys Asn Thr Leu Tyr Leu Gln Met Asn Ser
65                  70                  75                  80

Leu Arg Ala Glu Asp Thr Ala Val Tyr Tyr Cys Ala Lys Gly Tyr Gly
                85                  90                  95

Leu Phe Asp Tyr Trp Gly Gln Gly Thr Leu Val Thr Val Ser
            100                 105                 110
```

<210> SEQ ID NO 218
<211> LENGTH: 115
<212> TYPE: PRT
<213> ORGANISM: artificial sequence
<220> FEATURE:
<223> OTHER INFORMATION: cloned antibody

<400> SEQUENCE: 218

```
Leu Ala Gly Val Glu Val Val Gln Pro Gly Gly Ser Leu Arg Leu Ser
1               5                   10                  15

Cys Ala Ala Ser Gly Phe Thr Phe Asp Asp Tyr Ala Met His Trp Leu
            20                  25                  30

Arg Gln Ile Pro Gly Lys Gly Leu Gln Trp Val Ser Leu Leu Ser Trp
        35                  40                  45
```

```
Asp Gly Val Ser Ala Tyr Tyr Ala Asp Ser Val Glu Gly Arg Phe Thr
        50                  55                  60

Ile Ser Arg Asp Asn Lys Asn Ser Leu Tyr Leu Gln Met Asn Ser
65                  70                  75                  80

Leu Arg Ala Glu Asp Val Ala Leu Tyr Tyr Cys Ala Lys Asp Met Gly
                85                  90                  95

Gly Ala Gln Arg Leu Pro Asp His Trp Gly Gln Gly Thr Leu Val Thr
                100                 105                 110

Val Ser Ser
        115

<210> SEQ ID NO 219
<211> LENGTH: 114
<212> TYPE: PRT
<213> ORGANISM: artificial sequence
<220> FEATURE:
<223> OTHER INFORMATION: cloned antibody

<400> SEQUENCE: 219

Gly Gly Gly Leu Val Gln Pro Gly Ala Ser Val Lys Val Ser Cys Lys
1               5                   10                  15

Ala Ser Gly Tyr Thr Phe Ser Asp Tyr Phe Met His Cys Val Arg Gln
                20                  25                  30

Ala Pro Gly Gln Gly Leu Glu Trp Met Gly Leu Val Asn Pro Thr Asn
            35                  40                  45

Gly Tyr Thr Ala Tyr Ala Pro Lys Phe Gln Gly Arg Val Thr Met Thr
        50                  55                  60

Arg Gln Arg Phe Thr Ser Thr Val Tyr Met Glu Leu Ser Ser Leu Arg
65                  70                  75                  80

Ser Glu Asp Thr Ala Val Tyr Phe Cys Ala Arg Val Lys Ser Ser Asp
                85                  90                  95

Ser Ile Asp Ala Phe Asp Ile Trp Gly Gln Gly Thr Met Val Thr Val
                100                 105                 110

Ser Ser

<210> SEQ ID NO 220
<211> LENGTH: 103
<212> TYPE: PRT
<213> ORGANISM: artificial sequence
<220> FEATURE:
<223> OTHER INFORMATION: cloned antibody

<400> SEQUENCE: 220

Arg Cys Pro Ala Lys Leu Leu Asp Thr Pro Phe Ser Val Tyr Phe Met
1               5                   10                  15

His Trp Val Arg Gln Ala Pro Gly Gln Gly Leu Glu Trp Met Gly Leu
                20                  25                  30

Val Asn Pro Thr Asn Gly Tyr Thr Ala Tyr Ala Pro Lys Phe Gln Gly
            35                  40                  45

Arg Val Thr Met Thr Arg Gln Arg Phe Thr Ser Thr Val Tyr Met Glu
        50                  55                  60

Leu Ser Ser Leu Arg Ser Glu Asp Thr Ala Val Tyr Phe Cys Ala Arg
65                  70                  75                  80

Val Lys Ser Ser Asp Ser Ile Asp Ala Phe Asp Ile Trp Gly Gln Gly
                85                  90                  95

Thr Met Val Thr Val Ser Ser
                100
```

<210> SEQ ID NO 221
<211> LENGTH: 103
<212> TYPE: PRT
<213> ORGANISM: artificial sequence
<220> FEATURE:
<223> OTHER INFORMATION: cloned antibody

<400> SEQUENCE: 221

Arg Cys Pro Ala Lys Leu Leu Asp Thr Pro Ser Gly Asp Tyr Phe Met
1               5                   10                  15

His Trp Val Arg Gln Ala Pro Gly Gln Gly Leu Glu Trp Met Gly Leu
            20                  25                  30

Val Asn Pro Thr Asn Gly Tyr Thr Ala Tyr Ala Pro Lys Phe Gln Gly
        35                  40                  45

Arg Val Thr Met Thr Arg Gln Arg Phe Thr Ser Thr Val Tyr Met Glu
    50                  55                  60

Leu Ser Ser Leu Arg Ser Glu Asp Thr Ala Val Tyr Phe Cys Ala Arg
65                  70                  75                  80

Val Lys Ser Ser Asp Ser Ile Asp Ala Phe Asp Ile Trp Gly Gln Gly
                85                  90                  95

Thr Met Val Thr Val Ser Ser
            100

<210> SEQ ID NO 222
<211> LENGTH: 115
<212> TYPE: PRT
<213> ORGANISM: artificial sequence
<220> FEATURE:
<223> OTHER INFORMATION: cloned antibody

<400> SEQUENCE: 222

Ser Gly Gly Leu Val Gln Arg Gly Ala Lys Val Leu Arg Leu Ser Cys
1               5                   10                  15

Val Ala Ser Gly Phe Thr Phe Ser Ser Ser Ala Met Ser Trp Val Arg
            20                  25                  30

Gln Ala Pro Gly Lys Gly Leu Glu Trp Val Ser Val Ile Ser Gly Asn
        35                  40                  45

Gly Phe Ser Thr Tyr Tyr Ala Asp Ser Val Lys Arg Phe Thr Ile Ser
    50                  55                  60

Arg Asp Asn Ser Lys Asn Thr Leu Tyr Leu Gln Met Asn Ser Leu Arg
65                  70                  75                  80

Ala Glu Asp Thr Ala Glu Tyr Tyr Cys Thr Lys Val Lys Tyr Gly Ser
                85                  90                  95

Gly Ser His Phe Trp Phe Asp Pro Trp Gly Gln Gly Thr Leu Val Thr
            100                 105                 110

Val Ser Ser
        115

<210> SEQ ID NO 223
<211> LENGTH: 83
<212> TYPE: PRT
<213> ORGANISM: artificial sequence
<220> FEATURE:
<223> OTHER INFORMATION: cloned antibody
<220> FEATURE:
<221> NAME/KEY: MISC_FEATURE
<222> LOCATION: (23)..(23)
<223> OTHER INFORMATION: Xaa is unknown
<220> FEATURE:
<221> NAME/KEY: MISC_FEATURE
<222> LOCATION: (29)..(29)

<223> OTHER INFORMATION: Xaa is unknown
<220> FEATURE:
<221> NAME/KEY: MISC_FEATURE
<222> LOCATION: (52)..(52)
<223> OTHER INFORMATION: Xaa is unknown
<220> FEATURE:
<221> NAME/KEY: MISC_FEATURE
<222> LOCATION: (76)..(76)
<223> OTHER INFORMATION: Xaa is unknown

<400> SEQUENCE: 223

Leu Gly Ser Pro Tyr Ser Ser Ala Met Ser Trp Val Arg Gln Ala
1               5                   10                  15

Pro Gly Lys Gly Leu Glu Xaa Val Ser Phe Ile Ser Xaa Asn Gly Leu
            20                  25                  30

Ser Ala Tyr Tyr Ala Asp Ser Val Lys Gly Arg Phe Thr Ile Ser Arg
        35                  40                  45

Asp Asn Ser Xaa Asn Thr Val Tyr Leu Gln Met Asn Ser Leu Arg Ser
    50                  55                  60

Glu Asp Thr Ala Glu Tyr Tyr Cys Val Lys Val Xaa Tyr Gly Ser Arg
65                  70                  75                  80

Ser His Phe

<210> SEQ ID NO 224
<211> LENGTH: 115
<212> TYPE: PRT
<213> ORGANISM: artificial sequence
<220> FEATURE:
<223> OTHER INFORMATION: cloned antibody

<400> SEQUENCE: 224

Val Glu Ser Gly Gly Val Val Gln Pro Gly Ala Lys Val Leu Arg Leu
1               5                   10                  15

Ser Cys Ala Ala Ser Gly Phe Ser Phe Glu Asp Tyr Ala Met His Trp
            20                  25                  30

Val Arg Gln Pro Pro Gly Lys Gly Leu Glu Trp Val Ala Leu Ile Ser
        35                  40                  45

Trp Asp Val Ile Ser Ala Tyr Tyr Ala Asp Ser Val Lys Gly Arg Phe
    50                  55                  60

Thr Ile Ser Arg Asp Asn Ser Lys Asn Ser Leu Tyr Leu Gln Met Asp
65                  70                  75                  80

Ser Leu Arg Pro Glu Asp Ser Gly Leu Tyr Tyr Cys Gly Arg Asp Ile
                85                  90                  95

Gly Gln Gln Arg Thr Met Asp Val Trp Gly Gln Gly Thr Thr Val Thr
            100                 105                 110

Val Ser Ser
        115

<210> SEQ ID NO 225
<211> LENGTH: 98
<212> TYPE: PRT
<213> ORGANISM: artificial sequence
<220> FEATURE:
<223> OTHER INFORMATION: cloned antibody

<400> SEQUENCE: 225

Ala Ala Ser Gly Phe Ile Phe Asp Asp Phe Ala Met His Trp Phe Gln
1               5                   10                  15

Ala Val Pro Gly Lys Gly Leu Gln Trp Val Gly Leu Met Ser Trp Asp
            20                  25                  30

```
Gly Val Ser Ala Tyr Tyr Ala Asp Ser Val Glu Gly Arg Phe Thr Ile
            35                  40                  45

Ser Arg Asp Asn Lys Lys Asn Ala Leu Tyr Leu Gln Met Asn Ser Leu
 50                  55                  60

Gly Val Glu Asp Thr Ala Leu Tyr Phe Cys Ala Lys Asp Met Gly Gly
 65                  70                  75                  80

Gly Leu Arg Phe Pro His Phe Trp Gly Gln Gly Thr Pro Val Thr Val
                85                  90                  95

Ser Ala

<210> SEQ ID NO 226
<211> LENGTH: 111
<212> TYPE: PRT
<213> ORGANISM: artificial sequence
<220> FEATURE:
<223> OTHER INFORMATION: cloned antibody

<400> SEQUENCE: 226

Phe Trp Leu Gly Gly Pro Trp Arg Leu Ser Cys Ala Val Ser Gly Tyr
 1               5                  10                  15

Thr Leu Ser Ser Ser Ala Met Ile Trp Val Arg Gln Pro Pro Gly Lys
            20                  25                  30

Gly Leu Glu Phe Val Ser Val Ile Ser Gly Asn Gly Leu Ser Ala Tyr
            35                  40                  45

Tyr Ala Asp Ser Val Lys Gly Arg Phe Thr Ile Ser Arg Asp Asn Ser
 50                  55                  60

Lys Asn Thr Val Tyr Leu Gln Met Asn Ser Leu Arg Ala Glu Asp Thr
 65                  70                  75                  80

Ala Glu Tyr Tyr Cys Val Lys Val Lys Tyr Gly Ser Arg Ser His Phe
                85                  90                  95

Phe Phe Asp Ser Trp Gly Gln Gly Thr Leu Val Ser Val Ser Pro
               100                 105                 110

<210> SEQ ID NO 227
<211> LENGTH: 115
<212> TYPE: PRT
<213> ORGANISM: artificial sequence
<220> FEATURE:
<223> OTHER INFORMATION: cloned antibody

<400> SEQUENCE: 227

Gly Gly Gly Leu Val Gln Pro Gly Ala Ser Leu Arg Leu Ser Cys Val
 1               5                  10                  15

Ala Ser Gly Phe Thr Leu Ser Ser Ser Ala Met Ser Cys Val Arg Gln
            20                  25                  30

Ala Pro Gly Lys Gly Leu Glu Trp Val Ser Val Ser Ser Gly Asn Gly
            35                  40                  45

Phe Ser Ala Tyr Tyr Ala Asp Ser Val Lys Gly Arg Phe Thr Ile Ser
 50                  55                  60

Arg Asp Asn Ser Lys Asn Thr Leu Tyr Leu Gln Met Asn Ser Leu Val
 65                  70                  75                  80

Ala Glu Asp Thr Ala Glu Tyr Tyr Cys Thr Lys Val Asn Tyr Gly Ser
                85                  90                  95

Arg Ser His Phe Tyr Phe Gly Ser Trp Gly His Gly Thr Leu Val Ile
               100                 105                 110

Val Ser Ser
115
```

-continued

<210> SEQ ID NO 228
<211> LENGTH: 114
<212> TYPE: PRT
<213> ORGANISM: artificial sequence
<220> FEATURE:
<223> OTHER INFORMATION: cloned antibody

<400> SEQUENCE: 228

Trp Gly Arg Arg Gly Pro Ala Trp Gly Val Pro Val Gly Ser Pro Val
1               5                   10                  15

Gln Pro Leu Gly Tyr Thr Phe Asp Asp Tyr Ala Met His Trp Leu Arg
            20                  25                  30

Gln Ile Pro Gly Lys Gly Leu Gln Trp Val Ser Leu Leu Ser Trp Asp
        35                  40                  45

Gly Val Ser Ala Tyr Tyr Ala Asp Ser Val Glu Gly Arg Phe Thr Ile
    50                  55                  60

Ser Arg Asp Asn Lys Lys Asn Ser Leu Tyr Leu Gln Met Asn Ser Leu
65                  70                  75                  80

Val Ala Glu Asp Thr Ala Leu Tyr Phe Cys Ala Lys Asp Met Gly Gly
                85                  90                  95

Ala Gln Arg Leu Pro Asp His Trp Gly Gln Gly Thr Leu Val Thr Val
            100                 105                 110

Ser Ser

<210> SEQ ID NO 229
<211> LENGTH: 115
<212> TYPE: PRT
<213> ORGANISM: artificial sequence
<220> FEATURE:
<223> OTHER INFORMATION: cloned antibody
<220> FEATURE:
<221> NAME/KEY: MISC_FEATURE
<222> LOCATION: (70)..(70)
<223> OTHER INFORMATION: Xaa is unknown

<400> SEQUENCE: 229

Trp Thr Gly Gly Val Val Gln Pro Gly Gly Ser Leu Arg Val Ser
1               5                   10                  15

Val Ala Ala Ser Gly Tyr Thr Phe Asp Asp Tyr Ala Met His Trp Leu
            20                  25                  30

Arg Gln Ile Pro Gly Lys Gly Leu Gln Trp Val Ser Leu Leu Ser Trp
        35                  40                  45

Asp Gly Val Ser Ala Tyr Tyr Ala Asp Ser Val Glu Gly Arg Phe Thr
    50                  55                  60

Ile Ser Arg Asp Asn Xaa Lys Asn Ser Leu Tyr Leu Gln Met Asn Ser
65                  70                  75                  80

Leu Ile Ala Glu Asp Thr Ala Leu Tyr Phe Cys Ala Lys Asp Met Gly
                85                  90                  95

Gly Ala Gln Arg Leu Pro Asp His Trp Gly Gln Gly Thr Leu Val Thr
            100                 105                 110

Val Ser Ser
        115

<210> SEQ ID NO 230
<211> LENGTH: 120
<212> TYPE: PRT
<213> ORGANISM: artificial sequence
<220> FEATURE:
<223> OTHER INFORMATION: cloned antibody -continued

```
<400> SEQUENCE: 230

Ala Glu Ser Gly Gly Val Val Gln Pro Gly Gly Ser Leu Arg Leu
1               5                   10                  15

Ser Cys Ala Ala Ser Gly Phe Thr Phe Ser Arg Tyr Thr Leu Ser Trp
                20                  25                  30

Val Arg Gln Ala Pro Gly Lys Gly Leu Glu Trp Val Ser Tyr Ile Ser
            35                  40                  45

Thr Asp Gly Ser Thr Ile Tyr Tyr Thr Asp Ser Val Lys Gly Arg Phe
    50                  55                  60

Thr Ile Ser Arg Asp Asn Ala Lys Asn Ser Leu Ser Leu Gln Met Ile
65                  70                  75                  80

Ser Leu Arg Asp Glu Asp Thr Ala Val Tyr Tyr Cys Ala Arg Val Phe
                85                  90                  95

Phe Gly Gly Asn Phe Arg Ala His Trp Tyr Phe Asp Leu Trp Gly Arg
                100                 105                 110

Gly Thr Leu Val Ala Val Ser Ser
            115                 120

<210> SEQ ID NO 231
<211> LENGTH: 47
<212> TYPE: DNA
<213> ORGANISM: artificial sequence
<220> FEATURE:
<223> OTHER INFORMATION: primer

<400> SEQUENCE: 231
agaatttgac tagttggcaa gaggcacgtt cttttctttg ttgccgt                47
```